(12) United States Patent
Qian et al.

(10) Patent No.: US 11,299,475 B2
(45) Date of Patent: Apr. 12, 2022

(54) PROSTACYCLIN RECEPTOR AGONIST

(71) Applicant: MEDSHINE DISCOVERY INC., Jiangsu (CN)

(72) Inventors: Wenyuan Qian, Shanghai (CN); Chundao Yang, Shanghai (CN); Guanghai Xu, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 14 days.

(21) Appl. No.: 16/967,546

(22) PCT Filed: Feb. 2, 2019

(86) PCT No.: PCT/CN2019/074575
§ 371 (c)(1),
(2) Date: Aug. 5, 2020

(87) PCT Pub. No.: WO2019/154363
PCT Pub. Date: Aug. 15, 2019

(65) Prior Publication Data
US 2021/0087168 A1    Mar. 25, 2021

(30) Foreign Application Priority Data
Feb. 7, 2018 (CN) .......................... 201810124492.3

(51) Int. Cl.
*C07D 401/14* (2006.01)
*A61P 9/12* (2006.01)
*C07D 241/20* (2006.01)
*C07D 401/04* (2006.01)
*C07D 417/14* (2006.01)

(52) U.S. Cl.
CPC .............. *C07D 401/14* (2013.01); *A61P 9/12* (2018.01); *C07D 241/20* (2013.01); *C07D 401/04* (2013.01); *C07D 417/14* (2013.01)

(58) Field of Classification Search
CPC .. C07D 401/14; C07D 401/04; C07D 241/20; C07D 417/14; A61P 9/12
See application file for complete search history.

(56) References Cited

FOREIGN PATENT DOCUMENTS

| CN | 1516690 A | 7/2004 |
|----|-----------|--------|
| EP | 1400518 A1 | 3/2004 |
| EP | 2370413 B1 | 8/2015 |
| JP | H1069030 A | 3/1998 |
| WO | WO-2002088084 A1 | 11/2002 |
| WO | WO-2009117095 A1 | 9/2009 |
| WO | WO-2009157398 A1 | 12/2009 |
| WO | WO-2010068242 A1 | 6/2010 |
| WO | WO-2010077275 A1 | 7/2010 |
| WO | WO-2010150865 A1 | 12/2010 |
| WO | WO-2011017612 A1 | 2/2011 |
| WO | WO-2011024874 A1 | 3/2011 |
| WO | WO-2011037613 A1 | 3/2011 |
| WO | WO-2018019296 A1 | 2/2018 |

OTHER PUBLICATIONS

European Extended Search Report issued in European Patent Application No. 19751459.9, dated Nov. 18, 2020.
May 6, 2019 International Search Report issued in International Patent Application No. PCT/CN2019/074575.
May 6, 2020 Written Opinion of the International Searching Authority issued in International Patent Application No. PCT/CN2019/074575.

*Primary Examiner* — D Margaret M Seaman
(74) *Attorney, Agent, or Firm* — Harness, Dickey & Pierce, P.L.C.

(57) ABSTRACT

A compound represented by formula (I) or an isomer or a pharmaceutically acceptable salt thereof. The present invention also relates to an application of the same in preparing a drug for treating a disease related to a $PGI_2$ receptor.

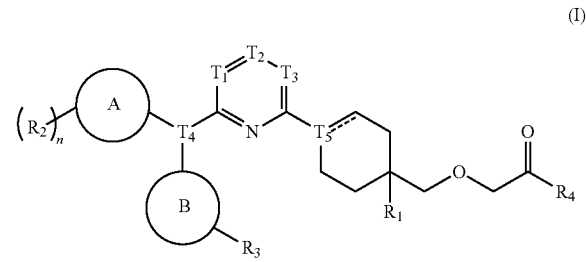

20 Claims, 1 Drawing Sheet

PROSTACYCLIN RECEPTOR AGONIST

CROSS-REFERENCE TO RELATED APPLICATIONS

This application is a U.S. National Phase Application under 35 U.S.C. 371 of International Application No. PCT/CN2019/074575, filed Feb. 2, 2019, which claims the benefit of Chinese Patent Application No. CN 201810124492.3, filed Feb. 7, 2018. The entire disclosures of the above applications are incorporated herein by reference.

FIELD OF INVENTION

The present disclosure relates to a compound represented by formula (I), an isomer thereof or a pharmaceutically acceptable salt thereof, and relates to a use thereof in the manufacture of a medicament in the treatment of $PGI_2$ receptor related diseases.

PRIOR ARTS

Prostacyclin ($PGI_2$) is one of the metabolites of arachidonic acid (AA), which is mainly produced by vascular endothelial cells. In the organism, arachidonic acid is converted into prostaglandin $G_2$ ($PGG_2$) under the action of cyclooxygenase, which generates prostaglandin $H_2$ ($PGH_2$) under the action of peroxidase. And prostaglandin $H_2$ is an important metabolic intermediate through which a series of different prostaglandins can be obtained in different routes. Under the action of prostacyclin synthase, prostaglandin $H_2$ is converted into prostacyclin. Prostacyclin receptor (IP receptor) is the main target of prostacyclin. After the prostacyclin receptor is activated, it is coupled with regulatory proteins and activates adenylate cyclase (AC), which further raises the content of cyclic adenosine monophosphate (cAMP) in target cells and plays a role in vasodilation, anti-platelet aggregation, anti-hyperplasia, immune regulation and the like at the meantime.

Pulmonary arterial hypertension (PAH) refers to a group of clinical pathophysiological syndromes in which the average pressure of the pulmonary artery is ≥25 mmHg detected by a right catheter at resting state at sea level, and it is mainly characterized by vasospasm, intimal hyperplasia and remodeling of pulmonary arterioles which results in a continued increase in pulmonary vascular resistance and ultimately results in right-sided heart failure and death of patients. Prostacyclin synthesis reduces in patients with pulmonary arterial hypertension, so it is a viable alternative therapy to use prostacyclin and analogs thereof. Traditional prostacyclin and analogs thereof mainly include epoprostanol, iloprost, beraprost and treprostinil, and the common disadvantages of which are that they are expensive, poor in metabolic stability, having short half-life and administered by injection mostly. At present, many experts believe that intravenously administered prostacyclin is the most reliable drug for the treatment of patients with the most severe pulmonary arterial hypertension, but due to the short half-life of prostacyclin, patients may face a potentially fatal risk of rebound pulmonary hypertension if the infusion is suddenly interrupted.

In order to overcome these disadvantages, a number of novel, non-prostaglandin, orally administered and long-acting prostacyclin receptor agonists have been researched and developed in recent years, in which Selexipag is the first compound approved by the FDA for these analogues. The compound was first developed by Nippon Shinyaku and a licensing agreement was signed with Actelion, Switzerland in April 2008. The drug was marketed at the end of 2015 with the trade name Uptravi, and related patents of which are mainly WO2002088084, WO2009157398, WO2010150865 and WO2011024874 and the like. Ralinepag is another important non-prostaglandin prostacyclin receptor agonist which is developed by Arena and is currently in clinical phase II, and related patents of which are mainly WO2009117095 and WO2011037613.

CONTENT OF THE PRESENT INVENTION

The present disclosure provides a compound represented by formula (I), an isomer or a pharmaceutically acceptable salt thereof,

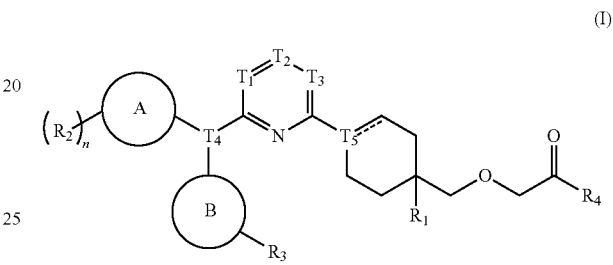

(I)

wherein,
n is 1 or 2;
$R_1$ is H or F;
each of $R_2$ is independently selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_b$;
each of $R_b$ is independently selected from the group consisting of F, Cl, Br, I, OH and $NH_2$;
$R_3$ is selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_c$;
each of $R_c$ is independently selected from the group consisting of F, Cl, Br, I, OH and $NH_2$;
$R_4$ is selected from the group consisting of OH, $C_{1-6}$ alkoxy and $C_{1-6}$ alkyl-$S(=O)_2$—NH—, wherein $C_{1-6}$ alkoxy and $C_{1-6}$ alkyl-$S(=O)_2$—NH— are optionally substituted by one, two or three of $R_d$;
each of $R_d$ is independently selected from the group consisting of F, Cl, Br, I, OH and $NH_2$;
ring A is a phenyl or a 5- to 6-membered heteroaryl;
ring B is a phenyl, a 5- to 6-membered heteroaryl, a $C_{3-6}$ cycloalkyl or a 3- to 6-membered heterocycloalkyl;
$T_1$ is N or CH;
$T_2$ is N or CH;
$T_3$ is N or CH;
$T_4$ is N or C($R_5$);
$T_5$ is N, CH or C;

$R_5$ is selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_e$;

each of $R_e$ is independently selected from the group consisting of F, Cl, Br, I, OH and $NH_2$;

each of $C_{1-6}$ heteroalkyl, 3- to 6-membered heterocycloalkyl and 5- to 6-membered heteroaryl contains one, two or three of heteroatom or heteroatomic group independently selected from the group consisting of —O—, —NH—, —S— and N.

In some embodiments of the present disclosure, each of $R_2$ is independently selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_b$, and other variables are as defined in the present disclosure.

In some embodiments of the present disclosure, each of $R_2$ is independently selected from the group consisting of H, F, Cl, Br, I, OH, $NH_2$, Me and

wherein Me and

are optionally substituted by one, two or three of $R_b$, and other variables are as defined in the present disclosure.

In some embodiments of the present disclosure, each of $R_2$ is independently selected from the group consisting of H, F, Cl, Br, I, OH, $NH_2$, Me, $CF_3$,

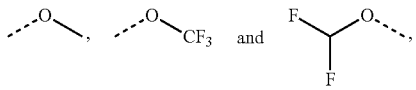

and other variables are as defined in the present disclosure.

In some embodiments of the present disclosure, $R_3$ is selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_c$, and other variables are as defined in the present disclosure.

In some embodiments of the present disclosure, $R_3$ is selected from the group consisting of H, F, Cl, Br, I, OH, $NH_2$, Me and

wherein Me and

are optionally substituted by one, two or three of $R_c$, and other variables are as defined in the present disclosure.

In some embodiments of the present disclosure, $R_3$ is selected from the group consisting of H, F, Cl, Br, I, OH, $NH_2$, Me, $CF_3$,

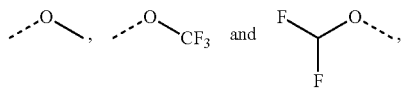

and other variables are as defined in the present disclosure.

In some embodiments of the present disclosure, $R_4$ is selected from the group consisting of OH, $C_{1-3}$ alkoxy and $C_{1-3}$ alkyl-S(=O)$_2$—NH—, wherein $C_{1-3}$ alkoxy and $C_{1-3}$ alkyl-S(=O)$_2$—NH— are optionally substituted by one, two or three of $R_d$, and other variables are as defined in the present disclosure.

In some embodiments of the present disclosure, $R_4$ is selected from the group consisting of OH,

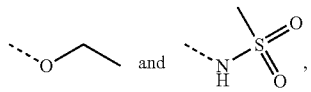

wherein

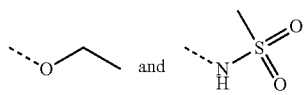

are optionally substituted by one, two or three of $R_d$, and other variables are as defined in the present disclosure.

In some embodiments of the present disclosure, $R_4$ is selected from the group consisting of OH,

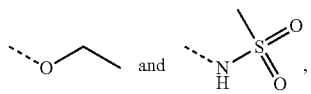

and other variables are as defined in the present disclosure.

In some embodiments of the present disclosure, $R_5$ is selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_e$, and other variables are as defined in the present disclosure.

In some embodiments of the present disclosure, $R_5$ is selected from the group consisting of H, OH, $NH_2$, F, Cl, Br, I, Me and

wherein Me and

are optionally substituted by one, two or three of $R_e$, and other variables are as defined in the present disclosure.

In some embodiments of the present disclosure, R₅ is selected from the group consisting of H, OH, NH₂, F, Cl, Br, I, Me and

and other variables are as defined in the present disclosure.

In some embodiments of the present disclosure, T₁ is CH, T₂ is CH, T₃ is CH, and other variables are as defined in the present disclosure.

In some embodiments of the present disclosure, T₁ is N, T₂ is CH, T₃ is CH, and other variables are as defined in the present disclosure.

In some embodiments of the present disclosure, T₁ is CH, T₂ is N, T₃ is CH, and other variables are as defined in the present disclosure.

In some embodiments of the present disclosure, T₁ is CH, T₂ is CH, T₃ is N, and other variables are as defined in the present disclosure.

In some embodiments of the present disclosure, the ring A is a phenyl or a pyridyl, and other variables are as defined in the present disclosure.

In some embodiments of the present disclosure, the structure moiety

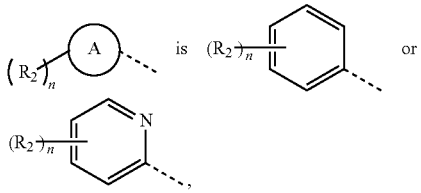

and other variables are as defined in the present disclosure.

In some embodiments of the present disclosure, the structure moiety

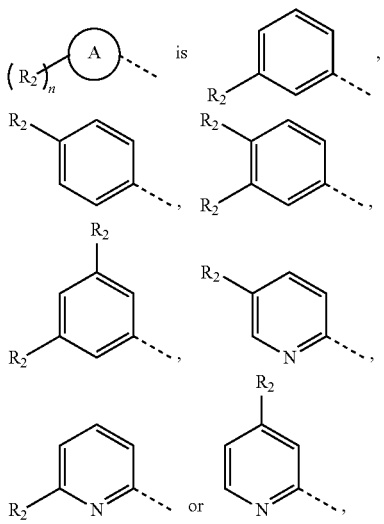

and other variables are as defined in the present disclosure.

In some embodiments of the present disclosure, the structure moiety

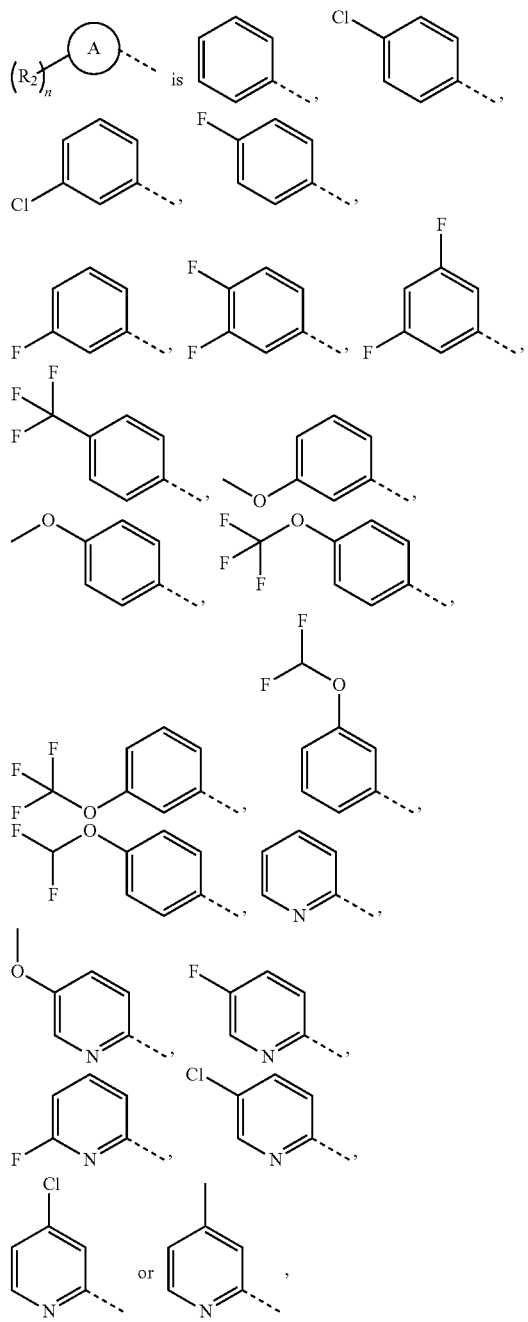

and other variables are as defined in the present disclosure.

In some embodiments of the present disclosure, ring B is a phenyl, a pyridyl, a thiazolyl or a cyclohexyl.

In some embodiments of the present disclosure, the structure moiety

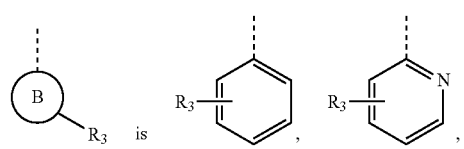

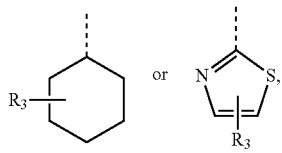

and other variables are as defined in the present disclosure.

In some embodiments of the present disclosure, the structure moiety

and other variables are as defined in the present disclosure.

In some embodiments of the present disclosure, the structure moiety

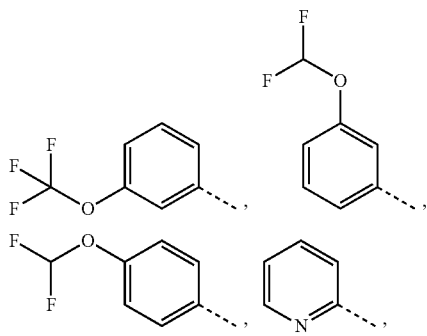

and other variables are as defined in the present disclosure.

In some embodiments of the present disclosure, the compound, the isomer or the pharmaceutically acceptable salt thereof, is selected from the group consisting of (I-1)

(I-2)

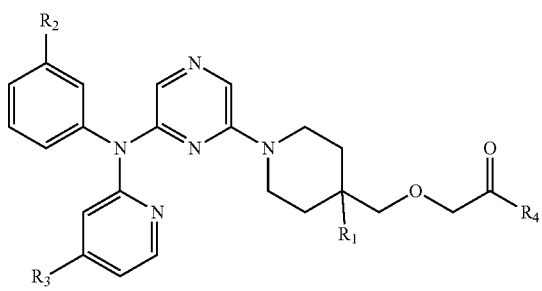
(I-3)
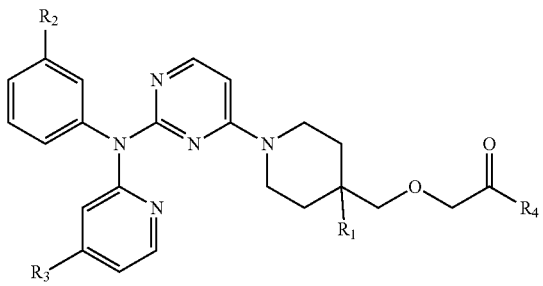
(I-8)
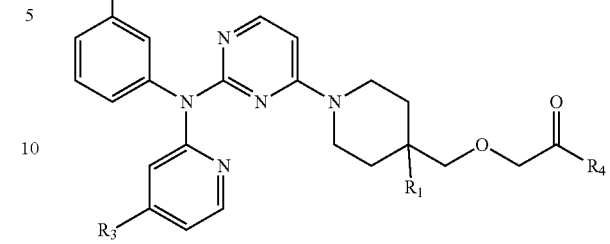
(I-4)
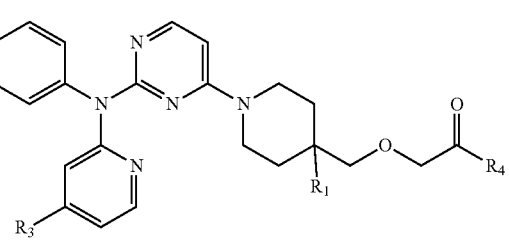
(I-9)
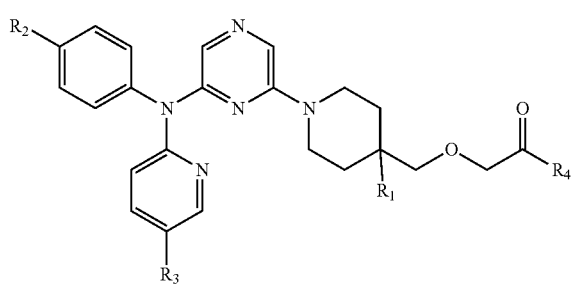
(I-5)
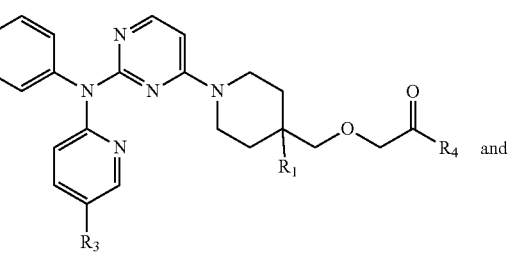
(I-10)
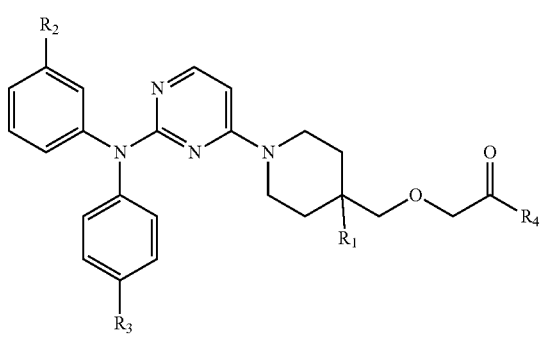
(I-6)
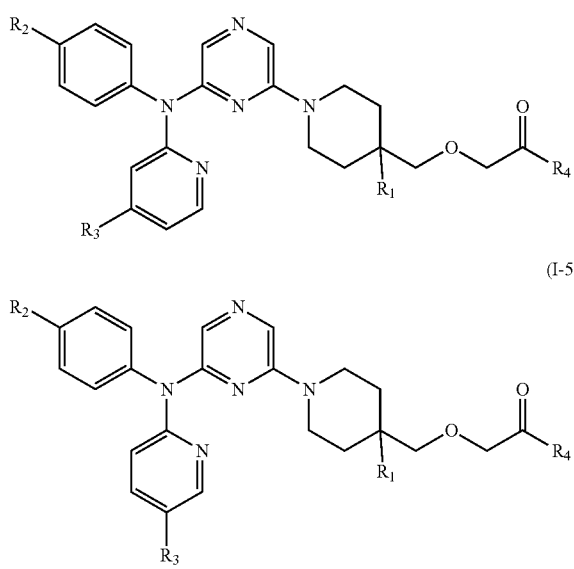
(I-7)
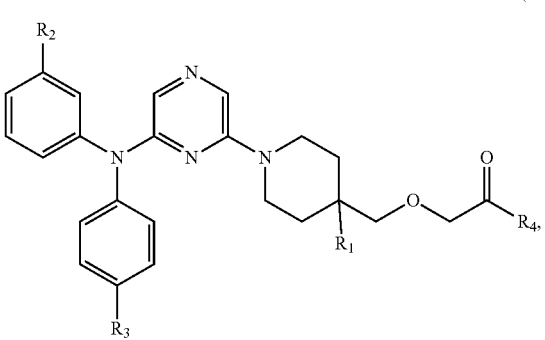
(I-11)
wherein, $R_1$, $R_2$, $R_3$ and $R_4$ are as defined above.
Other embodiments of the present disclosure can be obtained by arbitrary combinations of the above variables.

The present disclosure also provides the compound, the isomer or the pharmaceutically acceptable salt thereof, which is selected from the group consisting of
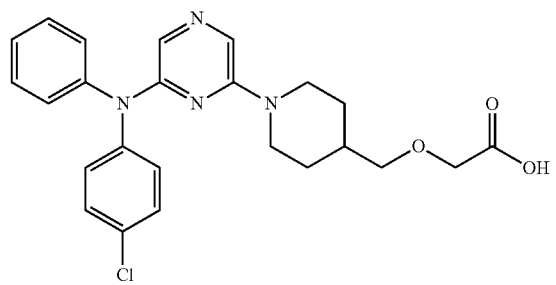
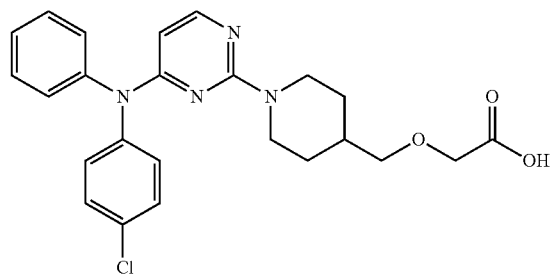
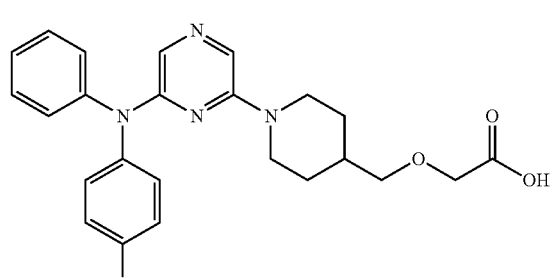
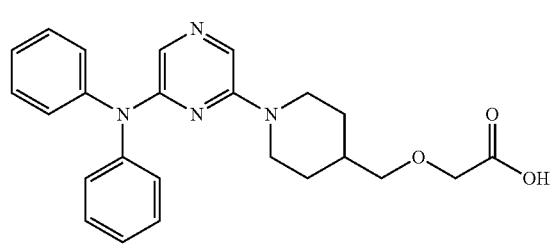
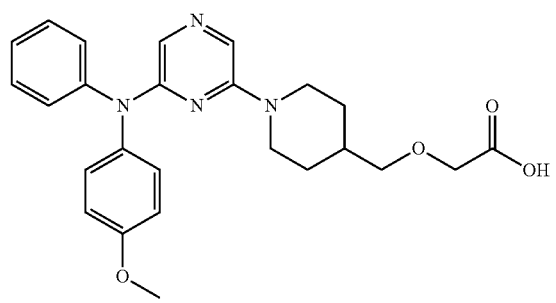
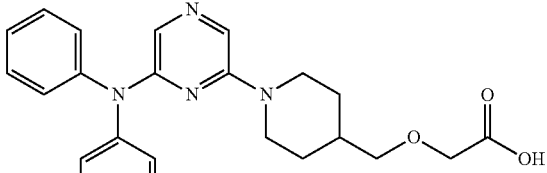
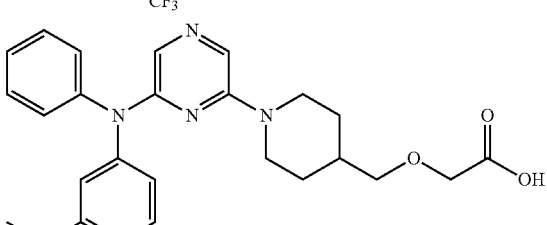
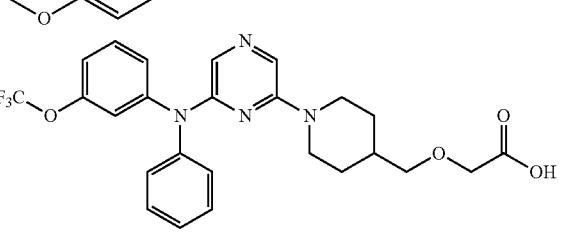
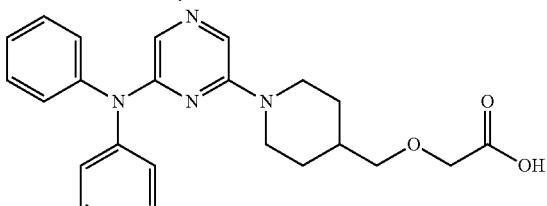
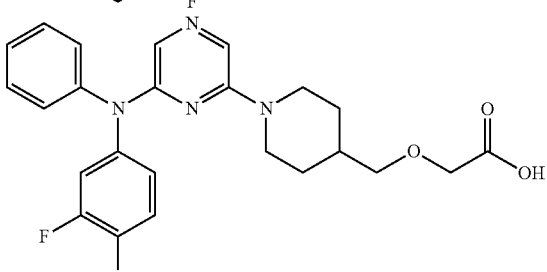
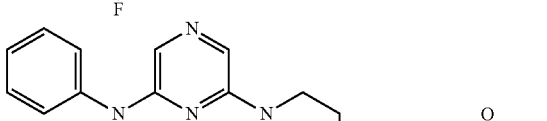
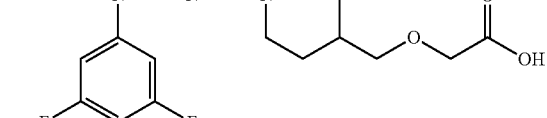
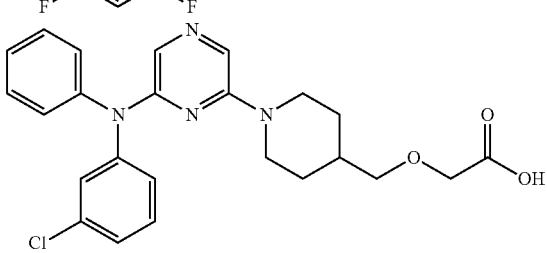

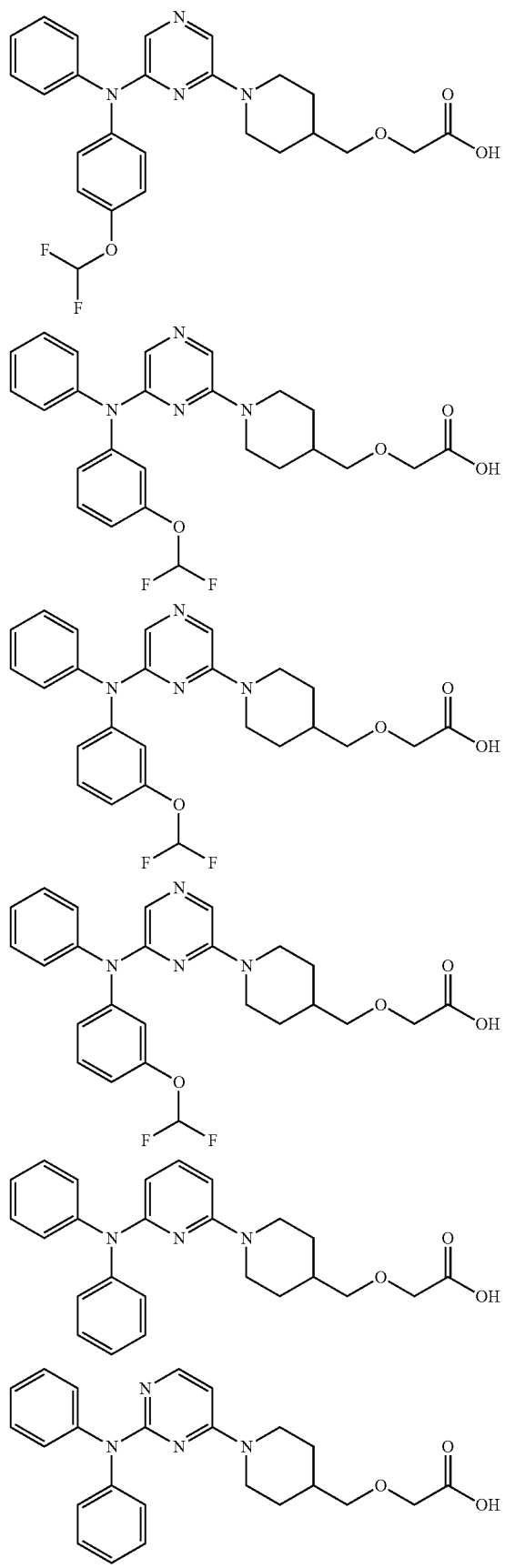

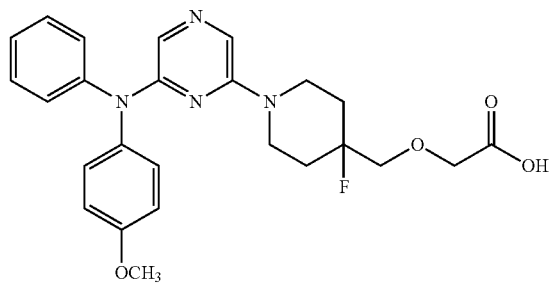
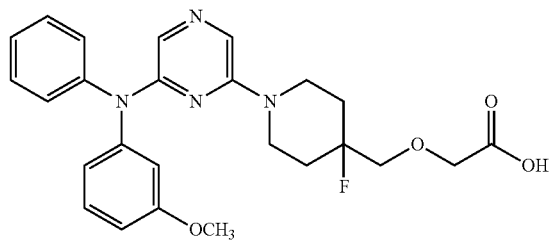
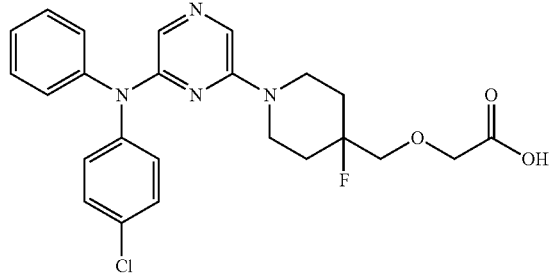
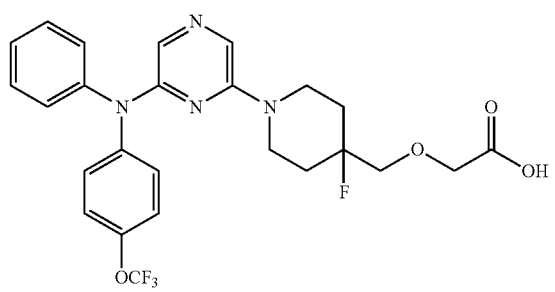
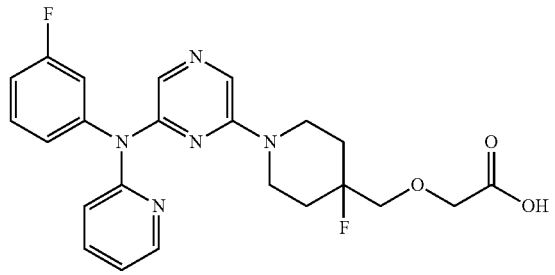
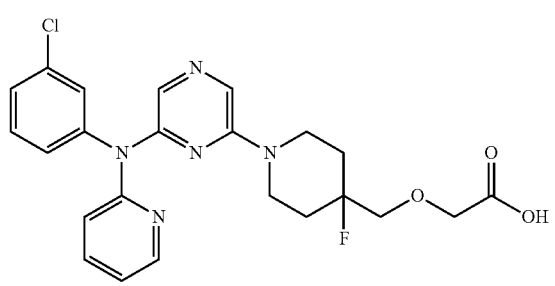
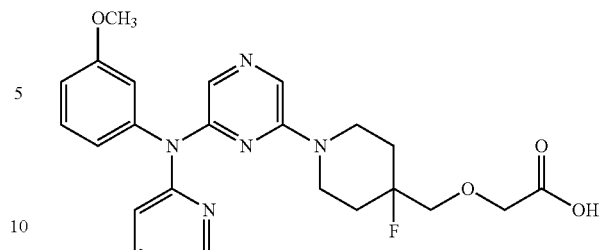
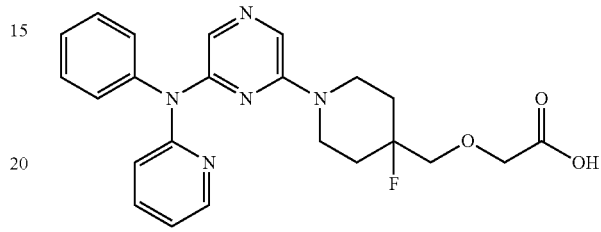
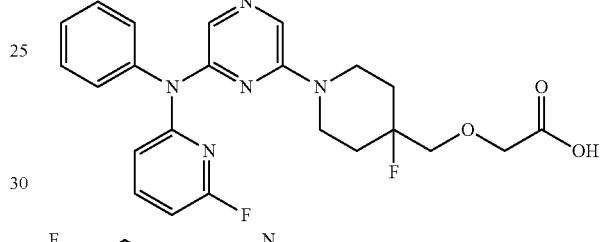
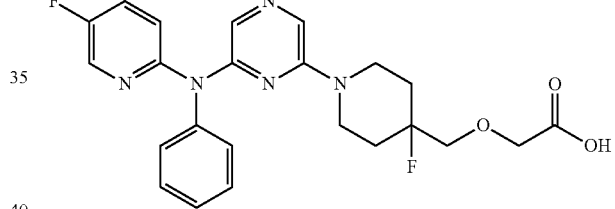
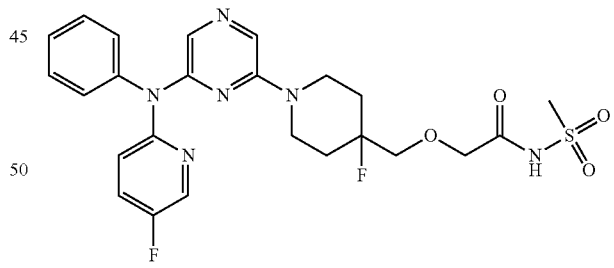
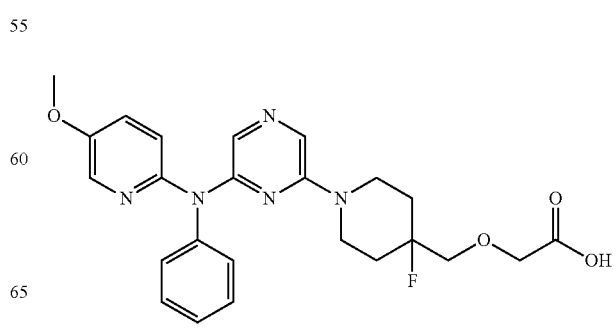

-continued
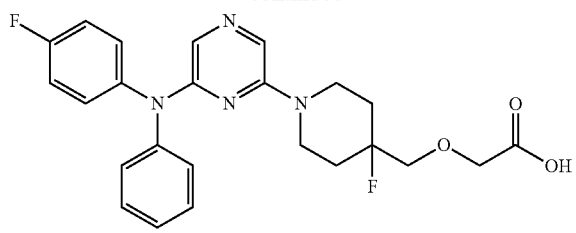
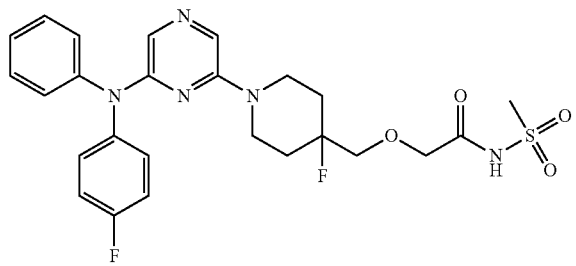
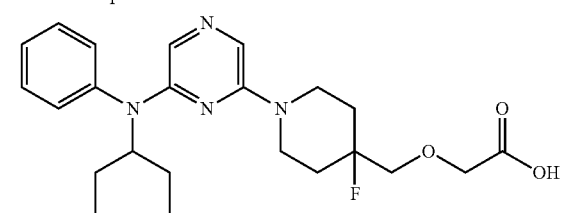
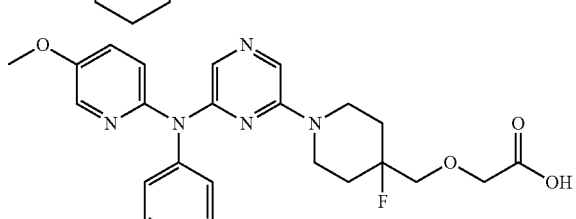
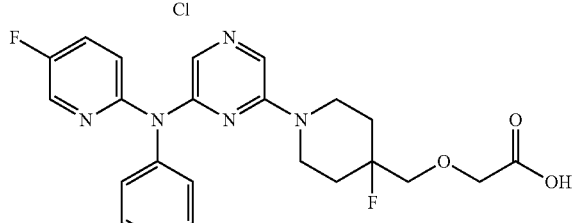
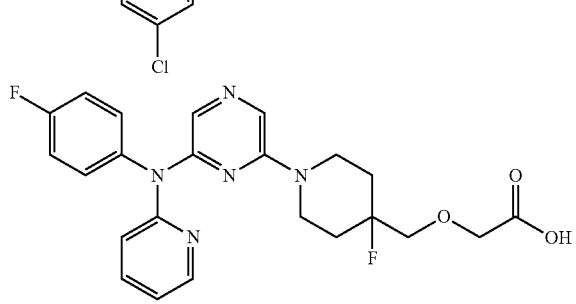
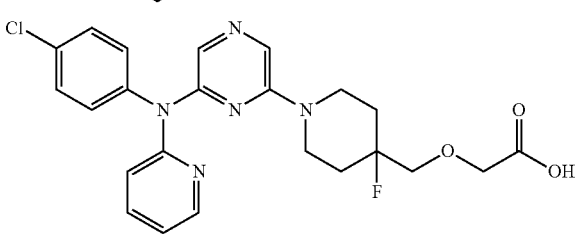
-continued
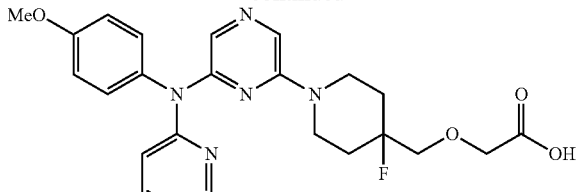
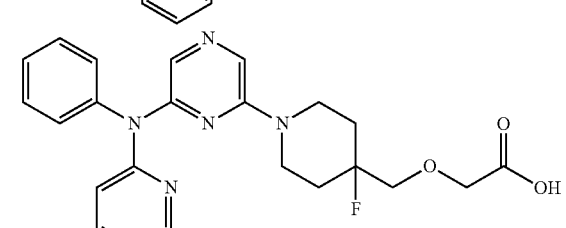
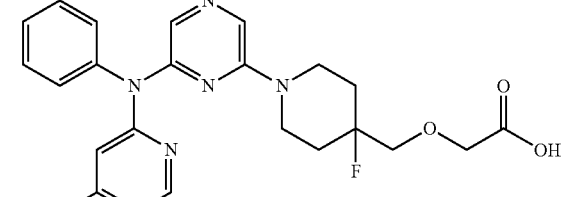
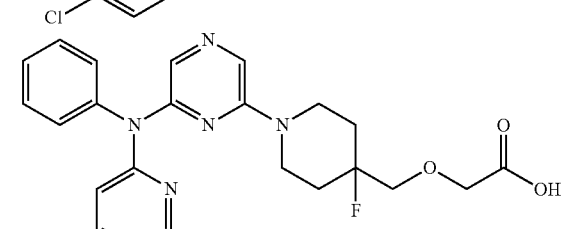
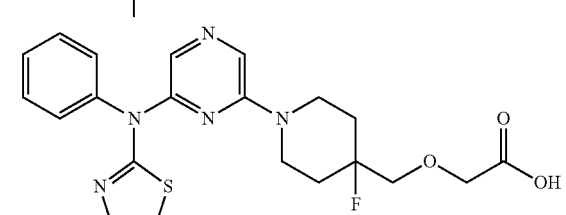
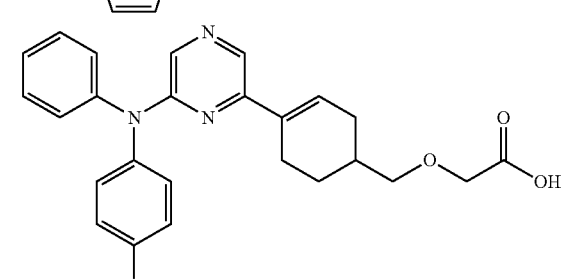
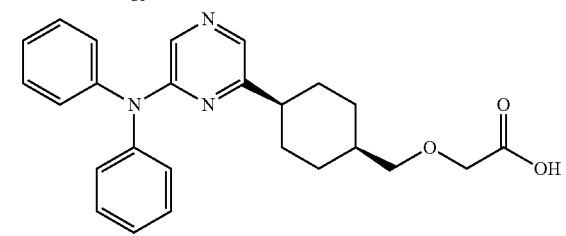

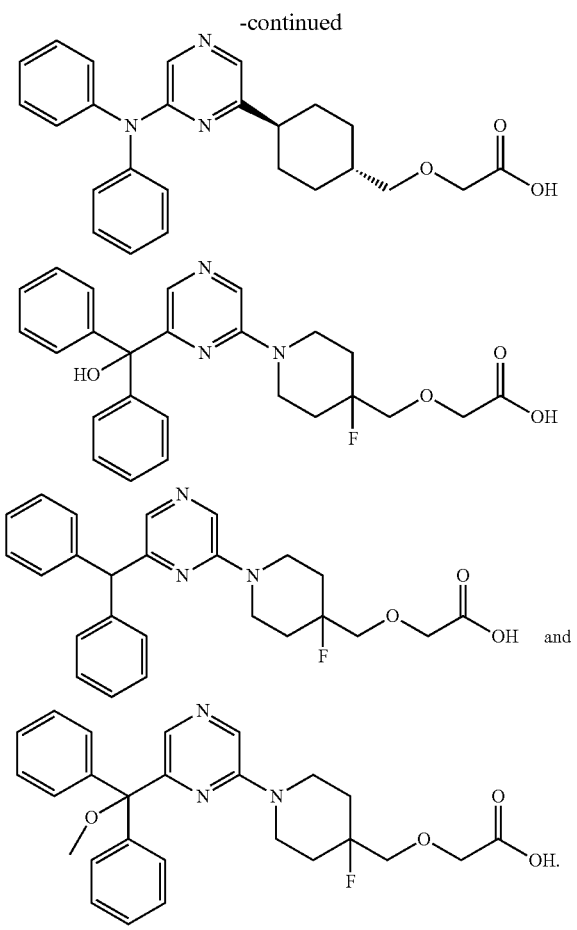

The present disclosure also provides a use of the compound, the isomer or the pharmaceutically acceptable salt thereof in the manufacture of a medicament in the treatment of PGI$_2$ receptor related diseases.

In some embodiments of the present disclosure, in the use mentioned above, the medicament is useful to pulmonary arterial hypertension, systemic sclerosis, acute pulmonary embolism, renal failure, heart failure, rhinitis, thrombosis, arteriosclerosis, chronic thromboembolic pulmonary arterial hypertension, Raynaud's disease, headache, migraine or cardiac arrest.

Technical Effect

The present disclosure is related to a series of novel prostacyclin receptor agonist, which has the characteristics of high activity, good metabolic stability, good solubility, suitable for oral administration and the like. Compared with the reference compound, the compound of the present disclosure has improved activity, improved solubility and binding rate of plasma protein, especially binding of plasma protein in human, and oral bioavailability is also significantly improved.

Definition and Description

Unless otherwise indicated, the following terms used in the description and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The compound of the present disclosure may have a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope of the present disclosure. The substituent such as alkyl can have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(+)" refers to dextrorotation, "(−)" refers to levorotation, "(±)" refers to racemization.

Unless otherwise specified, the absolute configuration of a stereogenic center is represented by a wedged solid bond (◢) and a wedged dashed bond (◌), and the relative configuration of a stereogenic center is represented by a straight solid bond (◢) and a straight dashed bond (◌). A wave line (∿) represents a wedged solid bond (◢) or a wedged dashed bond (◌), or represents a straight solid bond (◢) or a straight dashed bond (◌).

The compounds of the present disclosure may be present in particular. Unless otherwise indicated, the term "tautomer" or "tautomeric form" refer to the fact that the isomers with different functional groups are in dynamic equilibrium at room temperature and can be rapidly converted into each other. If tautomers are possible (e.g., in solution), the chemical equilibrium of the tautomers can be achieved. For example, proton tautomers (also known as prototropic tautomers) include interconversions by proton migration, such as keto-enol isomerization and imine-enamine isomerization.

Valence tautomers include the mutual transformation caused by bonding electrons transfer. A specific example of keto-enol tautomerization is the interconversion between two tautomers pentane-2,4-dione and 4-hydroxypent-3-en-2-one.

Unless otherwise specified, the term "enriched in one isomer", "isomer enriched", "enriched in one enantiomer" or "enantiomer enriched" refers to the content of one of the isomers or enantiomers is less than 100%, and the content of this isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomers of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form salts in the form of diastereomers which are then subjected to diastereomeric resolution through conventional methods in the art to give the pure enantiomer. In addition, the enantiomer or diastereomer is generally isolated through chromatography which uses a chiral stationary phase and optionally combines with a chemical derivative method (such as carbamate generated from amine). The compound of the present disclosure may contain an unnatural proportion of atomic isotope at one or more atoms that constitute the compound. For example, the compound can be radiolabeled with a radioactive isotope, such as tritium ($^{3}H$), iodine-125 ($^{125}I$) or C-14 ($^{14}C$). For another example, hydrogen can be replaced by heavy hydrogen to form a deuterated drug, and the bond formed by deuterium and carbon atoms is stronger than the bond formed by ordinary hydrogen and carbon atoms. Compared with undeuterated drugs, deuterated drugs have advantages such as reduced side effects, increased drug stability, enhanced efficacy and prolonged biological half-life. All isotopic variations of the compound of the present disclosure, whether radioactive or not, are encompassed within the scope of the present disclosure. "Optional" or "optionally" means that the subsequent event or condition may occur but not requisite, that the term includes the instance in which the event or condition occurs and the instance in which the event or condition does not occur.

The term "substituted" means one or more than one hydrogen atoms on a specific atom are substituted with a substituent, including deuterium and hydrogen variants, as long as the valence of the specific atom is normal and the substituted compound is stable. When the substituent is an oxo (i.e., =O), it means two hydrogen atoms are substituted. Positions on an aromatic ring cannot be substituted with an oxo group. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two Rs, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When a variable is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When an enumerative linking group does not indicate the direction for linking, the direction for linking is arbitrary, for example, the linking group L contained in

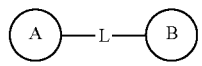

is -M-W—, then -M-W— can link ring A and ring B to form

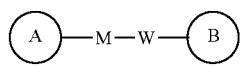

in the direction same as left-to-right reading order, and form

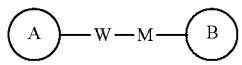

in the direction contrary to left-to-right reading order. A combination of substituents and/or variants thereof is allowed only when such combination can result in a stable compound.

Unless otherwise specified, the term "hetero" represents a heteroatom or a heteroatomic group (e.g., an atomic group containing a heteroatom), including the atom except for carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$— and optionally substituted —C(=O)N(H)—, —N(H)—, —C(=NH)—, —S(=O)$_2$N(H)— or —S(=O)N(H)—.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a monocyclic system, and also includes bicyclic and polycyclic systems, e.g., a spiro ring, a fused ring or a bridged ring. The number of the atom on the ring is usually defined as the member of the ring, for example, a "5-7 membered ring" means that 5 to 7 atoms are arranged on the ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl" includes pyridyl and piperidinyl, but excluding phenyl. The term "ring" also includes a ring system containing at least one ring, wherein each ring independently meets the above definition.

Unless otherwise specified, the term "alkyl" refers to a linear chain or branched chain saturated hydrocarbon group. In some embodiments, the alkyl is $C_{1-12}$ alkyl; in some other embodiments, the alkyl is $C_{1-6}$ alkyl; in some other embodiments, the alkyl is $C_{1-3}$ alkyl. It can be mono-substituted (e.g., —CH$_2$F) or multi-substituted (e.g., —CF$_3$), can be monovalent (e.g. methyl), divalent (e.g., methylene) or multivalent (e.g., methylidyne). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and hexyl and the like.

Unless otherwise specified, the term "heteroalkyl", by itself or in combination with another term, refers to a stable linear or branched chain alkyl or a combination thereof having a specified number of carbon atoms and at least one heteroatom or heteroatomic group. In some embodiments, the heteroatom is selected from the group consisting of B, O, N and S, wherein the nitrogen and sulfur atoms are optionally oxidized and the nitrogen atom is optionally quaternized. In some other embodiments, the heteroatomic group is selected from the group consisting of —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in some other embodiments, the heteroalkyl is $C_{1-3}$ heteroalkyl. The heteroatom or heteroatomic group can be located at any interior position of the heteroalkyl, including the position where the alkyl attaches to the rest of the molecule. But the terms "alkoxy", "alkylamino" and "alkylthio" (or thioalkoxy) are used in their conventional meanings and refer to an alkyl group connected to the rest of the molecule via an oxygen atom, an amino or a sulfur atom respectively. Examples of the heteroalkyl include, but not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$—S(=O)—CH$_3$, —CH$_2$—CH$_2$—S(=O)$_2$—CH$_3$, —CH=CHO—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, "cycloalkyl" includes any stable cyclic alkyl including monocyclic, bicyclic, or tricyclic systems, wherein the bicyclic and tricyclic systems include spiro, fused, and bridged rings. In some embodiments, the cycloalkyl is $C_{3-8}$ cycloalkyl; in some other embodiments, the cycloalkyl is $C_{3-6}$ cycloalkyl; in some other embodiments, the cycloalkyl is $C_{5-6}$ cycloalkyl. It can be mono-substituted or multi-substituted, and can be monovalent, divalent or multivalent. Examples of the cycloalkyl include, but not limited to, cyclopropyl, cyclobutyl, cyclopentyl, cyclohexyl, cycloheptyl, norbornanyl, [2.2.2]bicyclooctane, [4.4.0]bicyclodecane and the like.

Unless otherwise specified, "cycloalkenyl" includes any stable cyclic alkenyl having one or more than one unsaturated carbon-carbon double bond at any position of the group, including monocyclic, bicyclic, or tricyclic systems, wherein the bicyclic and tricyclic systems include spiro, fused, and bridged rings, but any ring in these systems is non-aromatic. In some embodiments, the cycloalkenyl is $C_{3-8}$ cycloalkenyl; in some other embodiments, the cycloalkenyl is $C_{3-6}$ cycloalkenyl; in some other embodiments, the cycloalkenyl is $C_{5-6}$ cycloalkenyl. It can be mono-substituted or multi-substituted, and can be monovalent, divalent or multivalent. Examples of the cycloalkenyl include, but not limited to, cyclopentenyl, cyclohexenyl and the like.

Unless otherwise specified, "cycloalkynyl" includes any stable cyclic alkynyl having one or more than one carbon-carbon triple bonds at any position of the group, including monocyclic, bicyclic, or tricyclic systems, wherein the bicyclic and tricyclic systems include spiro, fused, and bridged rings. It can be mono-substituted or multi-substituted, and can be monovalent, divalent or multivalent.

Unless otherwise specified, the term "heterocycloalkyl", by itself or in combination with another term, refers to a cyclized "heteroalkyl", including monocyclic, bicyclic, or tricyclic systems, wherein the bicyclic and tricyclic systems include spiro, fused, and bridged rings. In addition, in terms of the "heterocycloalkyl", the heteroatom can occupy the position through which the heterocycloalkyl is attached to the remainder of the molecule. In some embodiments, the heterocycloalkyl is a 4-6 membered heterocycloalkyl; in some other embodiments, the heterocycloalkyl is a 5-6 membered heterocycloalkyl. Examples of the heterocycloalkyl include, but not limited to, azetidinyl, oxetanyl, thiacyclobutanyl, pyrrolidinyl, pyrazolidinyl, imidazolidinyl, tetrahydrothiophenyl (including tetrahydrothiophen-2-yl and tetrahydrothiophen-3-yl etc.), tetrahydrofuranyl (including tetrahydrofuran-2-yl etc.), tetrahydropyranyl, piperidinyl (including 1-piperidinyl, 2-piperidinyl and 3-piperidinyl etc.), piperazinyl (including 1-piperazinyl and 2-piperazinyl etc.), morpholinyl (including 3-morpholinyl and 4-morpholinyl etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

"Alkoxy" refers to an alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of the alkoxy include, but not limited to methoxy, ethoxy, n-propoxy, isopropoxy, n-butoxy, sec-butoxy, tert-butoxy, n-pentyloxy and S-pentoxy.

Unless otherwise specified, the terms "aromatic ring" and "aryl" in the present disclosure can be used interchangeably. The term "aromatic ring" or "aryl" refers to a polyunsaturated carbocyclic system, which can be monocyclic, bicyclic or polycyclic systems, in which at least one ring is aromatic, and the rings in the bicyclic and polycyclic systems are fused together. It can also be mono- or poly-substituted, and can be monovalent, divalent or polyvalent. In some embodiments, the aryl is $C_{6-12}$ aryl; in some other embodiments, the aryl is $C_{6-10}$ aryl. Examples of the aryl include, but not limited to, phenyl, naphthyl (including 1-naphthyl, 2-naphthyl, etc.). The substituent of any one of the above aryl ring systems is selected from the acceptable substituents described in the present disclosure.

Unless otherwise specified, the terms "heteroaromatic ring" and "heteroaryl" in the disclosure can be used interchangeably. The term "heteroaryl" refers to an aryl (or an aromatic ring) containing 1, 2, 3 or 4 heteroatoms independently selected from the group consisting of B, N, O and S, which can be monocyclic, bicyclic, or tricyclic systems, wherein the nitrogen atom can be substituted or unsubstituted (i.e., N or NR, wherein R is H or the substituent as defined herein), and optionally quaternized and the nitrogen and sulfur heteroatoms can optionally be oxidized (i.e., NO and $S(O)_p$, p is 1 or 2). The heteroaryl can be connected to the rest of the molecule via a heteroatom. In some embodiments, the heteroaryl is a 5-10 membered heteroaryl; in some other embodiments, the heteroaryl is a 5-6 membered heteroaryl. Examples of the heteroaryl include, but not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thiophenyl (including 2-thiophenyl and 3-thiophenyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), quinolinyl (including 3-quinolinyl and 6-quinolinyl, etc.), pyrazinyl, purinyl, benzoxazolyl. The substituent of any heteroaryl ring system is selected from the acceptable substituents of the present disclosure.

Unless otherwise specified, the term "aralkyl" is intended to include those groups in which an aryl is attached to an alkyl. In some embodiments, the aralkyl is $C_{6-10}$ aryl-$C_{1-4}$ alkyl; in some other embodiments, the aralkyl is $C_{6-10}$ aryl-$C_{1-2}$ alkyl. Examples of the aralkyl include, but not limited to, benzyl, phenethyl, naphthylmethyl, and the like.

"Aryloxy" and "arylthio" represent those groups in which a carbon atom (such as methyl) in the aralkyl group is replaced with an oxygen atom or a sulfur atom, respectively. In some embodiments, the aryloxy is $C_{6-10}$ aryl-O—$C_{1-2}$ alkyl; in some other embodiments, the aryloxy is $C_{6-10}$ aryl-$C_{1-2}$ alkyl-O—. In some embodiments, the arylthio is $C_{6-10}$ aryl-S—$C_{1-2}$ alkyl; in some other embodiments, the arylthio is $C_{6-10}$ aryl-$C_{1-2}$ alkyl-S—. Examples of the aryloxy and the arylthio include, but not limited to, phenoxymethyl, 3-(1-naphthyloxy)propyl, phenylthiomethyl, and the like.

Unless otherwise specified, the term "heteroaralkyl" is intended to include those groups in which a heteroaryl is attached to an alkyl. In some embodiments, the heteroaralkyl is 5-8 membered heteroaryl-$C_{1-4}$ alkyl; in some other embodiments, the heteroaralkyl is 5-6 membered heteroaryl-$C_{1-2}$ alkyl. Examples of the heteroaralkyl include, but not limited to, pyrrolylmethyl, pyrazolylmethyl, pyridylmethyl, pyrimidinylmethyl, and the like. "Heteroaryloxy" and "heteroarylthio" refer to those groups in which a carbon atom (such as methyl) in the heteroalkyl is replaced with an oxygen atom and a sulfur atom, respectively. In some embodiments, the heteroaryloxy is 5-8 membered heteroaryl-O—$C_{1-2}$ alkyl; in some other embodiments, the heteroaryloxy is 5-6 membered heteroaryl-$C_{1-2}$ alkyl-O—. In some embodiments, the heteroarylthio group is 5-8 membered heteroaryl-S—$C_{1-2}$ alkyl; in some other embodiments, the heteroarylthio group is 5-6 membered heteroaryl-$C_{1-2}$ alkyl-S—. Examples of the heteroaryloxy and the heteroarylthio include, but not limited to, pyrrolyloxymethyl, pyrazolyloxymethyl, 2-pyridyloxymethyl, pyrrolylthiomethyl, pyrazolylthiomethyl, 2-pyridylthiomethyl, and the like.

Unless otherwise specified, $C_{n-n+m}$ or $C_n$-$C_{n+m}$ includes any specific case having n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range between n and n+m, for example, $C_1$. 12 includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$ and the like; similarly, n-membered to n+m-membered means that the number of atoms arranged on the ring is n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring and 12-membered ring, and also includes any range between n and n+m, for example, 3- to 12-membered ring includes 3- to 6-membered ring, 3- to 9-membered ring, 5- to 6-membered ring, 5- to 7-membered ring, 6- to 7-membered ring, 6- to 8-membered ring, 6- to 10-membered ring and the like.

The term "leaving group" refers to a functional group or atom which can be replaced with another functional group or atom through a substitution reaction (such as nucleophilic substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but not limited to "amino protecting group", "hydroxy protecting group" or "thiol protecting group". The term "amino protecting group" refers to a protecting group suitable for blocking the side reaction on the nitrogen atom of an amino group. Representative amino protecting groups include, but not limited to, formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis- (4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on a hydroxy group. Representative hydroxy protecting groups include, but not limited to, alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyldimethylsilyl (TBS) and the like.

The compound of the present disclosure can be prepared by a variety of synthetic methods well known to those skilled in the art, including the following enumerative embodiments, embodiments formed by the following enumerative embodiments in combination with other chemical synthesis methods and equivalent replacements well known to those skilled in the art. The preferred embodiments includes, but not limited to the embodiments of the present disclosure.

All of the solvents used in the present disclosure are commercially available. The present disclosure adopts the abbreviating words as follows: "aq" refers to water; "HATU" refers to 0-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is an amine protecting group; "BOC" refers to tert-butoxycarbonyl, which is an amine protecting group; "HOAc" refers to acetic acid; "NaCNBH$_3$" refers to sodium cyanoborohydride; "r.t." refers to room temperature; "O/N" refers to overnight; "TF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers top-toluenesulfonic acid; "NFSI" refers to N-fluoro-N-(phenylsulfonyl)benzenesulfonamide; "n-Bu$_4$NF" refers to tetrabutylammonium fluoride; "iPrOH" refers to 2-propanol; "mp" refers to melting point; "LDA" refers to lithium diisopropylamide; "Pd(dba)$_2$" refers to tris(dibenzylideneacetone)dipalladium; "Xantphos" refers to 4,5-bis(diphenylphosphino)-9,9-dimethylxanthene; "Pd(dppf)Cl$_2$" refers to [1,1'-bis(diphenylphosphino)ferrocene] dichloropalladium; "Pd$_2$(dba)$_3$" refers to tris(dibenzylideneacetone)dipalladium; "Xphos" refers to 2-dicyclohexylphosphorus-2,4,6-triisopropylbiphenyl.

Compounds are named manually or by ChemDraw® software, and the commercially available compounds use their vendor directory names.

Figure 1:
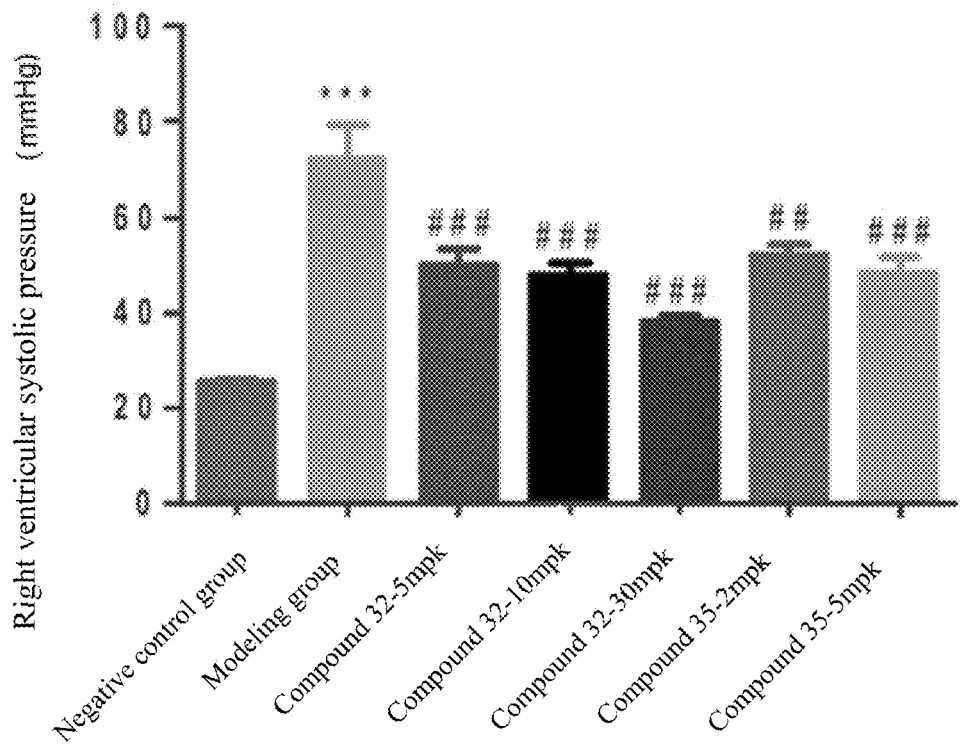
FIG. 1 shows the effect of the compound of the present disclosure on the mean right ventricle systolic pressure (mRVSP) in the rat model of MCT (monocrotaline)-induced pulmonary arterial hypertension.

***p<0.001 vs sham; #p<0.05, ##p<0.01, ###p<0.001 vs MCT, one-way analysis of variance (one-way ANOVA).

The statistical analysis result P<0.05 is considered to be a significant difference, indicated by * and #; P<0.01 is considered to be a greatly significant difference, indicated by ** and ##; P<0.001 is considered to be an extremely significant difference, indicated by * ** and ###.

DETAILED DESCRIPTION OF THE PREFERRED EMBODIMENT

The following embodiments further illustrate the present disclosure, but the present disclosure is not limited thereto. The present disclosure has been described in detail herein, and specific embodiments thereof have also been disclosed. It will be apparent to those skilled in the art that various changes and modifications can be made to the specific embodiments of the present disclosure without departing from the spirit and scope of the present disclosure.

Intermediate I1

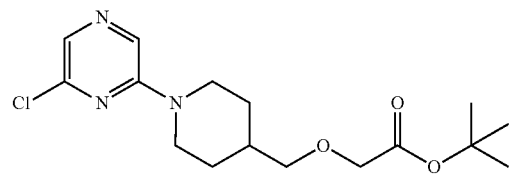 [SMILES: CC(C)(C)OC(=O)COCC1CCN(c2cncc(Cl)n2)CC1]

Synthetic Route:

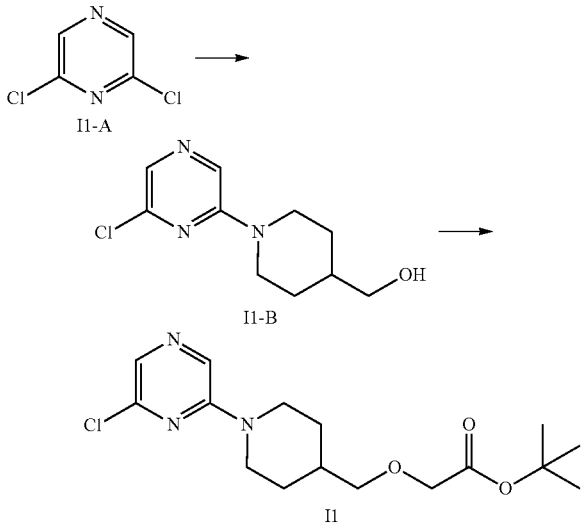

Step 1: Synthesis of Compound I1-B

To dioxane (60.00 mL) were added compound I1-A (3 g, 20.14 mmol), piperidinemethanol (2.44 g, 21.14 mmol) and triethylamine (2.24 g, 22.15 mmol, 3.08 mL) and the mixture was mixed uniformly, and the reaction solution was stirred at 105° C. for 2 hours. After the completion of the reaction, the solvent was removed under reduced pressure, and the obtained residue was separated by column chromatography (developing solvent: petroleum ether/ethyl acetate=10/1 to 3/1) to obtain I1-B.

MS m/z: 227.9 [M+H]⁺.

Step 2: Synthesis of Compound I1

Compound I1-B (3 g, 13.18 mmol) and tetrabutylammonium hydrogen sulfate (4.47 g, 13.18 mmol) were dissolved in toluene (60.00 mL), and the temperature was cooled to 0° C. and the mixture was stirred for 10 minutes. After to the reaction solution was added 40% potassium hydroxide solution (60 mL) and the reaction solution was stirred for 20 minutes, to the reaction solution was added tert-butyl bromoacetate (7.71 g, 39.53 mmol, 5.84 mL) and the reaction solution was stirred at 30° C. for 12 hours. The reaction solution was poured into water (20 mL) and extracted with ethyl acetate (30 mL). The separated organic phase was washed with saturated brine (20 mL) and dried over anhydrous sodium sulfate. After the anhydrous sodium sulfate was removed by filtration, the solvent was removed under reduced pressure, and the obtained residue was separated by column chromatography (developing solvent: ethyl acetate/petroleum ether=1/4) to obtain the target compound I1.

MS m/z: 342.0 [M+H]⁺.

$^1$H NMR (400 MHz, CHLOROFORM-d) δ ppm 8.89 (s, 1H), 7.66 (s, 1H), 3.88 (s, 2H), 3.34-3.32 (d, J=6 Hz, 2H), 2.89-2.82 (m, 2H), 1.89-1.82 (m, 2H), 1.41 (s, 9H), 1.26-1.16 (m, 2H).

Intermediate I2

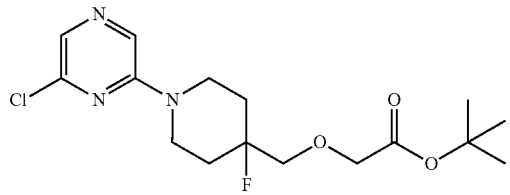 [SMILES: CC(C)(C)OC(=O)COCC1(F)CCN(c2cncc(Cl)n2)CC1]

Synthetic Route:

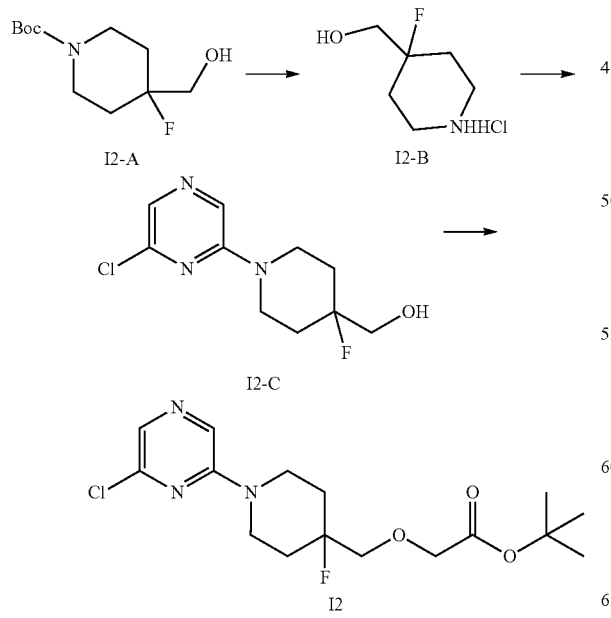

Step 1: Synthesis of Compound I2-B

Compound I2-A (2 g, 8.57 mmol) was mixed uniformly with ethyl acetate hydrochloride (10.00 mL), and the mixture was stirred at 20° C. for 0.5 hour. After the completion of the reaction, the reaction solution was filtered to obtain I2-B.

Step 2: Synthesis of Compound I2-C

Except for using the corresponding raw materials, compound I2-C was prepared according to the same method as that of compound I1-B which is comprised in the process of intermediate I1.

Step 2: Synthesis of Compound I2

Except for using the corresponding raw materials, compound I2 was prepared according to the same method as that of compound I1 which is comprised in the process of intermediate I1.

MS m/z: 360.0 [M+H]⁺.

$^1$H NMR (400 MHz, METHANOL-d$_4$) δ ppm 8.16 (s, 1H), 7.74 (s, 1H), 4.24 (brd, J=13.6 Hz, 2H), 4.07 (s, 2H), 3.63 (d, J=19.2 Hz, 2H), 3.37 (d, J=3.0 Hz, 1H), 3.30 (d, J=3.0 Hz, 1H), 2.04-1.73 (m, 4H), 1.50 (s, 9H).

Embodiment 1: Compound 1

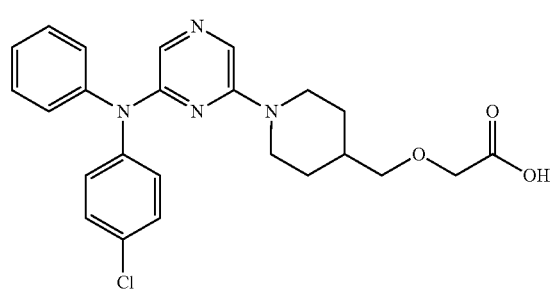 [SMILES: O=C(O)COCC1CCN(c2cncc(N(c3ccccc3)c3ccc(Cl)cc3)n2)CC1]

Synthetic Route:

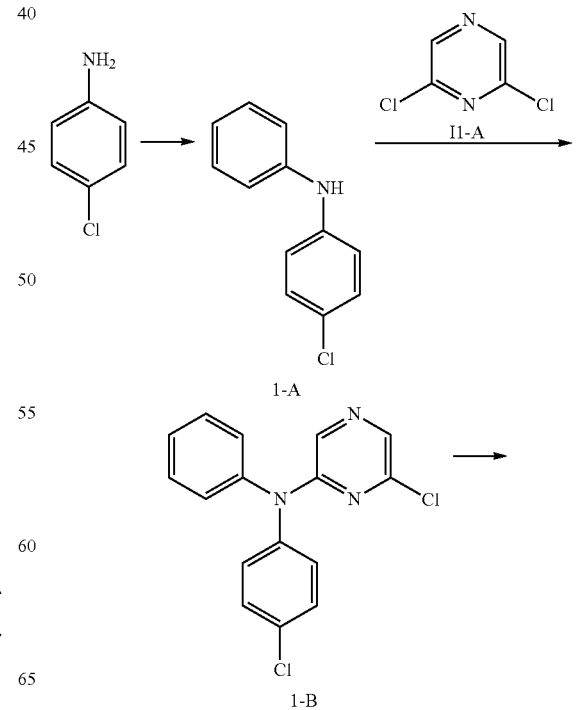

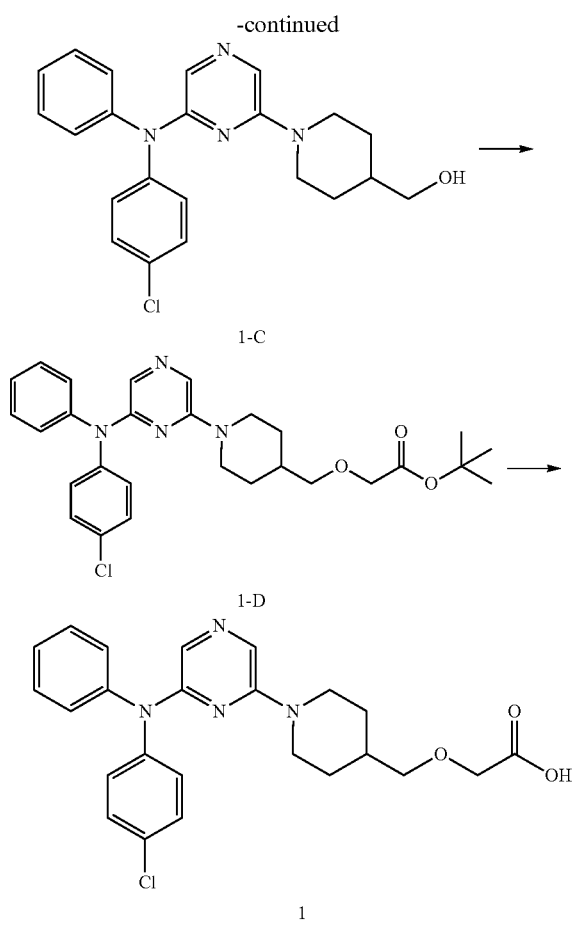

Step 1: Synthesis of Compound I-A

4-Chloroaniline (36 g, 282.19 mmol), bromobenzene (50 g, 318.46 mmol, 33.56 mL), Pd(dppf)Cl$_2$·CH$_2$Cl$_2$ (6.91 g, 8.47 mmol) and sodium tert-butoxide (54.24 g, 564.39 mmol) were mixed uniformly with toluene (300 mL), and the reaction solution was stirred at 120° C. for 2 hours under nitrogen protection. The reaction solution was filtered, and the filtrate was concentrated under reduced pressure to obtain a crude product. The crude product was separated by column chromatography (developing solvent: petroleum ether/ethyl acetate=10/1) to obtain 1-A.

$^1$H NMR (400 MHz, CDCl$_3$) δ ppm 7.22-7.19 (m, 2H), 7.14-7.12 (m, 2H), 6.98 (m, 2H), 6.96-6.90 (m, 3H), 5.59 (s, 1H).

Step 2: Synthesis of Compound I-B

To a solution of 1-A (1.5 g, 7.36 mmol) in N',N-dimethylformamide (30.00 mL) were added I1-A (1.32 g, 8.83 mmol), cesium carbonate (7.20 g, 22.08) at 20° C. mmol). After the completion of the addition, the reaction solution was stirred at 110° C. for 14 hours. The reaction solution was cooled to room temperature, and was added with water (50 mL) and stirred for 2 minutes, and then was extracted with ethyl acetate (50 mL*2). The combined organic phase was washed with brine (30 mL*2), dried over anhydrous sodium sulfate, filtered, and the filtrate was concentrated to obtain a crude product. The crude product was separated by chromatography silica gel column (petroleum ether/ethyl acetate=I/O to 80/1) to obtain 1-B.

H NMR: $^1$H NMR (400 MHz, CHLOROFORM-d) δ ppm 7.17 (m, 2H), 7.24 (m, 2H), 7.30-7.36 (m, 3H), 7.42 (m, 2H), 7.92 (s, 1H), 8.01 (s, 1H).

Step 3: Synthesis of Compound I-C

To a solution of compound 1-B (500.00 mg, 1.58 mmol) in 1,4-dioxane (5.00 mL) were added 4-piperidinemethanol (273.19 mg, 2.37 mmol), Pd(dba)$_2$ (90.93 mg, 158.14 µmol), Xantphos (91.50 mg, 158.14 µmol) and cesium carbonate (1.29 g, 3.95 mmol) at 20° C. After the completion of the addition, the reaction solution was stirred at 100° C. for 15 hours under an atmosphere of nitrogen. The reaction solution was concentrated under reduced pressure, and to the concentrate was added water (20 mL) and the mixture was stirred for 2 minutes. And then the mixture was extracted with ethyl acetate (20 mL*2), and the combined organic phase was washed with brine (30 mL). The organic phase was dried over anhydrous sodium sulfate, filtered, and the filtrate was concentrated to obtain a crude product. The crude product was separated by chromatography silica gel column (petroleum ether/ethyl acetate=1/1 to 0/1) to obtain 1-C.

$^1$H NMR (400 MHz, CHLOROFORM-d) δ ppm 1.24-1.28 (m, 3H), 1.70 (m, 2H), 3.50 (d, J=6.0 Hz, 2H), 3.66-4.10 (m, 4H), 7.14-7.45 (m, 9H), 7.80 (s, 2H).

Step 4: Synthesis of Compound I-D

To a solution of compound 1-C (80.00 mg, 202.58 µmol) in toluene (6.00 mL) was added tetrabutylammonium hydrogen sulfate (68.78 mg, 202.5 µmol) at 20° C. After the completion of the addition, the solution was cooled to 0° C. and stirred for 10 minutes. Then, to the solution was added 40% potassium hydroxide (3.00 mL), and the reaction solution was further stirred at 0° C. for 20 minutes. And then to the solution was added tert-butyl bromoacetate (118.54 mg, 607.75 µmol, 89.80 µL) dropwise, and after the completion of the addition, the reaction solution was stirred at 30° C. for 11.5 hours. The reaction solution was diluted with water (20 mL), and then extracted with ethyl acetate (30 mL*2). The combined organic phase was washed with brine (30 mL), dried over anhydrous sodium sulfate, filtered, and the filtrate was concentrated to obtain a crude product. The crude product was separated by a preparative silica gel plate (petroleum ether/ethyl acetate=1/1) to obtain 1-D.

MS m/z: 509.2 [M+H]$^+$.

Step 5: Synthesis of Compound I

To a solution of compound 1-D (80.00 mg, 157.16 µmol) in methanol (8.00 mL) was added 10% sodium hydroxide (2.00 mL) at 20° C., and after the completion of the addition, the solution was stirred at 45° C. for 0.5 hour. The reaction solution was concentrated under reduced pressure to obtain a concentrate, and then the concentrate was diluted with water (20 mL), adjusted the pH to 5 with hydrochloric acid (2N), and then extracted with ethyl acetate (30 mL*2). The combined organic phase was washed with brine (20 mL), dried over anhydrous sodium sulfate, filtered, and the filtrate was concentrated to obtain a crude product. The crude product was separated by preparative HPLC (neutral) to obtain compound 1.

MS m/z: 453.0 [M+H]$^+$.

$^1$H NMR (400 MHz, DMSO-d) δ ppm 1.09-1.12 (m, 2H), 1.24-1.29 (m., 2H), 1.64 (m, 2H), 1.78 (s, 1H), 2.75 (t, J=12.0 Hz, 2H), 3.84 (s, 2H), 4.06 (m, 2H), 7.06 (s, 1H), 7.17-7.24 (m, 5H), 7.38-7.41 (m, 4H), 7.74 (s, 1H).

Embodiment 2: Compound 2

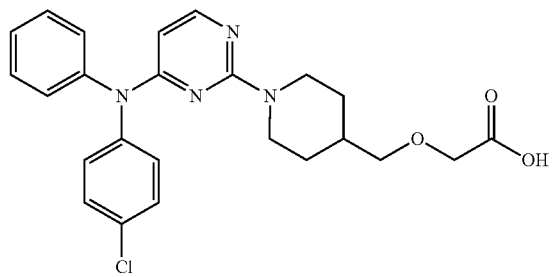 [SMILES: O=C(O)COCC1CCN(c2nccc(N(c3ccccc3)c3ccc(Cl)cc3)n2)CC1]

Synthetic Route:

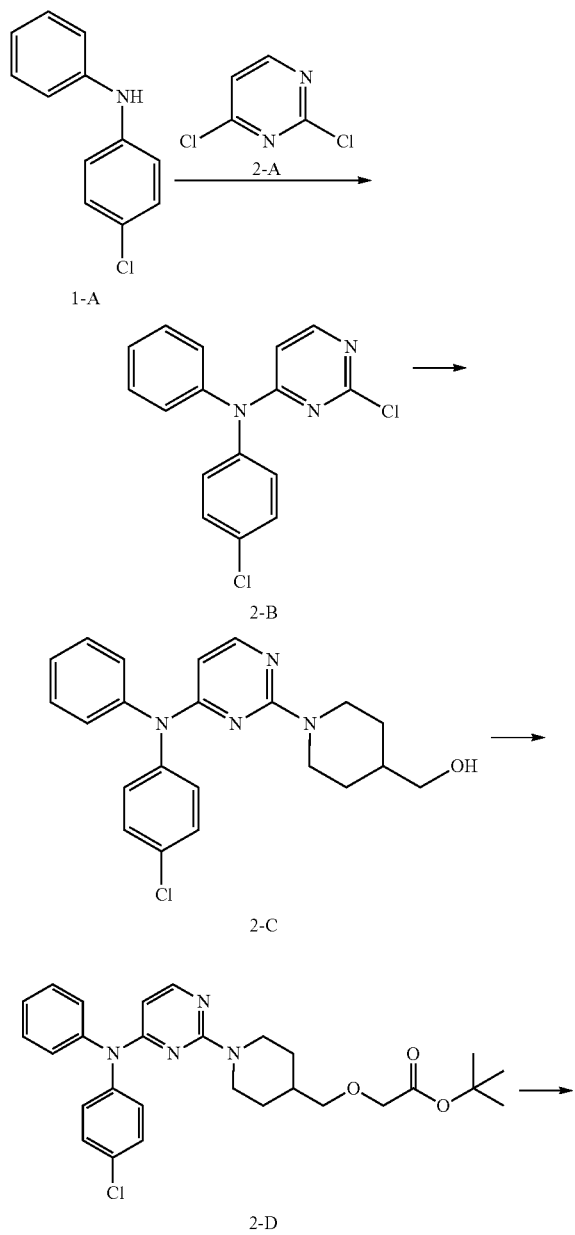

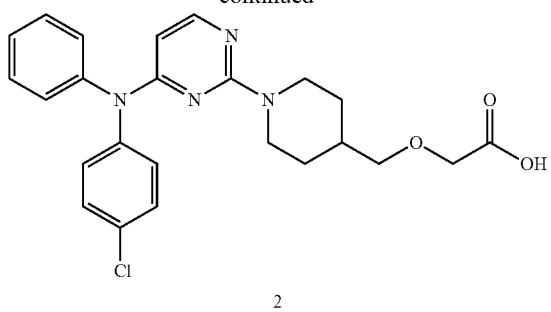

Step 1: Synthesis of Compound 2-B

Except for using the corresponding raw materials, compound 2-B was prepared according to the same method as that of compound 1-B in the process of embodiment 1.

$^1$H NMR (400 MHz, CHLOROFORM-d) δ ppm 6.29 (d, J=6.0 Hz, 1H), 7.11-7.18 (m, 5H), 7.25-7.37 (m, 4H), 7.99 (d, J=6.0 Hz, 1H).

Step 2: Synthesis of Compound 2-C

Except for using the corresponding raw materials, compound 2-C was prepared according to the same method as that of compound 1-C in the process of embodiment 1.

$^1$H NMR (400 MHz, CHLOROFORM-d) δ ppm 1.04-1.12 (m., 2H), 1.64-1.67 (m, 3H), 2.64-2.70 (m, 2H), 3.43-3.42 (m, 2H), 4.46-4.49 (m, 2H), 5.66 (m, 1H), 7.11-7.29 (m, 9H), 7.86 (m, 2H).

Step 3: Synthesis of Compound 2-D

Except for using the corresponding raw materials, compound 2-D was prepared according to the same method as that of compound 1-D in the process of embodiment 1.

MS m/z: 509.2 [M+H]$^+$.

Step 4: Synthesis of Compound 2

Except for using the corresponding raw materials, compound 2 was prepared according to the same method as that of compound 1 in the process of embodiment 1.

MS m/z: 453.0 [M+H]$^+$.

$^1$H NMR (400 MHz, DMSO-d) δ ppm 0.98-1.08 (m, 2H), 1.59-1.62 (m, 2H), 1.76 (s, 1H), 2.67-2.73 (m, 2H), 3.28 (d, J=6.4 Hz, 2H), 3.88 (s, 2H), 4.36-4.39 (m, 2H), 5.59 (d, J=6.0 Hz, 1H), 7.27-7.30 (m, 5H), 7.41-7.45 (m, 4H), 7.91 (d, J=5.6 Hz, 1H).

Embodiment 3: Compound 3

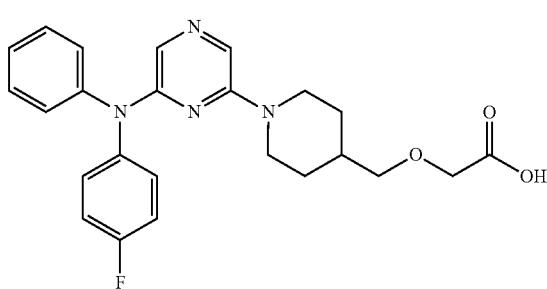 [SMILES: O=C(O)COCC1CCN(c2cncc(N(c3ccccc3)c3ccc(F)cc3)n2)CC1]

Synthetic Route:

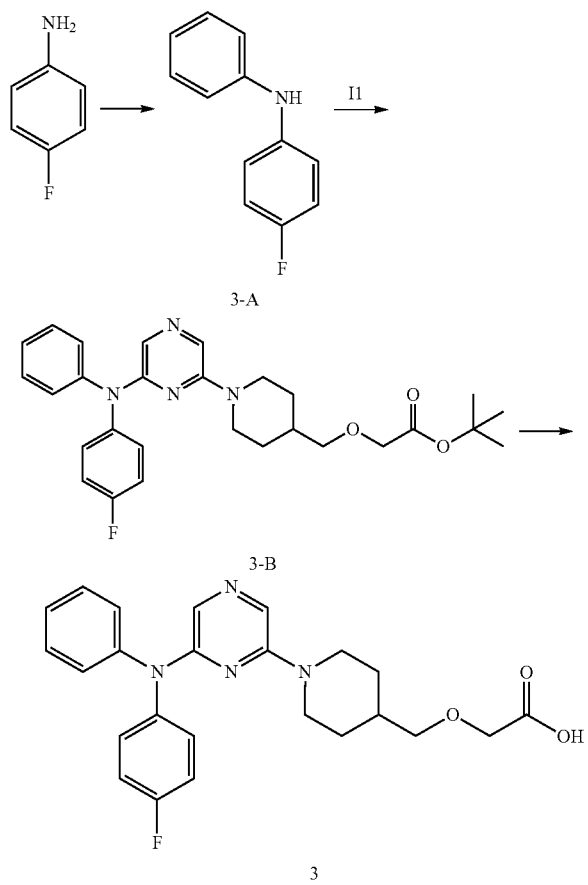

Step 1: Synthesis of Compound 3-A

Except for using the corresponding raw materials, compound 3-A was prepared according to the same method as that of compound 1-A in the process of embodiment 1.

Step 2: Synthesis of Compound 3-B

To a solution of compound 3-A (54.77 mg, 292.54 μmol) in dioxane (10 mL) were added compound I1 (0.1 g, 292.54 μmol), cesium carbonate (285.95 mg, 877.62 mol), xantphos (33.85 mg, 58.51 μmol)) and Pd(dba)$_2$ (16.82 mg, 29.25 μmol), and the reaction system was stirred at 100° C. for 12 hours under nitrogen protection. The reaction system was diluted with water (20 mL) and extracted with ethyl acetate (10 mL*3). The combined organic phase was washed with saturated brine (20 mL) and dried over anhydrous sodium sulfate, filtered and the filtrate was concentrated to obtain a crude product. The crude product was separated by preparative thin layer chromatography (petroleum ether/tetrahydrofuran=2/1) to obtain 3-B.

MS m/z: 493.2 [M+H]$^+$.

Step 3: Synthesis of Compound 3

To a solution of compound 3-B in methanol (10 mL) was added 10% sodium hydroxide (8 mL), and the reaction system was stirred at 45° C. for 0.5 hour. The reaction solution was concentrated, diluted with water (20 mL) and stirred for 2 minutes, and the reaction system was adjusted the pH to 5 with diluted hydrochloric acid (2N), and extracted with ethyl acetate (30 mL*2). The combined organic phase was washed with saturated brine (20 mL), dried over anhydrous sodium sulfate, filtered, and the filtrate was concentrated under vacuum to obtain a crude product. The crude product was separated by HPLC (neutral) to obtain compound 3.

$^1$H NMR (400 MHz, CHLOROFORM-d) δ ppm 7.60 (s, 1H), 7.38-7.32 (m, 2H), 7.26 (s, 1H), 7.24-7.17 (m, 5H), 7.04 (t, J=8.4 Hz, 2H), 4.15-4.07 (m, 4H), 3.43 (brd, J=6.4 Hz, 2H), 2.78 (brt, J=12.0 Hz, 2H), 1.79 (brd, J=12.8 Hz, 2H), 1.25 (brd, J=10.0 Hz, 3H).

MS m/z: 437.0 [M+H]$^+$.

Embodiment 4: Compound 4

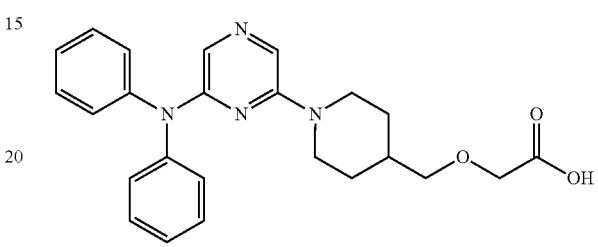

Synthetic Route:

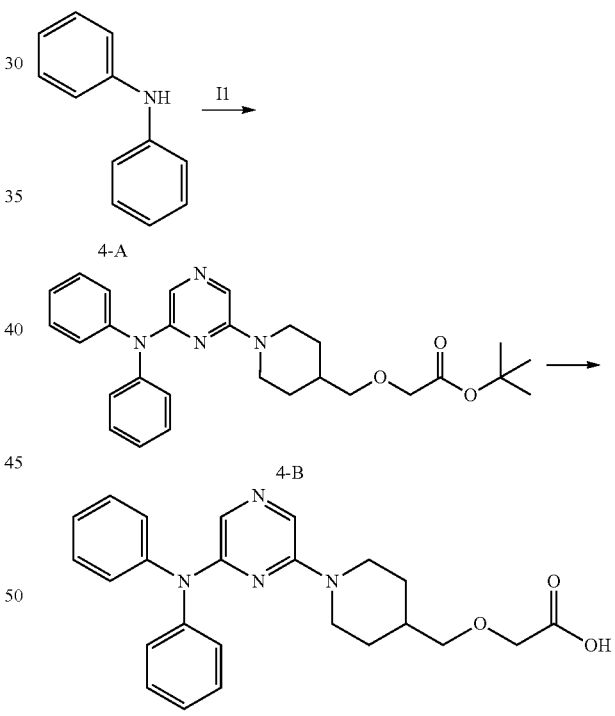

Step 1: Synthesis of Compound 4-B

Except for using the corresponding raw materials, compound 4-B was prepared according to the same method as that of compound 3-B in the process of embodiment 3.

MS m/z: 475.2 [M+H]$^+$.

Step 2: Synthesis of Compound 4

Except for using the corresponding raw materials, compound 4 was prepared according to the same method as that of compound 3 in the process of embodiment 3.

MS m/z: 419.2 [M+H]$^+$.

¹H NMR (400 MHz, METHANOL-d₄) δ ppm 7.54 (s, 1H), 7.34-7.41 (m, 4H), 7.17-7.25 (m, 6H), 7.06 (s, 1H), 4.16 (brd, J=13.04 Hz, 2H), 3.90 (s, 2H), 3.36 (d, J=6.28 Hz, 2H), 2.73-2.85 (m, 2H), 1.83-1.97 (m, 1H), 1.77 (brd, J=11.80 Hz, 2H), 1.20 (qd, J=12.38, 4.04 Hz, 2H).

Embodiment 5: Compound 5

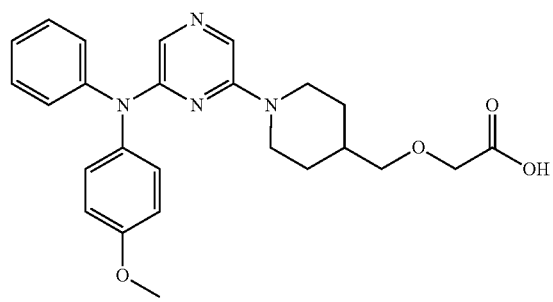 [SMILES: COc1ccc(N(c2ccccc2)c2cncc(N3CCC(COCC(=O)O)CC3)n2)cc1]

Synthetic Route:

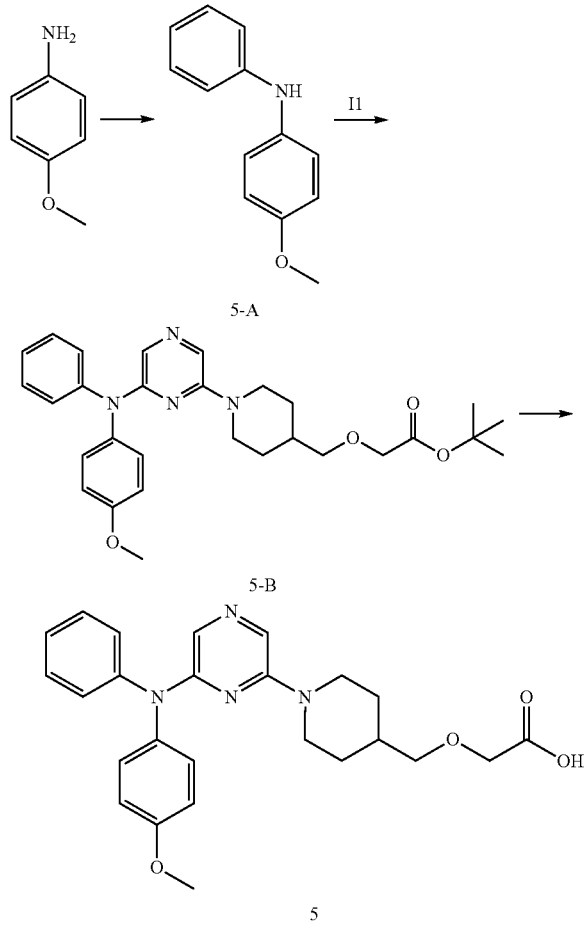

Step 1: Synthesis of Compound 5-A

Except for using the corresponding raw materials, compound 5-A was prepared according to the same method as that of compound 1-A in the process of embodiment 1.

Step 2: Synthesis of Compound 5-B

Except for using the corresponding raw materials, compound 5-B was prepared according to the same method as that of compound 3-B in the process of embodiment 3.

MS m/z: 505.2 [M+H]⁺.

Step 3: Synthesis of Compound 5

Except for using the corresponding raw materials, compound 5 was prepared according to the same method as that of compound 3 in the process of embodiment 3.

MS m/z: 449.1 [M+H]⁺.

¹H NMR (400 MHz, METHANOL-d₄) δ ppm 7.50 (s, 1H), 7.30-7.37 (m, 2H), 7.19-7.25 (m, 2H), 7.12-7.19 (m, 3H), 6.94-7.01 (m, 3H), 4.16 (brd, J=13.04 Hz, 2H), 3.89 (s, 2H), 3.83 (s, 3H), 3.35 (d, J=6.52 Hz, 2H), 2.73-2.84 (m, 2H), 1.83-1.96 (m, 1H), 1.77 (brd, J=11.28 Hz, 2H), 1.19 (qd, J=12.32, 3.96 Hz, 2H).

Embodiment 6: Compound 6

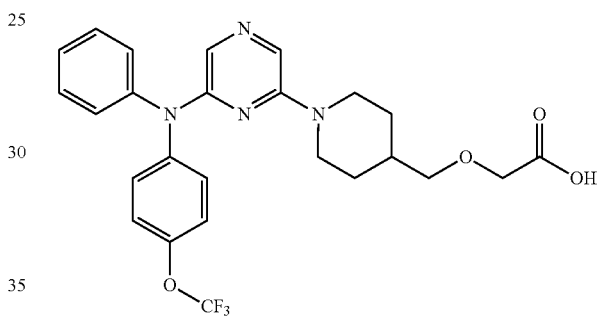

Synthetic Route:

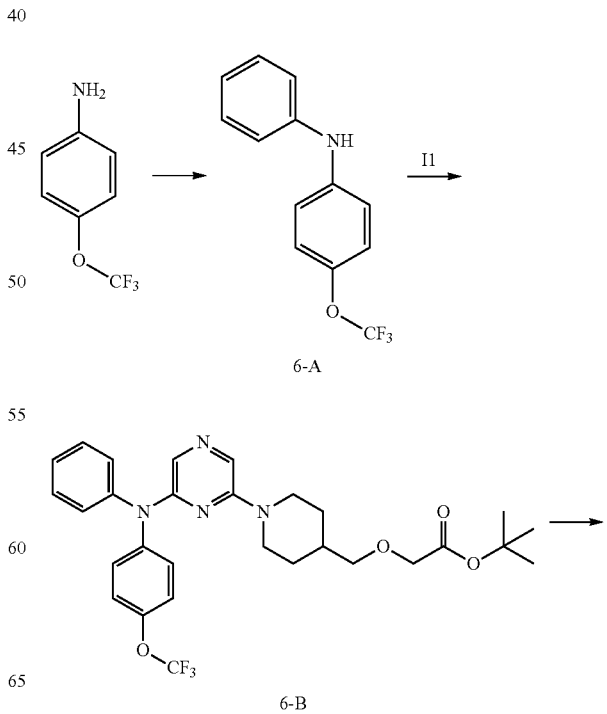

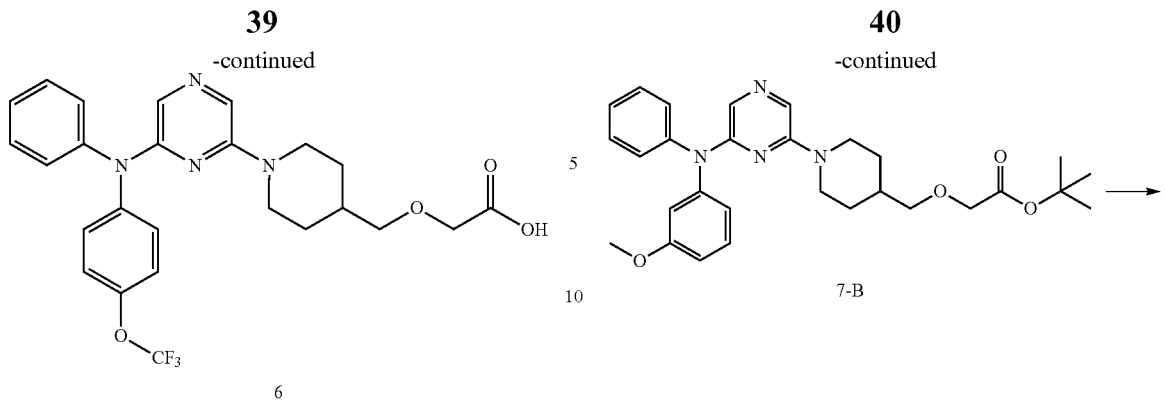

Step 1: Synthesis of Compound 6-A

Except for using the corresponding raw materials, compound 6-A was prepared according to the same method as that of compound 1-A in the process of embodiment 1.

Step 2: Synthesis of Compound 6-B

Except for using the corresponding raw materials, compound 6-B was prepared according to the same method as that of compound 3-B in the process of embodiment 3.

MS m/z: 559.1 [M+H]$^+$.

Step 3: Synthesis of Compound 6

Except for using the corresponding raw materials, compound 6 was prepared according to the same method as that of compound 3 in the process of embodiment 3.

MS m/z: 503.1 [M+H]$^+$.

$^1$H NMR (400 MHz, METHANOL-d$_4$) δ ppm 7.60 (s, 1H), 7.39-7.47 (m, 2H), 7.22-7.32 (m, 7H), 7.08 (s, 1H), 4.16 (brd, J=13.04 Hz, 2H), 3.95 (s, 2H), 3.37 (d, J=6.52 Hz, 2H), 2.75-2.86 (m, 2H), 1.84-1.98 (m, 1H), 1.77 (brd, J=11.56 Hz, 2H), 1.21 (qd, J=12.40, 3.88 Hz, 2H).

Embodiment 7: Compound 7

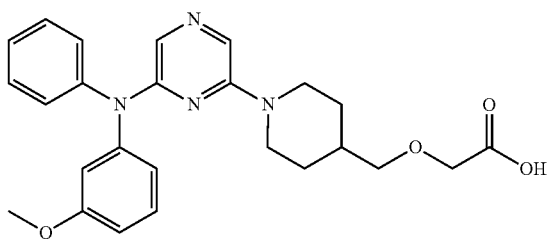 [SMILES: COc1cccc(N(c2ccccc2)c2cncc(N3CCC(COCC(=O)O)CC3)n2)c1]

Step 1: Synthesis of Compound 7-A

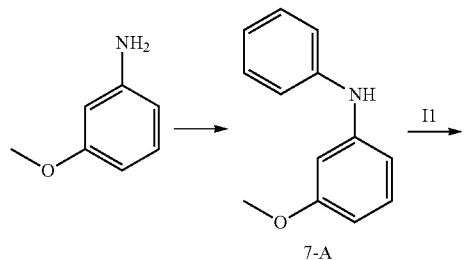

Except for using the corresponding raw materials, compound 7-A was prepared according to the same method as that of compound 1-A in the process of embodiment 1.

Step 2: Synthesis of Compound 7-B

Except for using the corresponding raw materials, compound 7-B was prepared according to the same method as that of compound 3-B in the process of embodiment 3.

MS m/z: 505.2 [M+H]$^+$.

Step 3: Synthesis of Compound 7

Except for using the corresponding raw materials, compound 7 was prepared according to the same method as that of compound 3 in the process of embodiment 3.

MS m/z: 449.1 [M+H]$^+$.

$^1$H NMR (400 MHz, METHANOL-d$_4$) δ ppm 7.55 (s, 1H), 7.35-7.41 (m, 2H), 7.27 (brt, J=8.28 Hz, 1H), 7.18-7.24 (m, 3H), 7.06 (s, 1H), 6.76-6.81 (m, 3H), 4.17 (brd, J=13.04 Hz, 2H), 3.85 (s, 2H), 3.76 (s, 3H), 3.36 (brs, 2H), 2.80 (brt, J=11.80 Hz, 2H), 1.91 (brs, 1H), 1.78 (brd, J=12.04 Hz, 2H), 1.27-1.37 (m, 2H), 1.11-1.25 (m, 2H).

Embodiment 8: Compound 8

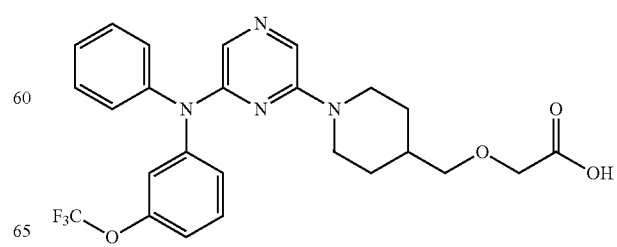

Synthetic Route:

Step 1: Synthesis of Compound 8-A

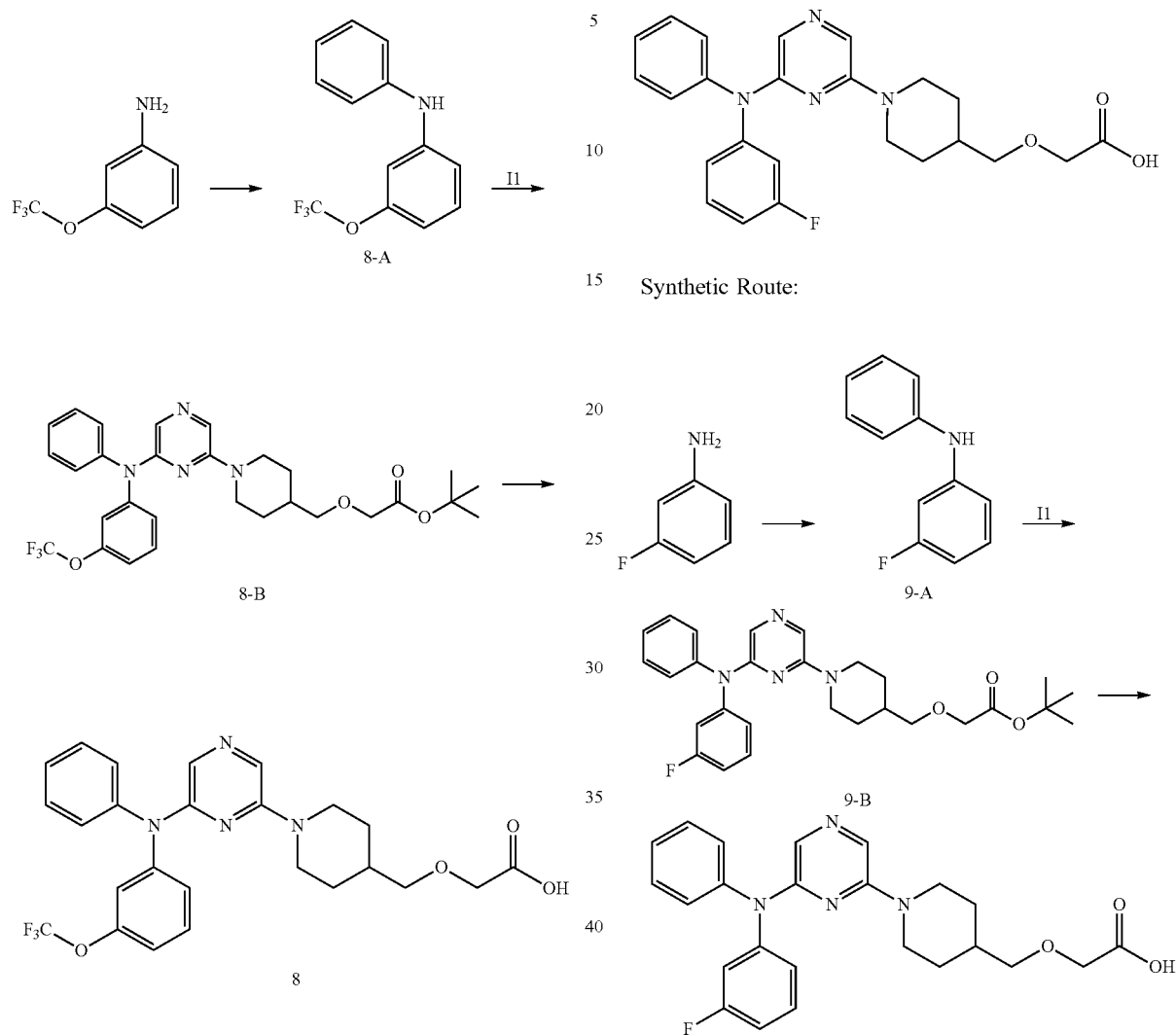

Except for using the corresponding raw materials, compound 8-A was prepared according to the same method as that of compound 1-A in the process of embodiment 1.

Step 2: Synthesis of Compound 8-B

Except for using the corresponding raw materials, compound 8-B was prepared according to the same method as that of compound 3-B in the process of embodiment 3.

MS m/z: 559.1 [M+H]$^+$.

Step 3: Synthesis of Compound 8

Except for using the corresponding raw materials, compound 8 was prepared according to the same method as that of compound 3 in the process of embodiment 3.

MS m/z: 503.1 [M+H]$^+$.

$^1$H NMR (400 MHz, METHANOL-d$_4$) δ ppm 7.63 (s, 1H), 7.43-7.50 (m, 2H), 7.40 (t, J=8.40 Hz, 1H), 7.29-7.35 (m, 1H), 7.24-7.28 (m, 2H), 7.11-7.16 (m, 2H), 7.06 (s, 1H), 7.04 (brd, J=8.52 Hz, 1H), 4.19 (brd, J=13.32 Hz, 2H), 3.86 (s, 2H), 3.35 (d, J=6.52 Hz, 2H), 2.77-2.87 (m, 2H), 1.92 (brd, J=3.52 Hz, 1H), 1.80 (brd, J=13.80 Hz, 2H), 1.31 (brt, J=7.28 Hz, 1H), 1.21 (qd, J=12.32, 3.88 Hz, 2H).

Embodiment 9: Compound 9

Synthetic Route:

Step 1: Synthesis of Compound 9-A

Except for using the corresponding raw materials, compound 9-A was prepared according to the same method as that of compound 1-A in the process of embodiment 1.

Step 2: Synthesis of Compound 9-B

Except for using the corresponding raw materials, compound 9-B was prepared according to the same method as that of compound 3-B in the process of embodiment 3.

MS m/z: 493.2 [M+H]$^+$.

Step 3: Synthesis of Compound 9

Except for using the corresponding raw materials, compound 9 was prepared according to the same method as that of compound 3 in the process of embodiment 3.

MS m/z: 437.0 [M+H]$^+$.

$^1$H NMR (400 MHz, CHLOROFORM-d) δ ppm 7.55 (s, 1H), 7.34-7.24 (m, 2H), 7.18-7.08 (m, 3H), 6.87 (brd, J=8.0 Hz, 2H), 6.79-6.68 (m, 1H), 4.11-3.97 (m, 3H), 3.35 (brd, J=6.4 Hz, 2H), 2.71 (brt, J=11.2 Hz, 2H), 1.71 (brd, J=12.4 Hz, 1H), 1.25-1.09 (m, 4H).

Embodiment 10: Compound 10

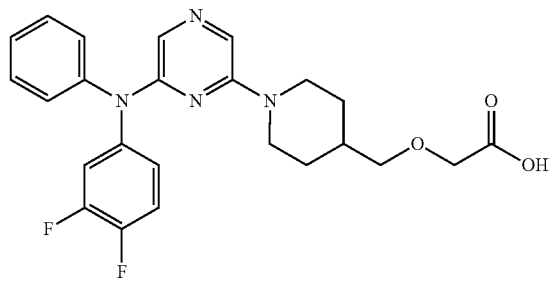 [SMILES: O=C(O)COCC1CCN(c2cncc(N(c3ccccc3)c3ccc(F)c(F)c3)n2)CC1]

Synthetic Route:
Step 1: Synthesis of Compound 10-A

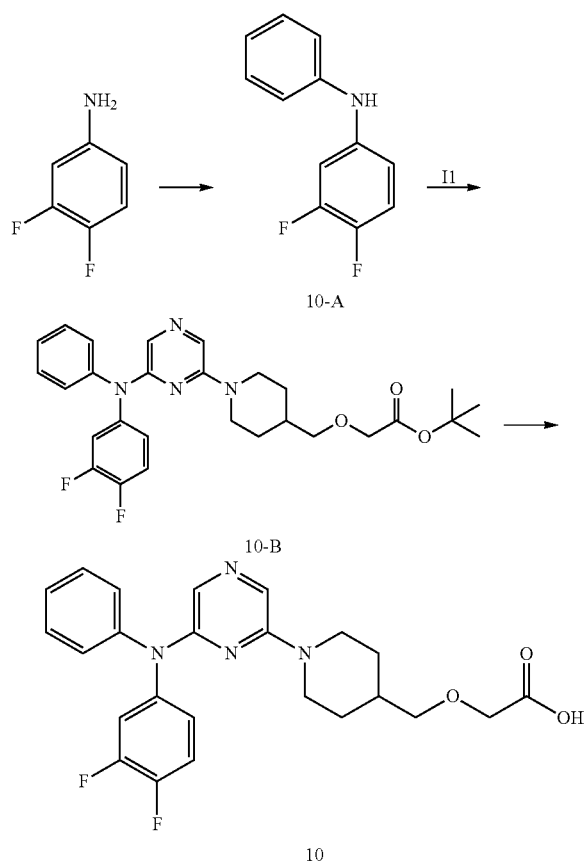

Except for using the corresponding raw materials, compound 10-A was prepared according to the same method as that of compound 1-A in the process of embodiment 1.

Step 2: Synthesis of Compound 10-B

Except for using the corresponding raw materials, compound 10-B was prepared according to the same method as that of compound 3-B in the process of embodiment 3.

MS m/z: 511.2 [M+H]$^+$.

Step 3: Synthesis of Compound 10

Except for using the corresponding raw materials, compound 10 was prepared according to the same method as that of compound 3 in the process of embodiment 3.

MS m/z: 455.0 [M+H]$^+$.

$^1$H NMR (400 MHz, CHLOROFORM-d) δ ppm 7.62 (s, 1H), 7.41-7.33 (m, 2H), 7.26-7.18 (m, 4H), 7.13-7.03 (m, 2H), 6.89 (brd, J=9.2 Hz, 1H), 4.12 (brd, J=13.2 Hz, 2H), 4.02 (brs, 2H), 3.39 (brd, J=6.6 Hz, 2H), 2.78 (brt, J=12.4 Hz, 2H), 1.90 (brs, 1H), 1.78 (brd, J=11.8 Hz, 2H), 1.29-1.14 (m, 2H).

Embodiment 11: Compound 11

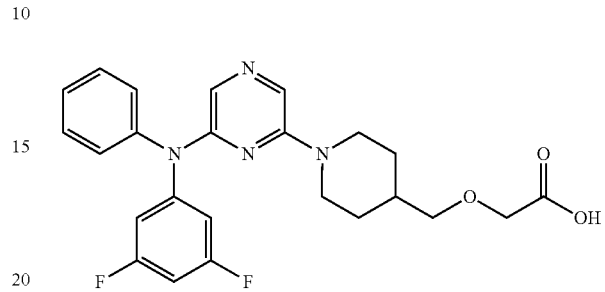

Synthetic Route:
Step 1: Synthesis of Compound 11-A

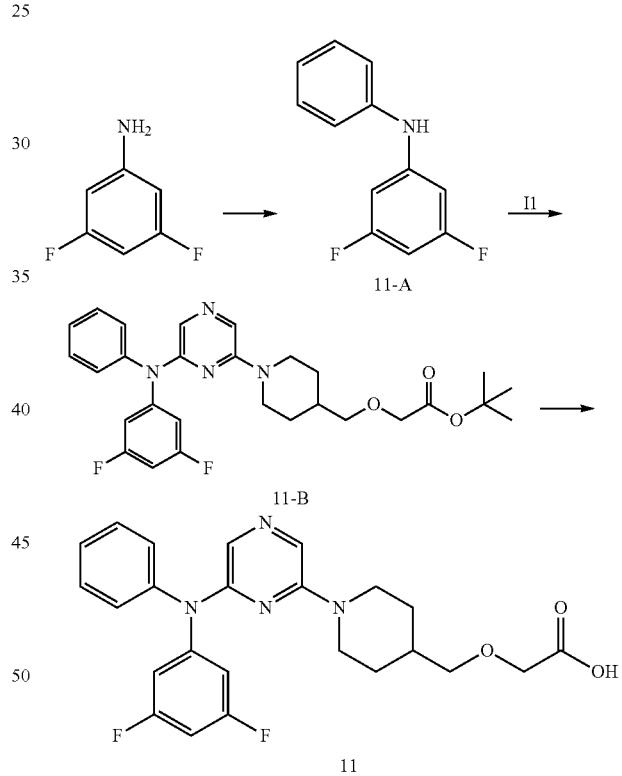

Except for using the corresponding raw materials, compound 11-A was prepared according to the same method as that of compound 1-A in the process of embodiment 1.

Step 2: Synthesis of Compound 11-B

Except for using the corresponding raw materials, compound 11-B was prepared according to the same method as that of compound 3-B in the process of embodiment 3.

MS m/z: 511.2 [M+H]$^+$.

Step 3: Synthesis of Compound 11

Except for using the corresponding raw materials, compound 11 was prepared according to the same method as that of compound 3 in the process of embodiment 3.

$^1$H NMR (400 MHz, CHLOROFORM-d) δ ppm 7.60 (s, 1H), 7.42-7.27 (m, 2H), 7.24-7.17 (m, 2H), 7.17-7.10 (m, 2H), 6.68-6.56 (m, 2H), 6.54-6.33 (m, 1H), 4.09 (brd, J=13.6 Hz, 2H), 4.05-3.97 (m, 3H), 3.34 (s, 2H), 2.76 (brt, J=11.8 Hz, 2H), 1.85 (brd, J=4.0 Hz, 1H), 1.74 (brd, J=12.4 Hz, 2H), 1.25-1.09 (m, 2H).

Embodiment 12: Compound 12

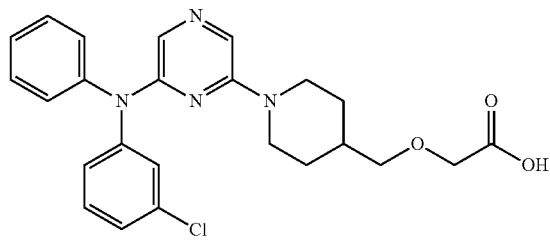 [SMILES: O=C(O)COCC1CCN(c2cncc(N(c3ccccc3)c3cccc(Cl)c3)n2)CC1]

Synthetic Route:

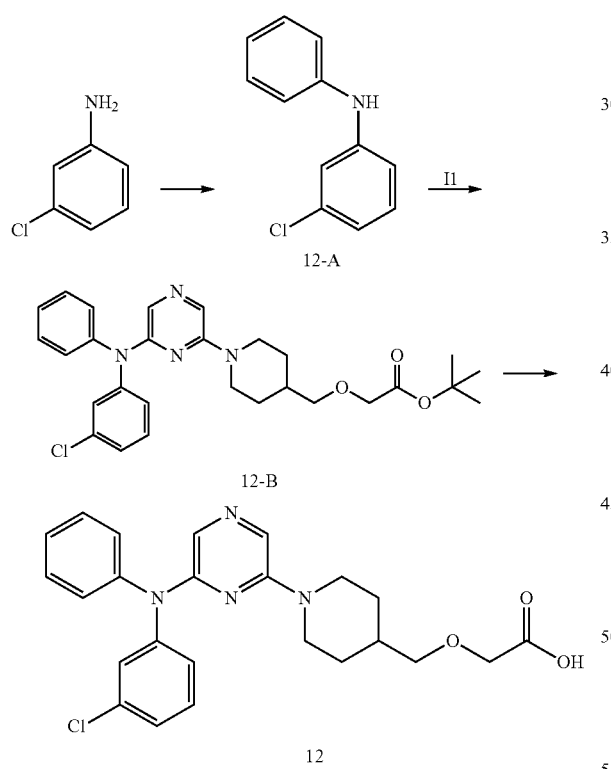

Step 1: Synthesis of Compound 12-A

Except for using the corresponding raw materials, compound 12-A was prepared according to the same method as that of compound 1-A in the process of embodiment 1.

Step 2: Synthesis of Compound 12-B

Except for using the corresponding raw materials, compound 12-B was prepared according to the same method as that of compound 3-B in the process of embodiment 3.

MS m/z: 509.1 [M+H]$^+$.

Step 3: Synthesis of Compound 12

Except for using the corresponding raw materials, compound 12 was prepared according to the same method as that of compound 3 in the process of embodiment 3.

MS m/z: 453.0 [M+H]$^+$.

$^1$H NMR (400 MHz, CHLOROFORM-d) δ ppm 7.56 (s, 1H), 7.49-7.23 (m, 5H), 7.19-7.09 (m, 5H), 7.03-6.92 (m, 2H), 4.06 (brd, J=12.0 Hz, 2H), 4.00 (s, 2H), 3.35 (brd, J=6.0 Hz, 2H), 2.72 (brt, J=12.0 Hz, 2H), 1.83 (brs, 1H), 1.72 (brd, J=12.4 Hz, 2H), 1.23-1.11 (m, 2H).

Embodiment 13: Compound 13

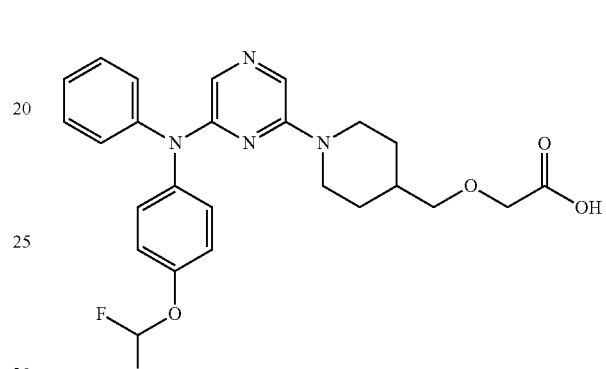

Synthetic Route:

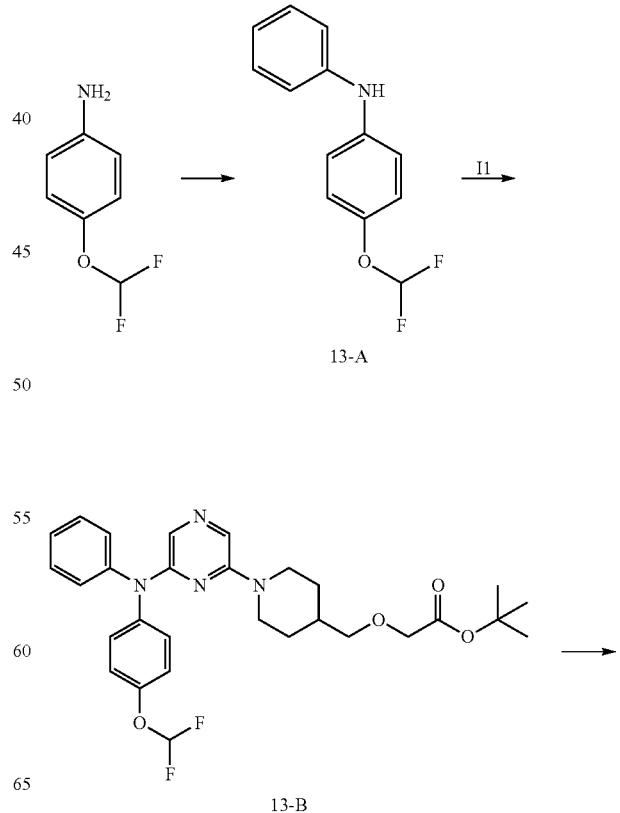

Step 1: Synthesis of Compound 13-A

To a solution of p-difluoromethoxyaniline (1 g, 6.28 mmol, 781.25 L) in dimethylformamide (30.00 mL) were added phenylboronic acid (766.21 mg, 6.28 mmol, 980.39 μL), pyridine (994.14 mg, 12.57 mmol, 1.01 mL) and copper acetate (1.14 g, 6.28 mmol), and the reaction mixture was stirred at 20 to 25° C. for 12 hours under an atmosphere of oxygen (15 Psi). The reaction system was diluted with 30 mL water and extracted with ethyl acetate (30 mL*3). The combined organic phase was washed with saturated brine (20 mL) and dried over anhydrous sodium sulfate. After the anhydrous sodium sulfate was filtered off, the solvent was removed under reduced pressure to obtain a crude product. The crude product was purified by column chromatography (petroleum ether/ethyl acetate=20/1) to obtain compound 13-A.

$^1$H NMR (400 MHz, CHLOROFORM-d) δ ppm 7.20-7.16 (m, 2H), 6.95-6.93 (m, 6H), 6.87-6.84 (m, 1H), 6.54-6.16 (m, 1H).

Step 2: Synthesis of Compound 13-B

Except for using the corresponding raw materials, compound 13-B was prepared according to the same method as that of compound 3-B in the process of embodiment 3.

MS m/z: 541.1 [M+H]$^+$.

Step 3: Synthesis of Compound 13

Except for using the corresponding raw materials, compound 13 was prepared according to the same method as that of compound 3 in the process of embodiment 3.

MS m/z: 485.0 [M+H]$^+$.

$^1$H NMR (400 MHz, CHLOROFORM-d) δ ppm 7.62 (s, 1H), 7.35 (d, J=7.0 Hz, 1H), 7.31-7.16 (m, 6H), 7.10 (s, 1H), 6.74-6.31 (m, 2H), 4.11 (s, 3H), 3.44 (brd, J=6.6 Hz, 1H), 2.79 (brt, J=11.8 Hz, 2H), 2.30 (brs, 5H), 1.91 (brs, 1H), 1.79 (brd, J=13.6 Hz, 1H), 1.39-1.13 (m, 2H).

Embodiment 14: Compound 14

Step 1: Synthesis of Compound 14-A

Except for using the corresponding raw materials, compound 14-A was prepared according to the same method as that of compound 13-A in the process of embodiment 13.

Step 2: Synthesis of Compound 14-B

Except for using the corresponding raw materials, compound 14-B was prepared according to the same method as that of compound 3-B in the process of embodiment 3.

MS m/z: 541.1 [M+H]$^+$.

Step 3: Synthesis of Compound 14

Except for using the corresponding raw materials, compound 14 was prepared according to the same method as that of compound 3 in the process of embodiment 3.

MS m/z: 485.0 [M+H]$^+$.

$^1$H NMR (400 MHz, CHLOROFORM-d) δ ppm 7.55 (s, 1H), 7.39-7.25 (m, 2H), 7.24-7.03 (m, 5H), 7.01-6.85 (m, 2H), 6.79 (brd, J=8.0 Hz, 1H), 6.62-6.17 (m, 1H), 3.99 (s, 3H), 3.33 (brd, J=6.5 Hz, 2H), 3.24-2.94 (m, 3H), 2.71 (brt, J=11.6 Hz, 2H), 1.82 (brs, 1H), 1.70 (brd, J=12.6 Hz, 2H), 1.33-0.97 (m, 2H).

Embodiment 15: Compound 15

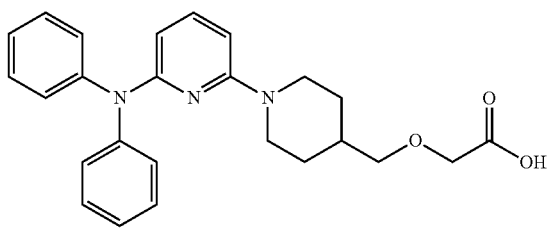 [SMILES: O=C(O)COCC1CCN(c2cccc(N(c3ccccc3)c3ccccc3)n2)CC1]

Synthetic Route:

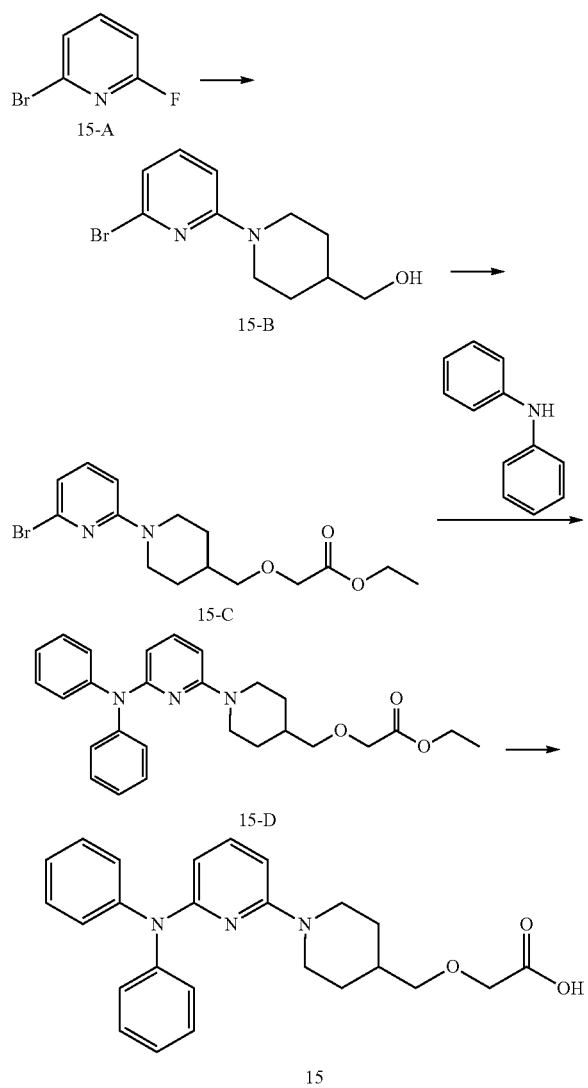

Step 1: Synthesis of Compound 15-B

To a solution of compound 15-A (1 g, 5.68 mmol) in dioxane (150 mL) were added the compound piperidinemethanol (654.44 mg, 5.68 mmol) and triethylamine (632.49 mg, 6.25 mmol, 870.00 μL), and the reaction solution was stirred at 105° C. for 2 hours. After the completion of the reaction, the solvent was removed under reduced pressure, and the obtained residue was separated by chromatography column (petroleum ether/ethyl acetate=4/1 to 1/1) to obtain the target compound 15-B.

Step 2: Synthesis of Compound 15-C

To a solution of compound 15-B (1 g, 3.69 mmol) in dichloromethane (50 mL) was added the compound rhodium acetate (81.50 mg, 368.80 μmol) at 0° C., followed by the addition of ethyl diazoacetate (420.80 mg, 3.69 mmol, 386.06 μL) dropwise, and the reaction solution was stirred at 10 to 20° C. for 12 hours after the completion of the addition. The reaction system was diluted with water (20 mL) and extracted with dichloromethane (20 mL*2). The combined dichloromethane phase was washed with saturated brine (20 mL) and dried over anhydrous sodium sulfate. After the anhydrous sodium sulfate was removed by filtration, the solvent was removed under reduced pressure, and the mixture was concentrated under vacuum to obtain a crude product.

The crude product was separated by column chromatography to obtain 15-C.

MS m/z: 356.9.1 [M+H]$^+$.

Step 3: Synthesis of Compound 15-D

Except for using the corresponding raw materials, compound 15-D was prepared according to the same method as that of compound 3-B in the process of embodiment 3.

MS m/z: 446.1 [M+H]$^+$.

Step 4: Synthesis of Compound 15

To a mixed solution of compound 15-D (0.1 g, 224.44 μmol) in tetrahydrofuran (5 mL), water (3 mL) and methanol (5 mL) was added lithium hydroxide (28.26 mg, 673.32 μmol), and the reaction solution was stirred at 20° C. to 25° C. for 0.5 hour. The reaction solution was concentrated, diluted with water (20 mL) and stirred for 2 minutes. The reaction system was adjusted the pH to 5 with diluted hydrochloric acid (2N) and extracted with ethyl acetate (30 mL*2). The organic phase was combined, washed with saturated brine (20 mL), dried over anhydrous sodium sulfate, filtered, and the filtrate was concentrated under vacuum to obtain a crude product. The crude product was separated by HPLC (neutral) to obtain 15.

MS m/z: 418.0 [M+H]$^+$.

$^1$H NMR (400 MHz, CHLOROFORM-d) δ ppm 7.23-7.19 (m, 6H), 7.15-7.11 (m, 3H), 7.03-6.98 (m, 2H), 6.06 (d, J=8.4 Hz, 1H), 5.90 (d, J=8.0 Hz, 1H), 4.03-3.99 (m, 3H), 3.35 (d, J=6.4 Hz, 2H), 2.63-2.57 (m, 2H), 1.77 (brs, 2H), 1.64 (brd, J=10.8 Hz, 2H), 1.20-1.13 (m, 2H).

Embodiment 16: Compound 16

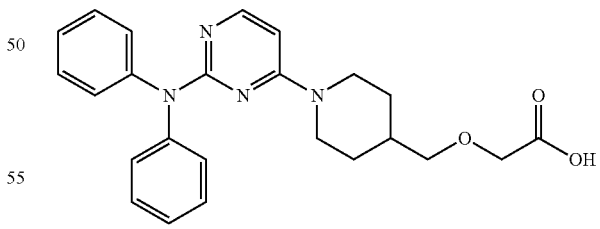

Synthetic Route:

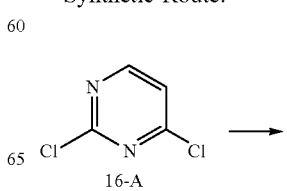

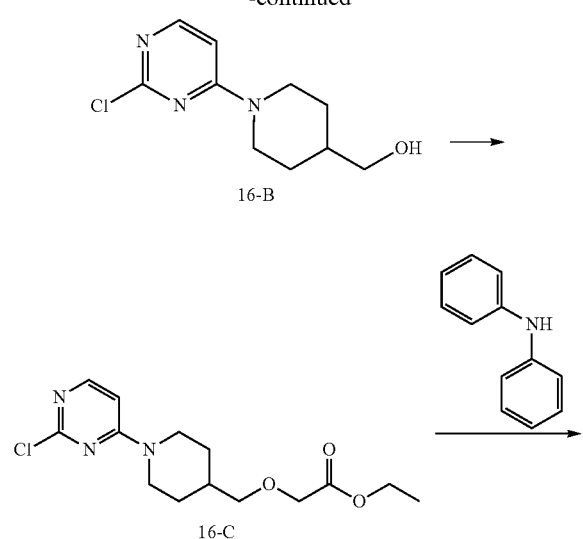

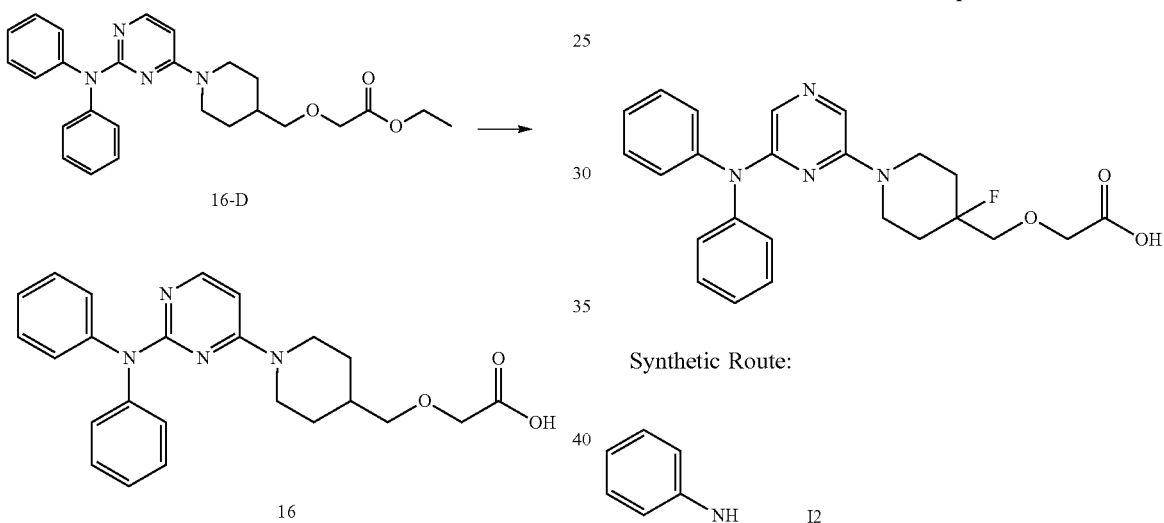

Step 1: Synthesis of Compound 16-B

Except for using the corresponding raw materials, compound 16-B was prepared according to the same method as that of compound 15-B in the process of embodiment 15.

MS m/z: 227.9 [M+H]$^+$.

$^1$H NMR (400 MHz, CHLOROFORM-d) δ ppm 7.94-7.92 (m, 1H), 6.38-6.32 (m, 1H), 4.35 (brs, 2H), 3.48-3.46 (m, 2H), 2.89-2.83 (m, 2H), 1.82-1.73 (m, 3H), 1.47 (brs, 1H), 1.19-1.15 (m, 2H).

Step 2: Synthesis of Compound 16-C

Except for using the corresponding raw materials, compound 16-C was prepared according to the same method as that of compound 15-C in the process of embodiment 15.

MS m/z: 313.9 [M+H]$^+$.

Step 3: Synthesis of Compound 16-D

Diphenylamine (296.62 mg, 1.75 mmol), 16-C (0.5 g, 1.59 mmol) and tri-tert-butylphosphine (1.29 g, 637.39 μmol) were dissolved in dioxane (10 mL), and Pd$_2$(dba)$_3$ (145.92 mg, 159.35 μmol) and cesium carbonate (1.30 g, 3.98 mmol) were added under nitrogen protection, and the reaction solution was stirred at 90° C. for 12 hours. The reaction system was diluted with water (20 mL) and extracted with ethyl acetate (40 mL). The organic phase was washed with saturated brine (20 mL) and dried over anhydrous sodium sulfate. The mixture was filtered and the filtrate was concentrated under vacuum to obtain a crude product. The crude product was purified by column chromatography (petroleum ether/tetrahydrofuran=2/1) to obtain 16-D.

MS m/z: 447.2 [M+H]$^+$.

Step 4: Synthesis of Compound 16

Except for using the corresponding raw materials, compound 16 was prepared according to the same method as that of compound 15 in the process of embodiment 15.

MS m/z: 419.1 [M+H]$^+$.

$^1$H NMR (400 MHz, METHANOL-d$_4$) δ ppm 7.74 (d, J=6.52 Hz, 1H), 7.32-7.40 (m, 4H), 7.16-7.27 (m, 6H), 6.28 (d, J=6.52 Hz, 1H), 4.21 (brd, J=13.04 Hz, 2H), 3.86 (s, 2H), 3.34 (brs, 2H), 2.80 (brt, J=12.40 Hz, 2H), 1.86-1.99 (m, 1H), 1.03-1.24 (m, 2H).

Embodiment 17: Compound 17

Synthetic Route:

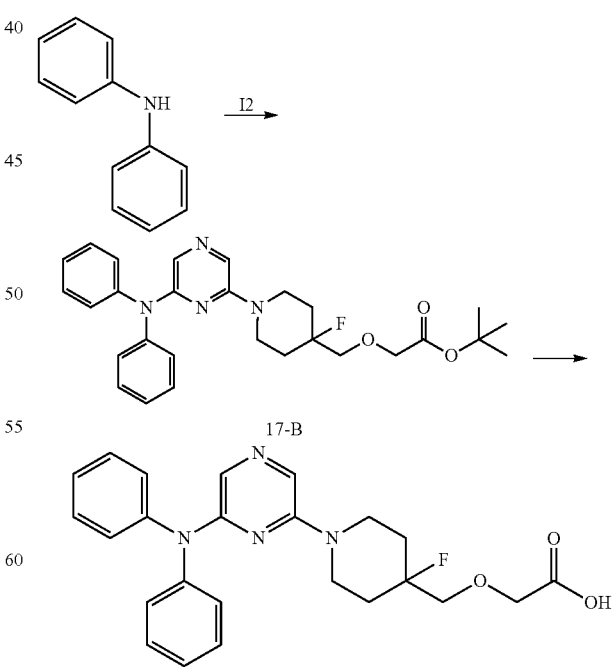

Step 1: Synthesis of Compound 17-B

Except for using the corresponding raw materials, compound 17-B was prepared according to the same method as that of compound 3-B in the process of embodiment 3.

MS m/z: 493.2 [M+H]+.

Step 2: Synthesis of Compound 17

Except for using the corresponding raw materials, compound 17 was prepared according to the same method as that of compound 3 in the process of embodiment 3.

MS m/z: 437.1 [M+H]+.

$^1$H NMR (400 MHz, METHANOL-$d_4$) δ ppm 7.61 (s, 1H), 7.35-7.43 (m, 4H). 7.18-7.25 (m, 6H), 7.11 (s, 1H), 4.12 (s, 2H), 3.97 (brd, J=13.32 Hz, 2H), 3.60 (d, J=19.32 Hz, 2H), 3.12-3.22 (m, 2H), 1.64-1.90 (m, 4H).

Embodiment 18: Compound 18

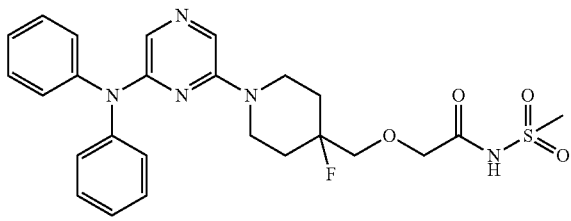 [SMILES: CS(=O)(=O)NC(=O)COCC1(F)CCN(c2cncc(N(c3ccccc3)c3ccccc3)n2)CC1]

Synthetic Route:

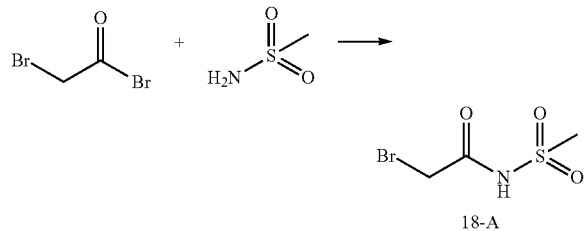

18-A

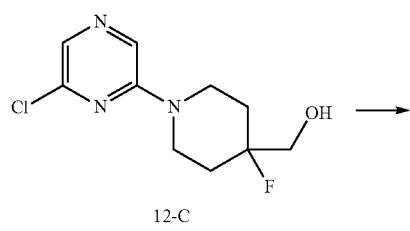

12-C

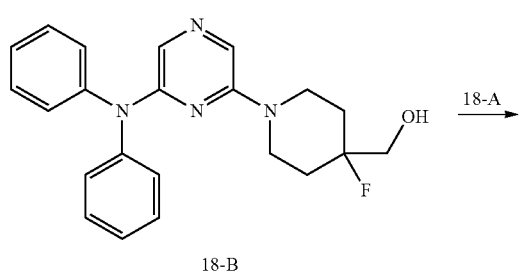

18-B

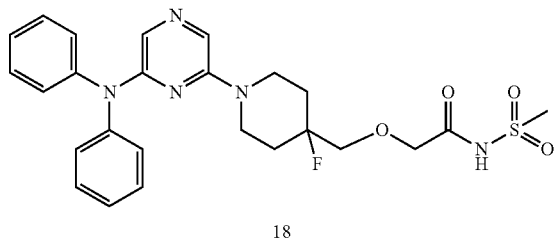

18

Step 2: Synthesis of Compound 18-A

To a solution of methanesulfonamide (20.00 g, 210.26 mmol) in toluene (300 mL) was added a solution of bromoacetyl bromide (63.66 g, 315.39 mmol, 27.44 mL) in isopropyl acetate (300 mL) dropwise. After the completion of the addition, the reaction solution was stirred at 90° C. for 12 hours. The reaction solution was concentrated. The obtained crude product was washed with dichloromethane (100 mL*2) and filtered to obtain 18-A.

$^1$H NMR (400 MHz, METHANOL-$d_4$) δ ppm 3.93 (s, 2H), 3.27 (s, 3H).

Step 2: Synthesis of Compound 18-B

Except for using the corresponding raw materials, compound 18-B was prepared according to the same method as that of compound 3-B in the process of embodiment 3.

MS m/z: 379.1 [M+H]+.

Step 3: Synthesis of Compound 18

Compound 18-B (0.3 g, 792.72 μmol), 18-A (85.63 mg, 396.36 μmol) and t-BuOK (533.72 mg, 4.76 mmol) were dissolved in dioxane (20 mL), and the reaction solution was stirred at 35° C. for 3 hours. The reaction solution was adjusted the pH to 6 to 7 with 1N hydrochloric acid solution, and extracted with dichloromethane (50 mL*2). The combined extract was washed with saturated brine (20 mL) once, dried over anhydrous sodium sulfate, filtered, and the filtrate was concentrated. The crude product was separated by preparative HPLC (neutral, acetonitrile-water) to obtain compound 18.

MS m/z: 514.2 [M+H]+.

$^1$H NMR (400 MHz, METHANOL-$d_4$) δ ppm 7.61 (s, 1H), 7.34-7.43 (m, 4H), 7.18-7.27 (m, 6H), 7.11 (s, 1H), 4.14 (s, 2H), 3.97 (brd, J=13.32 Hz, 2H), 3.62 (d, J=20.00 Hz, 2H), 3.25 (s, 3H), 3.10-3.22 (m, 2H), 1.62-1.90 (m, 4H).

Embodiment 19: Compound 19

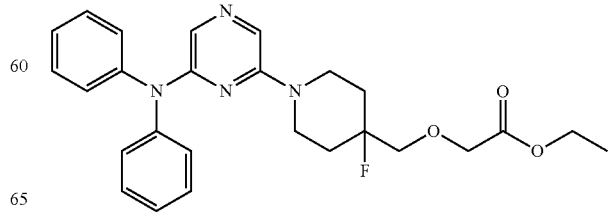

Synthetic Route:

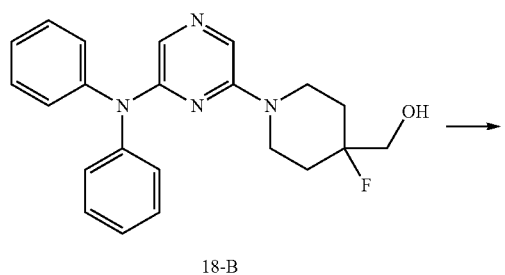
18-B

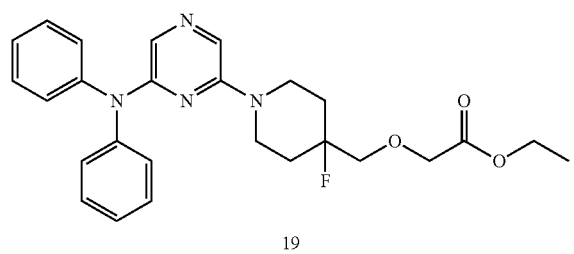
19

Step 1: Synthesis of Compound 19

Compound 18-B (0.53 g, 1.40 mmol) was dissolved in DMF (10 mL) and NaH (168.04 mg, 4.20 mmol) was added at 0° C., and the reaction solution was stirred at 60° C. for 0.5 hours, and then ethyl bromoacetate (701.64 mg, 4.20 mmol) was added, and the reaction solution was further stirred at 60° C. for 12 hours. The reaction solution was slowly added into 50 mL ethyl acetate and 20 mL water, and the ethyl acetate layer was separated, washed with saturated brine (20 mL) once, dried over anhydrous sodium sulfate, filtered, and the filtrate was concentrated. The obtained crude product was purified by column chromatography (petroleum ether/tetrahydrofuran=4/1 to 2/1) to obtain compound 19. MS m/z: 465.2 [M+H]$^+$.

$^1$H NMR (400 MHz, METHANOL-d$_4$) δ ppm 7.61 (s, 1H), 7.36-7.41 (m, 4H), 7.19-7.25 (m, 6H), 7.11 (s, 1H), 4.22 (q, J=7.04 Hz, 2H), 4.18 (s, 2H), 3.97 (brd, J=13.30 Hz, 2H), 3.60 (d, J=19.32 Hz, 2H), 3.13-3.22 (m, 2H), 1.61-1.89 (m, 4H), 1.29 (t, J=7.15 Hz, 3H).

Embodiment 20: Compound 20

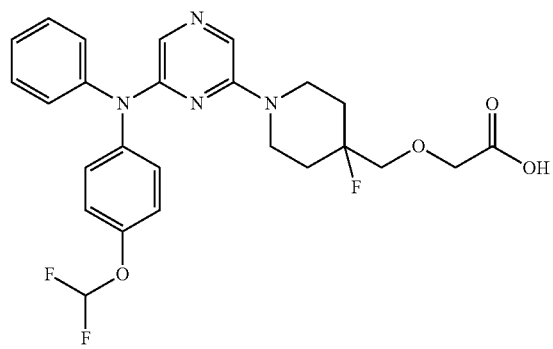

Synthetic Route:

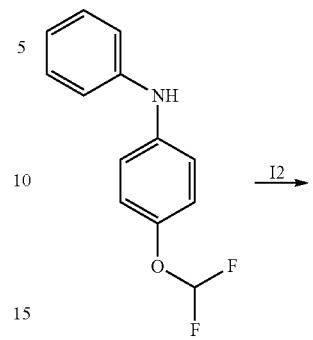
13-A

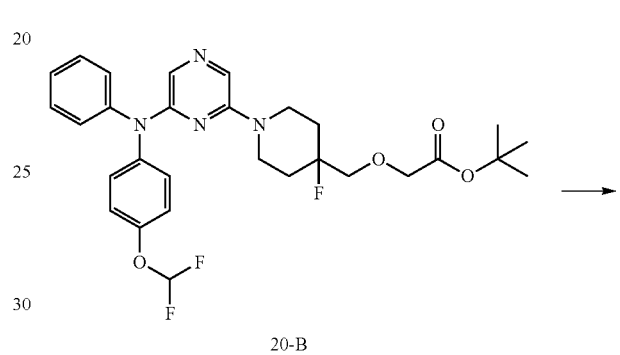
20-B

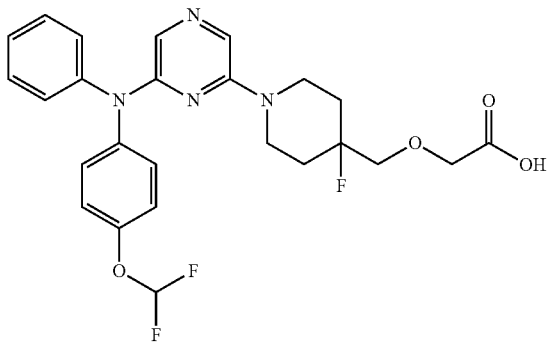
20

Step 1: Synthesis of Compound 20-B

Except for using the corresponding raw materials, compound 20-B was prepared according to the same method as that of compound 3-B in the process of embodiment 3.

MS m/z: 559.1 [M+H]$^+$.

Step 2: Synthesis of Compound 20

Except for using the corresponding raw materials, compound 20 was prepared according to the same method as that of compound 3 in the process of embodiment 3.

MS m/z: 503.0 [M+H]$^+$.

$^1$H NMR (400 MHz, METHANOL-d$_4$) δ ppm 7.47-7.41 (m, 2H), 7.35 (t, J=8.0 Hz, 1H), 7.32-7.20 (m, 3H), 7.14-6.59 (m, 4H), 4.15-3.85 (m, 4H), 3.60 (brd, J=18.0 Hz, 2H), 3.19 (brt, J=12.0 Hz, 2H), 1.99-1.59 (m, 4H).

Embodiment 21: Compound 21

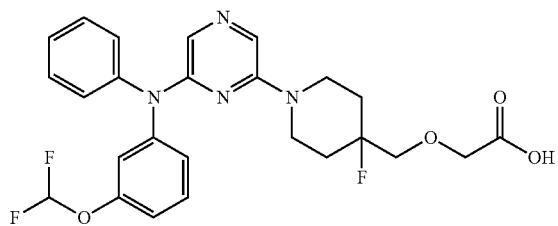

Synthetic Route:

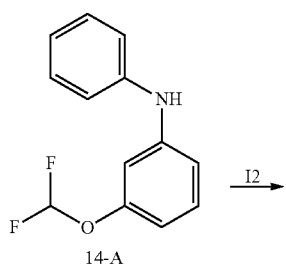

14-A

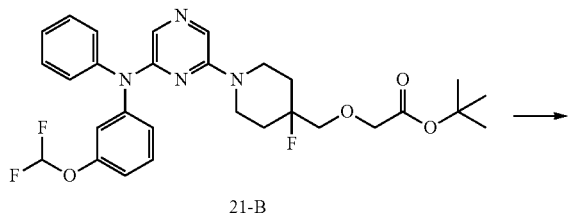

21-B

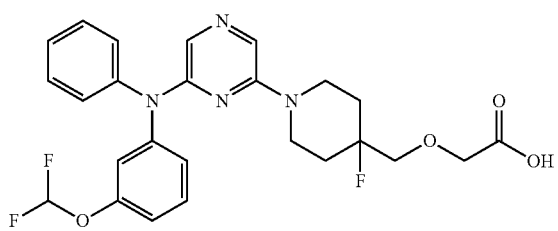 [SMILES: O=C(O)COCC1(F)CCN(c2cncc(N(c3ccccc3)c3cccc(OC(F)F)c3)n2)CC1]

21

Step 1: Synthesis of Compound 21-B

Except for using the corresponding raw materials, compound 21-B was prepared according to the same method as that of compound 3-B in the process of embodiment 3.

MS m/z: 559.1 [M+H]+.

Step 2: Synthesis of Compound 21

Except for using the corresponding raw materials, compound 21 was prepared according to the same method as that of compound 3 in the process of embodiment 3.

MS m/z: 503.0 [M+H]+.

$^1$H NMR (400 MHz, METHANOL-$d_4$) δ ppm 7.47-7.35 (m, 2H), 7.31-7.19 (m, 6H), 7.18-7.10 (m, 2H), 7.05-6.62 (m, 1H), 4.09 (brs, 2H), 3.97 (brd, J=13.2 Hz, 2H), 3.60 (brd, J=18.8 Hz, 2H), 3.18 (brt, J=12.0 Hz, 2H), 1.90-1.68 (m, 4H).

Embodiment 22: Compound 22

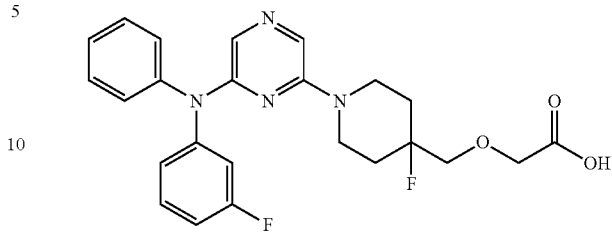

Synthetic Route:

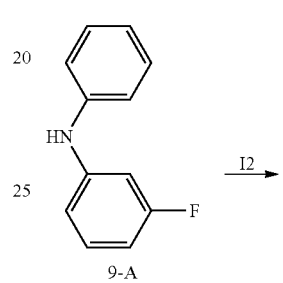

9-A

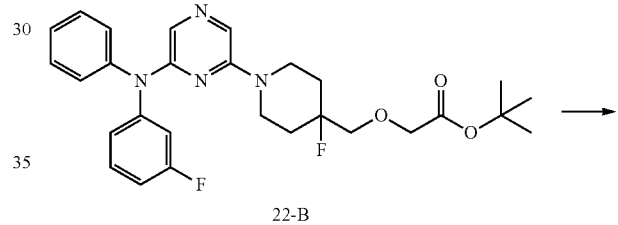

22-B

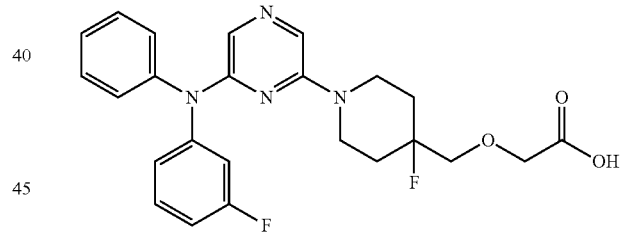

22

Step 1: Synthesis of Compound 22-B

Except for using the corresponding raw materials, compound 22-B was prepared according to the same method as that of compound 3-B in the process of embodiment 3.

MS m/z: 511.2 [M+H]+.

Step 2: Synthesis of Compound 22

Except for using the corresponding raw materials, compound 22 was prepared according to the same method as that of compound 3 in the process of embodiment 3.

MS m/z: 454.9 [M+H]+.

$^1$H NMR (400 MHz, CHLOROFORM-d) δ ppm 7.65 (s, 1H), 7.40-7.29 (m, 3H), 7.28-7.18 (m, 4H), 6.95 (brd, J=8.0 Hz, 2H), 6.86-6.78 (m, 1H), 4.09 (s, 2H), 3.93 (brd, J=13.2 Hz, 2H), 3.63-3.51 (m, 2H), 3.18 (brt, J=12.0 Hz, 2H), 1.94-1.89 (m, 2H), 1.77-1.54 (m, 2H).

Embodiment 23: Compound 23

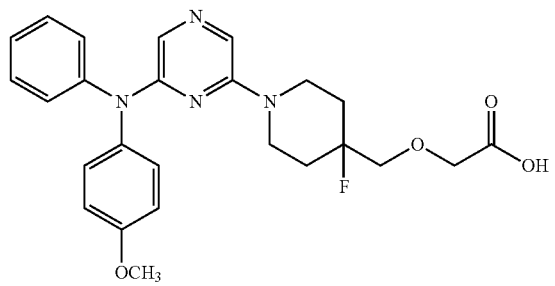 [SMILES: COc1ccc(N(c2ccccc2)c2cncc(N3CCC(F)(COCC(=O)O)CC3)n2)cc1]

Synthetic Route:

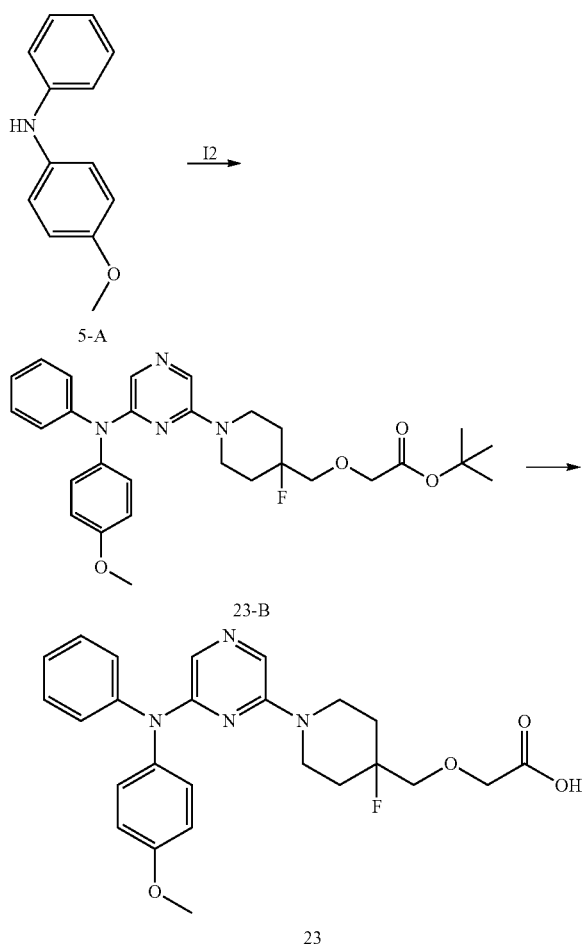

Step 1: Synthesis of Compound 23-B

Except for using the corresponding raw materials, compound 23-B was prepared according to the same method as that of compound 3-B in the process of embodiment 3.

MS m/z: 523.1 [M+H]$^+$.

Step 2: Synthesis of Compound 23

Except for using the corresponding raw materials, compound 23 was prepared according to the same method as that of compound 3 in the process of embodiment 3.

MS m/z: 467.0 [M+H]$^+$.

$^1$H NMR (400 MHz, METHANOL-d$_4$) δ ppm 7.40-7.32 (m, 2H), 7.26-7.12 (m, 5H), 6.98 (d, J=9.0 Hz, 2H), 4.12 (s, 2H), 3.97 (brd, J=12.8 Hz, 2H), 3.83 (s, 3H), 3.60 (d, J=19.2 Hz, 2H), 3.23-3.11 (m, 2H), 1.94-1.61 (m, 4H).

Embodiment 24: Compound 24

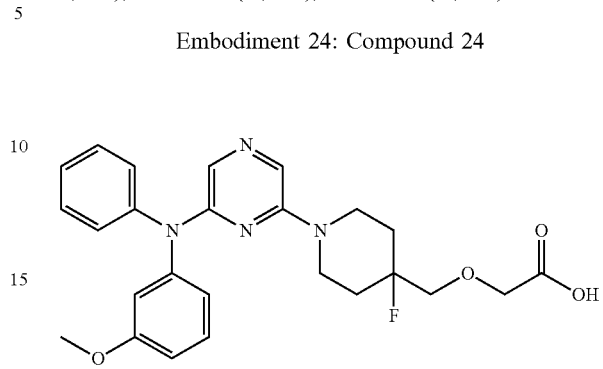

Synthetic Route:

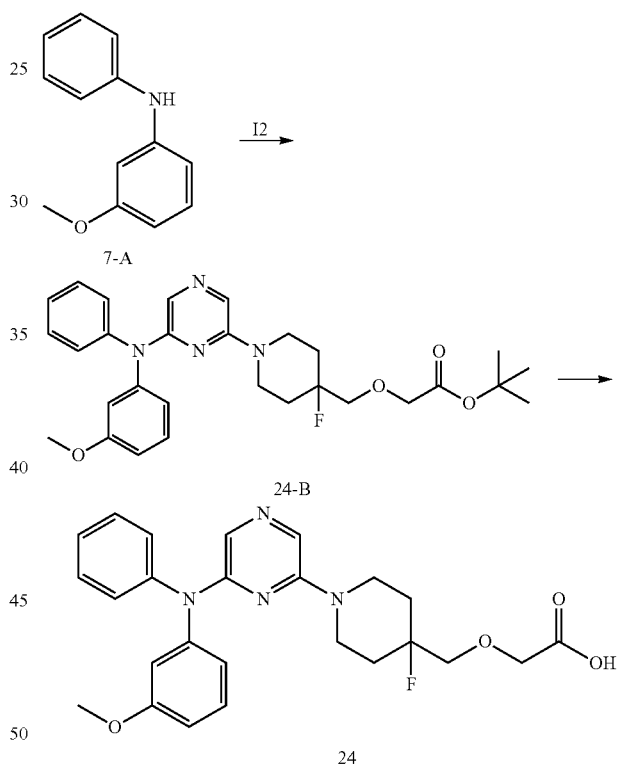

Step 1: Synthesis of Compound 24-B

Except for using the corresponding raw materials, compound 24-B was prepared according to the same method as that of compound 3-B in the process of embodiment 3.

MS m/z: 523.1 [M+H]$^+$.

Step 2: Synthesis of Compound 24

Except for using the corresponding raw materials, compound 24 was prepared according to the same method as that of compound 3 in the process of embodiment 3.

MS m/z: 467.0 [M+H]$^+$.

$^1$H NMR (400 MHz, METHANOL-d$_4$) δ ppm 7.42-7.35 (m, 2H), 7.32-7.19 (m, 4H), 6.86-6.74 (m, 3H), 4.11 (s, 2H), 4.03-3.93 (m, 2H), 3.76 (s, 3H), 3.65-3.55 (m, 2H), 3.24-3.12 (m, 2H), 1.91-1.63 (m, 4H).

Embodiment 25: Compound 25

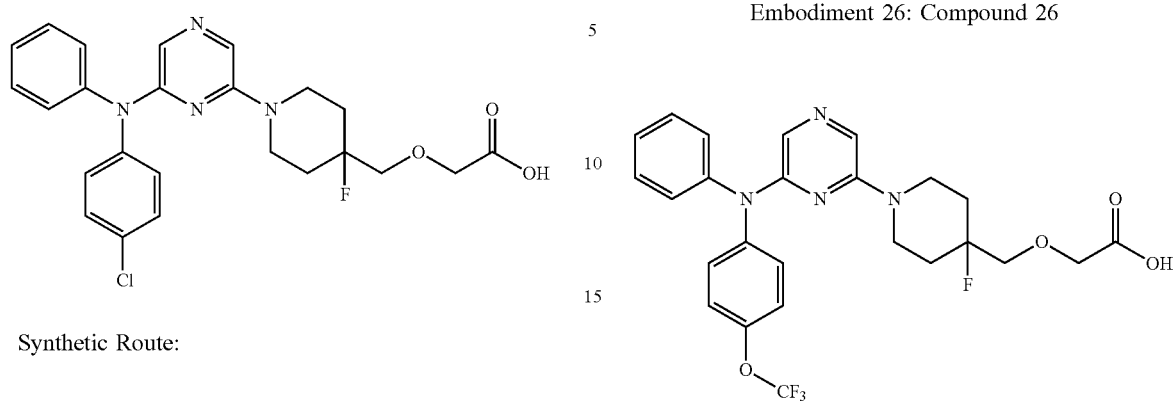

Synthetic Route:

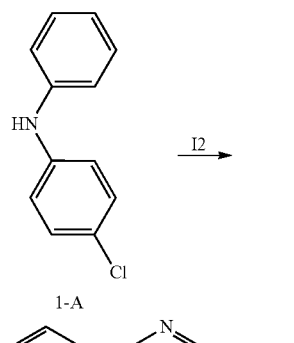

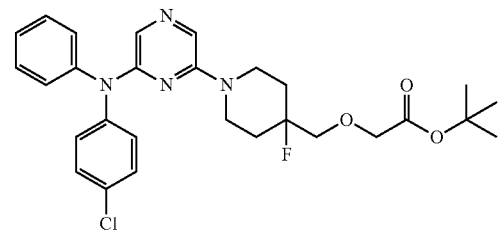

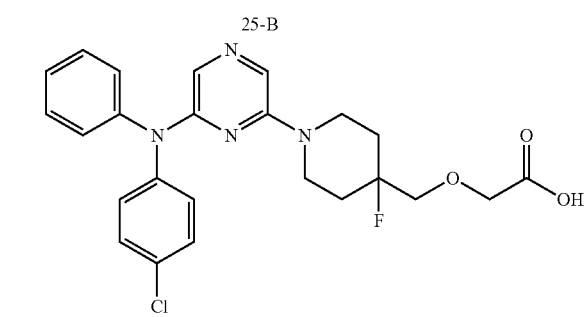

Step 1: Synthesis of Compound 25-B

Except for using the corresponding raw materials, compound 25-B was prepared according to the same method as that of compound 3-B in the process of embodiment 3.

MS m/z: 527.1 [M+H]+.

Step 2: Synthesis of Compound 25

Except for using the corresponding raw materials, compound 25 was prepared according to the same method as that of compound 3 in the process of embodiment 3.

MS m/z: 470.9 [M+H]+.

$^1$H NMR (400 MHz, CHLOROFORM-d) δ ppm 7.54 (brs, 1H), 7.31-7.22 (m, 3H), 7.18-7.08 (m, 5H), 7.04 (d, J=8.8 Hz, 2H), 4.06-3.95 (m, 2H), 3.82 (brd, J=12.8 Hz, 2H), 3.54-3.42 (m, 2H), 3.08 (brt, J=11.6 Hz, 2H), 1.82 (brt, J=11.6 Hz, 2H), 1.71-1.43 (m, 2H).

Embodiment 26: Compound 26

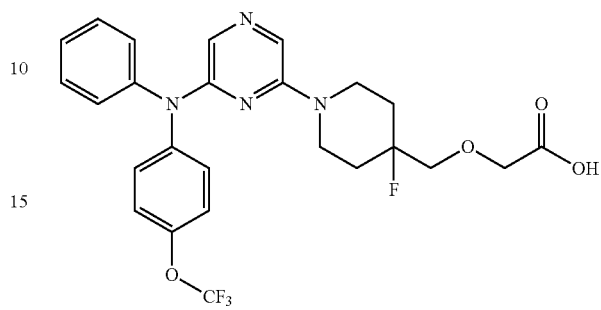

Synthetic Route:

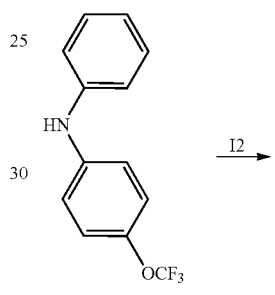

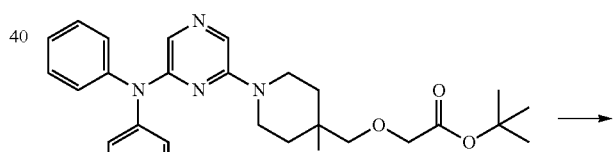

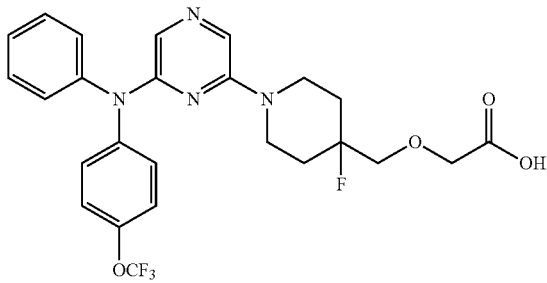

Step 1: Synthesis of Compound 26-B

Except for using the corresponding raw materials, compound 26-B was prepared according to the same method as that of compound 3-B in the process of embodiment 3.

MS m/z: 577.1 [M+H]⁺.

Step 2: Synthesis of Compound 26

Except for using the corresponding raw materials, compound 26 was prepared according to the same method as that of compound 3 in the process of embodiment 3.

MS m/z: 521.0 [M+H]⁺.

$^1$H NMR (400 MHz, METHANOL-$d_4$) δ ppm 7.47-7.39 (m, 2H), 7.33-7.23 (m, 7H), 4.12 (s, 2H), 3.97 (brd, J=13.1 Hz, 2H), 3.61 (brd, J=19.2 Hz, 2H), 3.19 (brt, J=11.2 Hz, 2H), 1.93-1.63 (m, 4H).

Embodiment 27: Compound 27

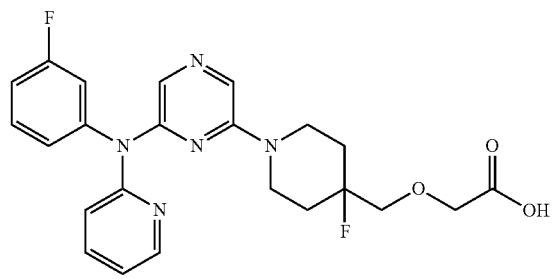 [SMILES: O=C(O)COCC1(F)CCN(c2cncc(N(c3cccc(F)c3)c3ccccn3)n2)CC1]

Synthetic Route:

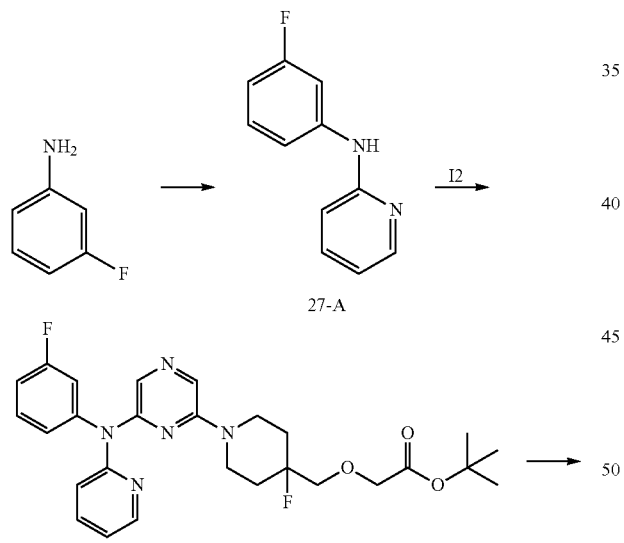

Step 1: Synthesis of Compound 27-A

3-Fluoroaniline (210.99 mg, 1.90 mmol), 6-bromopyridine (0.3 g, 1.90 mmol) and cesium carbonate (1.86 g, 5.70 mmol) were mixed uniformly with dioxane (20 mL), and the system was replaced with nitrogen for three times, and Xphos (181.04 mg, 379.76 μmol) and Pd$_2$(dba)$_3$ (173.88 mg, 189.88 μmol) were added, and the system was replaced with nitrogen for three times once again. The reaction solution was stirred at 100° C. for 12 hours under nitrogen protection. The solvent was removed under reduced pressure, and the residue was separated by chromatography column (petroleum ether/tetrahydrofuran=10/1) to obtain 27-A.

MS m/z: 188.9 [M+H]⁺.

Step 2: Synthesis of Compound 27-B

Except for using the corresponding raw materials, compound 27-B was prepared according to the same method as that of compound 3-B in the process of embodiment 3.

MS m/z: 512.1 [M+H]⁺.

Step 3: Synthesis of Compound 27

Except for using the corresponding raw materials, compound 27 was prepared according to the same method as that of compound 3 in the process of embodiment 3.

MS m/z: 456.0 [M+H]⁺.

$^1$H NMR (400 MHz, CHLOROFORM-d) δ ppm 8.27 (brd, J=3.6 Hz, 1H), 7.67 (brs, 1H), 7.55-7.48 (m, 2H), 7.25-7.22 (m, 1H), 7.02-6.78 (m, 5H), 3.97 (brs, 2H), 3.88-3.76 (m, 2H), 3.51-3.41 (m, 2H), 3.10-3.04 (m, 2H), 1.78-1.51 (m, 4H).

Embodiment 28: Compound 28

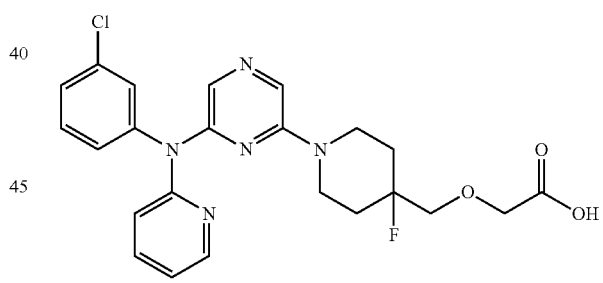

Synthetic Route:

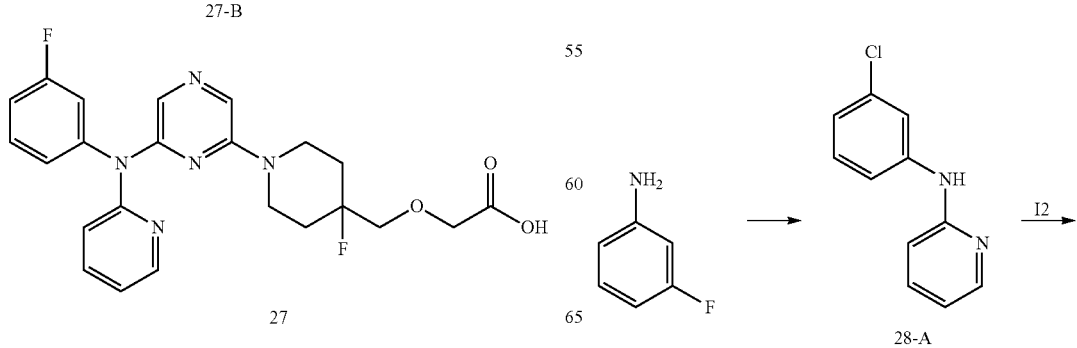

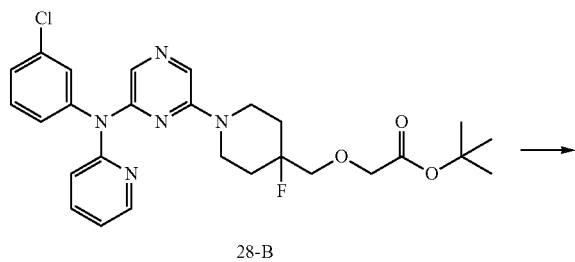

28-B

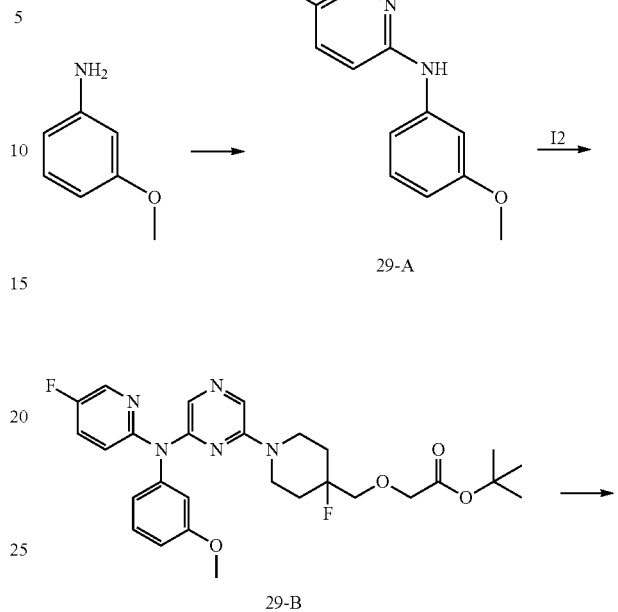

29-A

29-B

29

Step 1: Synthesis of Compound 28-A

Except for using the corresponding raw materials, compound 28-A was prepared according to the same method as that of compound 27-A in the process of embodiment 27.

MS m/z: 204.9 [M+H]$^+$.

Step 2: Synthesis of Compound 28-B

Except for using the corresponding raw materials, compound 28-B was prepared according to the same method as that of compound 3-B in the process of embodiment 3.

MS m/z: 528.1 [M+H]$^+$.

Step 3: Synthesis of Compound 28

Except for using the corresponding raw materials, compound 28 was prepared according to the same method as that of compound 3 in the process of embodiment 3.

MS m/z: 471.9 [M+H]$^+$.

$^1$H NMR (400 MHz, CHLOROFORM-d) δ=8.27 (brd, J=4.0 Hz, 1H), 7.67 (brs, 1H), 7.59-7.42 (m, 2H), 7.19 (s, 2H), 7.10-6.90 (m, 4H), 3.94 (brs, 2H), 3.87-3.72 (m, 2H), 3.52-3.36 (m, 2H), 3.07 (brt, J=12.8 Hz, 2H), 1.87-1.41 (m, 4H).

Embodiment 29: Compound 29

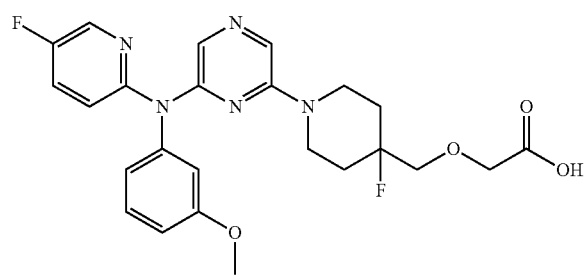 [SMILES: COc1cccc(N(c2ccc(F)cn2)c2cncc(N3CCC(F)(COCC(=O)O)CC3)n2)c1]

Synthetic Route:

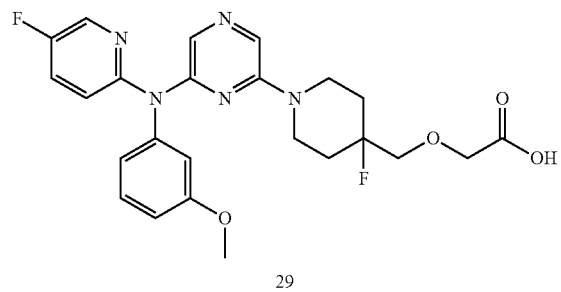

Step 1: Synthesis of Compound 29-A

Except for using the corresponding raw materials, compound 29-A was prepared according to the same method as that of compound 27-A in the process of embodiment 27.

MS m/z: 218.9 [M+H]$^+$.

Step 2: Synthesis of Compound 29-B

Except for using the corresponding raw materials, compound 29-B was prepared according to the same method as that of compound 3-B in the process of embodiment 3.

MS m/z: 542.2 [M+H]$^+$.

Step 3: Synthesis of Compound 29

Except for using the corresponding raw materials, compound 29 was prepared according to the same method as that of compound 3 in the process of embodiment 3.

MS m/z: 486.0 [M+H]$^+$.

$^1$H NMR (400 MHz, CHLOROFORM-d) δ ppm 8.12 (d, J=3.2 Hz, 1H), 7.63 (s, 1H), 7.38 (s, 1H), 7.31-7.20 (m, 2H), 7.07-7.01 (m, 1H), 6.76-6.62 (m, 3H), 3.98 (s, 2H), 3.82 (brd, J=12.4 Hz, 2H), 3.68 (s, 3H), 3.51-3.42 (m, 2H), 3.08 (brt, J=12.2 Hz, 2H), 1.88-1.45 (m, 4H).

Embodiment 30: Compound 30

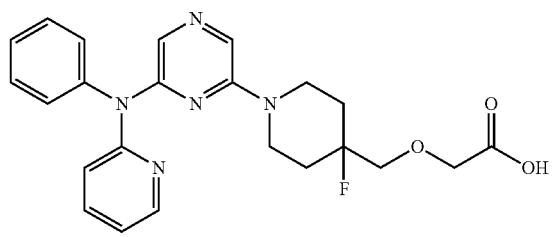 [SMILES: O=C(O)COCC1(F)CCN(c2cncc(N(c3ccccc3)c3ccccn3)n2)CC1]

Synthetic Route:

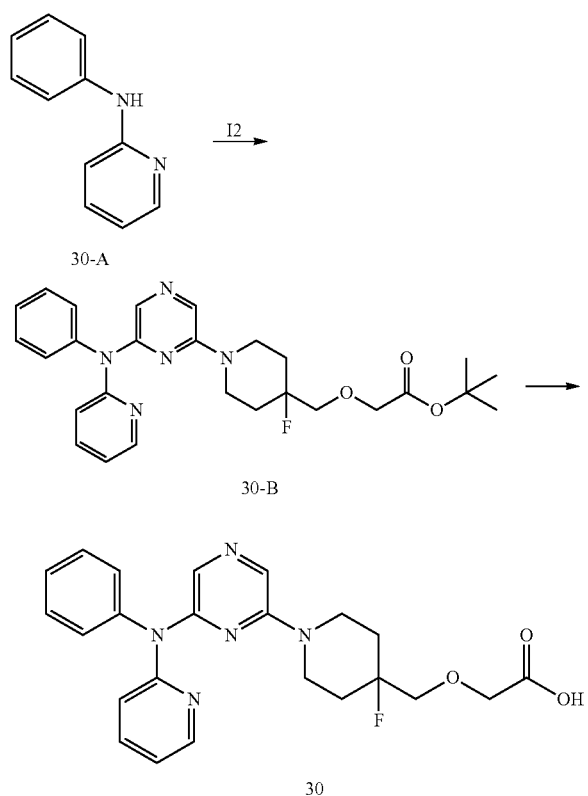

Step 1: Synthesis of Compound 30-B

Except for using the corresponding raw materials, compound 30-B was prepared according to the same method as that of compound 3-B in the process of embodiment 3.

MS m/z: 494.2 [M+H]$^+$.

Step 2: Synthesis of Compound 30

Except for using the corresponding raw materials, compound 30 was prepared according to the same method as that of compound 3 in the process of embodiment 3.

MS m/z: 438.0 [M+H]$^+$.

$^1$H NMR (400 MHz, CHLOROFORM-d) δ ppm 8.25 (brd, J=3.3 Hz, 1H), 7.49 (brt, J=6.8 Hz, 2H), 7.35-7.23 (m, 2H), 7.18-7.06 (m, 3H), 6.99-6.83 (m, 2H), 4.05-3.70 (m, 4H), 3.56-3.32 (m, 2H), 3.05 (brt, J=12.0 Hz, 2H), 1.85-1.41 (m, 4H).

Embodiment 31: Compound 31

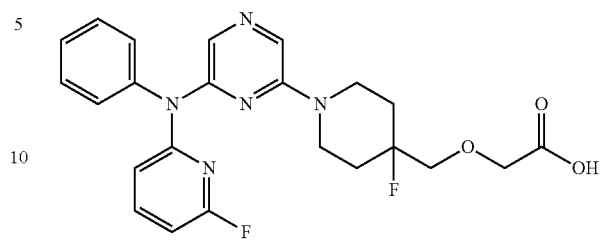

Synthetic Route:

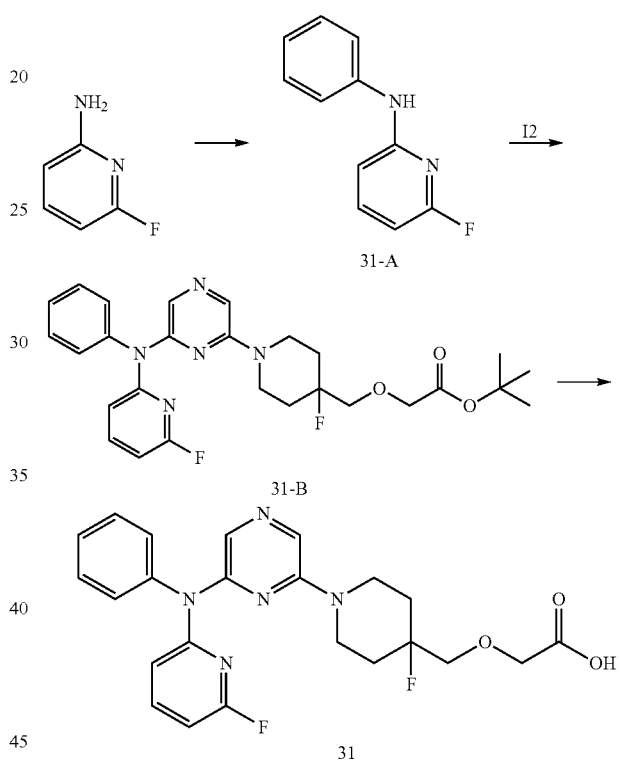

Step 1: Synthesis of Compound 31-A

Except for using the corresponding raw materials, compound 31-A was prepared according to the same method as that of compound 27-A in the process of embodiment 27.

MS m/z: 189.0 [M+H]$^+$.

Step 2: Synthesis of Compound 31-B

Except for using the corresponding raw materials, compound 31-B was prepared according to the same method as that of compound 3-B in the process of embodiment 3.

MS m/z: 512.2 [M+H]$^+$.

Step 3: Synthesis of Compound 31

Except for using the corresponding raw materials, compound 31 was prepared according to the same method as that of compound 3 in the process of embodiment 3.

MS m/z: 456.0 [M+H]$^+$.

$^1$H NMR (400 MHz, CHLOROFORM-d) δ ppm 7.74-7.31 (m, 4H), 7.29-7.07 (m, 5H), 6.65 (brd, J=7.6 Hz, 1H), 6.42 (brd, J=5.6 Hz, 1H), 4.08-3.68 (m, 4H), 3.43 (brd, J=17.6 Hz, 2H), 3.05 (brs, 2H), 1.78 (brs, 2H), 1.67-1.34 (m, 2H).

Embodiment 32: Compound 32

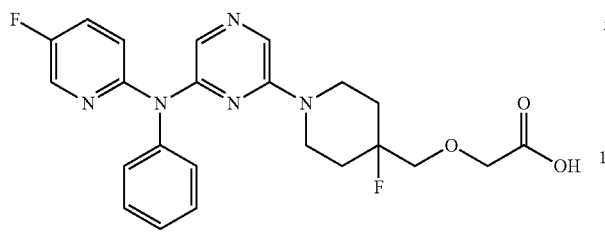

Synthetic Route:

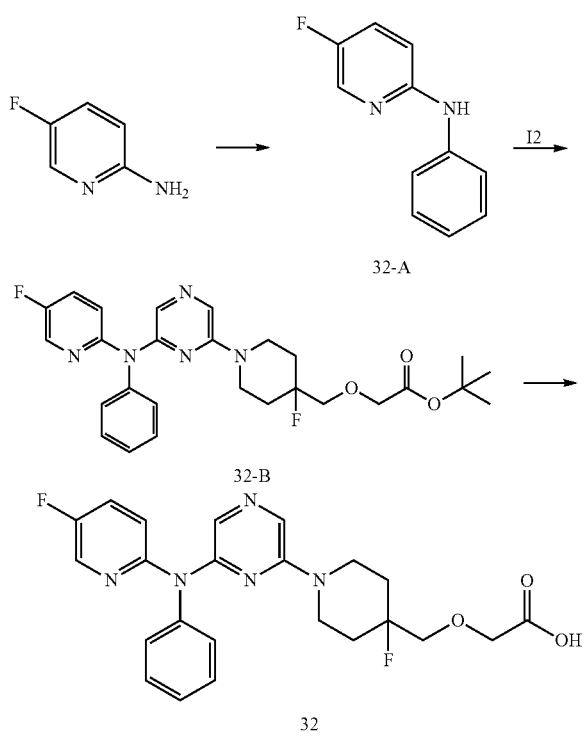

Step 1: Synthesis of Compound 32-A

To dichloromethane (20 mL) were added 2-amino-5-fluoropyridine (2 g, 17.84 mmol), phenylboronic acid (4.35 g, 35.68 mmol), copper acetate (3.24 g, 17.84 mmol) and pyridine (2.82 g, 35.68 mmol), and after the reaction solution was stirred at 25° C. for 14 hours under an atmosphere of oxygen (15 psi), the reaction solution was concentrated to obtain a crude product. The crude product was separated by column chromatography (eluent: petroleum ether/ethyl acetate=25/1) to obtain 32-A.

MS m/z: 189.0 [M+H]$^+$.

Step 2: Synthesis of Compound 32-B

Except for using the corresponding raw materials, compound 32-B was prepared according to the same method as that of compound 3-B in the process of embodiment 3.

To a solution of dioxane (15 mL) were added compound 12 (0.5 g, 1.39 mmol), 32-A (392.28 mg, 2.08 mmol), bis(dibenzylideneacetone)palladium (39.95 mg, 69.48), 4,5-bisdiphenylphosphino-9,9-dimethyloxanthene (80.40 mg, 138.96 umol) and cesium carbonate (1.36 g, 4.17 mmol), and then the mixture was degassed and purified with nitrogen for three times. And after the mixed system was stirred at 100° C. for 14 hours under an atmosphere of nitrogen, the mixed system was concentrated to obtain a crude product. The crude product was separated by column chromatography (eluent: petroleum ether/ethyl acetate=2:1) to obtain compound 32-B.

MS m/z: 512.2 [M+H]$^+$.

Step 3: Synthesis of Compound 32

Except for using the corresponding raw materials, compound 32 was prepared according to the same method as that of compound 3 in the process of embodiment 3.

To a solution of compound 32-B (0.32 g, 625.53 umol) in methanol (5 mL) was added sodium hydroxide (5.00 g, 12.51 mmol, 10%), and the reaction system was stirred at 40° C. for 0.5 hour. The reaction system was concentrated to obtain a crude product, and the crude product was diluted with water (20 mL), adjusted the pH to 6 with hydrochloric acid (2N), extracted with ethyl acetate (50 mL×2). The organic phase was combined, washed with saturated brine (20 mL) and dried over anhydrous sodium sulfate. After the anhydrous sodium sulfate was filtered off, the solvent was removed under reduced pressure to obtain a crude product. The crude product didn't need purification to give compound 32.

MS m/z: 456.0 [M+H]$^+$.

$^1$H NMR (CHLOROFORM-d, 400 MHz) δ ppm 8.21 (d, J=2.4 Hz, 1H), 7.70 (s, 1H), 7.43-7.35 (m, 4H), 7.28-7.24 (m, 1H), 7.19 (d, J=7.2 Hz, 2H), 7.10 (dd, J=3.6, 8.8 Hz, 1H), 4.14 (s, 2H), 3.90 (d, J=13.6 Hz, 2H), 3.58 (brd, J=19.2 Hz, 2H), 3.19 (t, J=12.0 Hz, 2H), 1.92-1.86 (m, 2H), 1.76-1.59 (m, 2H).

Embodiment 33: Compound 33

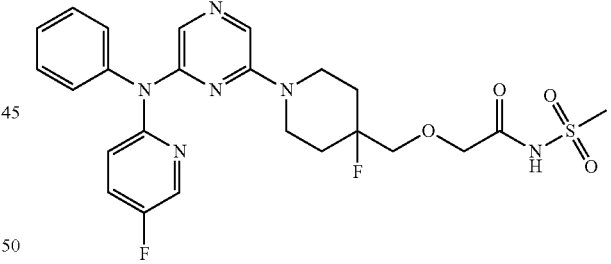

Synthetic Route:

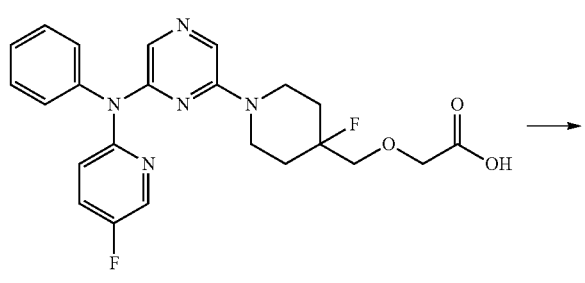

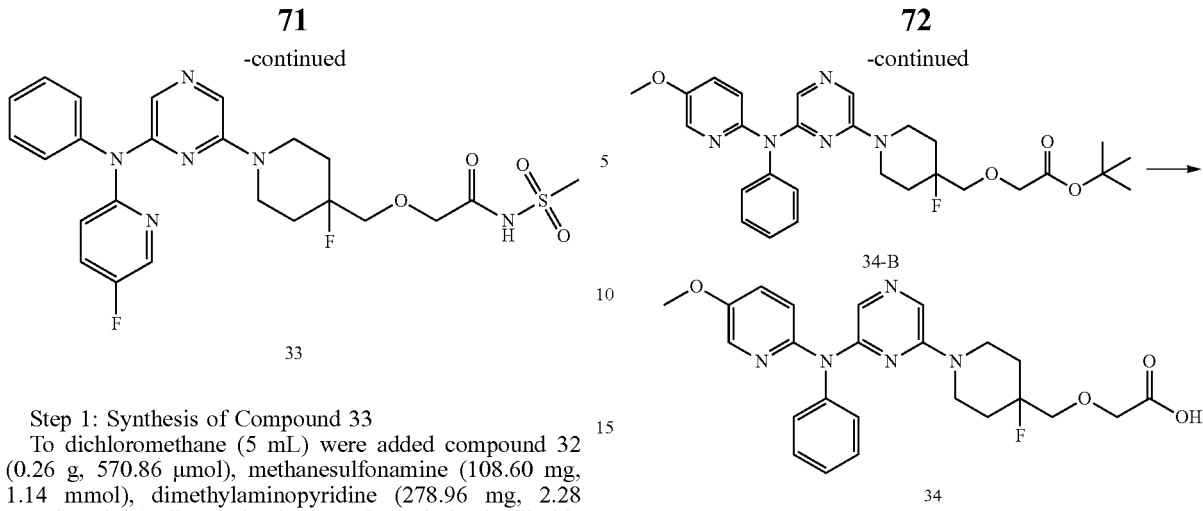

Step 1: Synthesis of Compound 33

To dichloromethane (5 mL) were added compound 32 (0.26 g, 570.86 μmol), methanesulfonamine (108.60 mg, 1.14 mmol), dimethylaminopyridine (278.96 mg, 2.28 mmol) and 1-(3-dimethylaminopropyl)-3-ethylcarbodiimide hydrochloride (218.87 mg, 1.14 mmol, and the mixture was replaced with nitrogen for three times, and the mixed system was stirred at 20° C. for 14 hours under an atmosphere of nitrogen. The reaction system was concentrated and added with hydrochloric acid (2N, 30 mL), extracted with dichloromethane (50 mL). And the extract was washed with hydrochloric acid (2N, 50 mL*2) and saturated brine (50 mL), and dried over anhydrous sodium sulfate. The anhydrous sodium sulfate was filtered off, and the solvent was removed under reduced pressure to obtain compound 33.

MS m/z: 532.9 [M+H]$^+$.

$^1$H NMR (400 MHz, CHLOROFORM-d) δ ppm 8.21-8.20 (m, 1H), 7.71 (s, 1H), 7.54 (s, 1H), 7.41-7.32 (m, 3H), 7.27-7.26 (m, 1H), 7.21-7.19 (m, 2H), 7.12-7.08 (m, 1H), 4.15 (s, 2H), 4.03-3.91 (m, 2H), 3.63-3.55 (m, 2H), 3.32 (s, 3H), 3.19-3.07 (m, 2H), 1.92-1.86 (m, 2H), 1.67-1.47 (m, 2H).

Embodiment 34: Compound 34

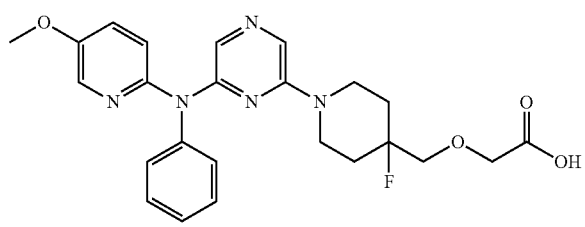 [SMILES: COc1ccc(N(c2ccccc2)c2cncc(N3CCC(F)(COCC(=O)O)CC3)n2)nc1]

Synthetic Route:

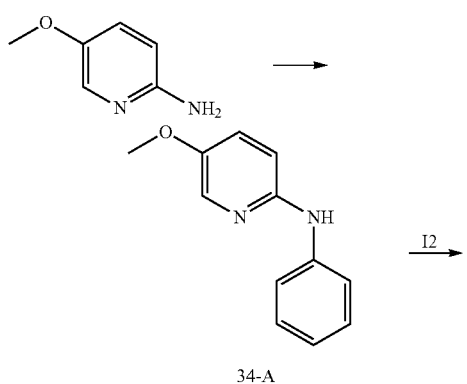

Step 1: Synthesis of Compound 34-A

Except for using the corresponding raw materials, compound 34-A was prepared according to the same method as that of compound 32-A in the process of embodiment 32.

MS m/z: 200.9 [M+H]$^+$.

Step 2: Synthesis of Compound 34-B

Except for using the corresponding raw materials, compound 34-B was prepared according to the same method as that of compound 3-B in the process of embodiment 3.

MS m/z: 524.3 [M+H]$^+$.

Step 3: Synthesis of Compound 34

Except for using the corresponding raw materials, compound 34 was prepared according to the same method as that of compound 3 in the process of embodiment 3.

MS m/z: 411.0 [M+H]$^+$.

$^1$H NMR (CHLOROFORM-d, 400 MHz) δ ppm 8.11 (d, J=3.2 Hz, 1H), 7.64 (s, 1H), 7.38-7.32 (m, 3H), 7.24-7.19 (m, 4H), 7.07 (d, J=8.8 Hz, 1H), 4.27 (s, 3H), 3.91-3.87 (m, 5H), 3.57 (d, J=19.6 Hz, 2H), 3.18 (t, J=12.0 Hz, 2H), 1.89-1.83 (m, 2H), 1.72-1.60 (m, 2H).

Embodiment 35: Compound 35

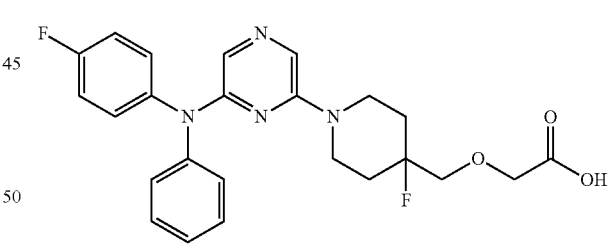

Synthetic Route:

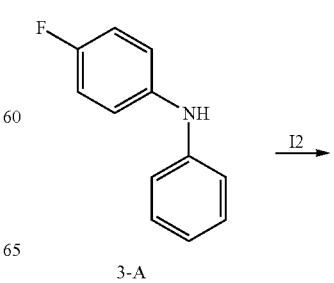

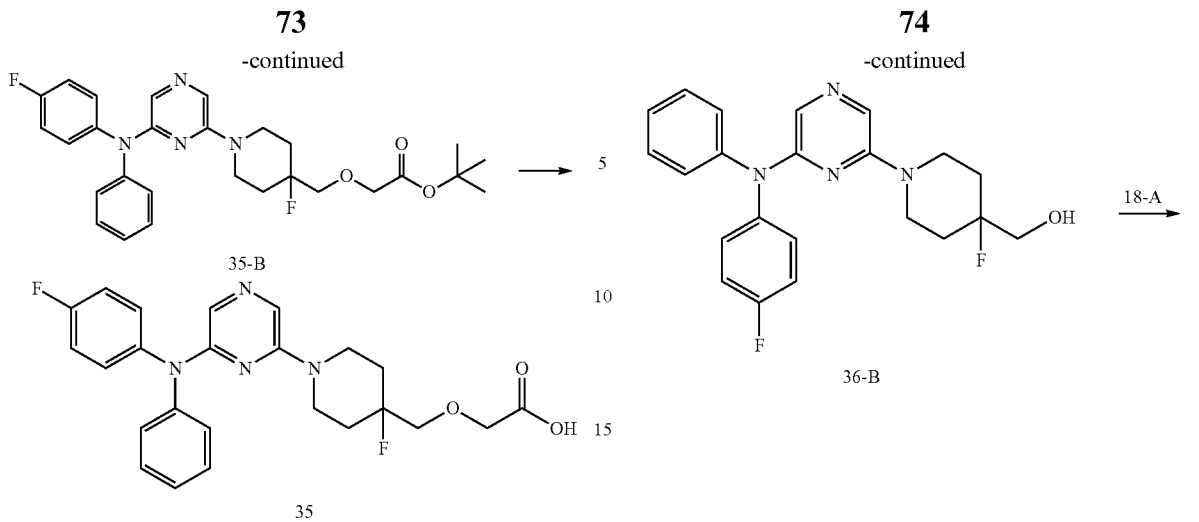

Step 1: Synthesis of Compound 35-B

Except for using the corresponding raw materials, compound 35-B was prepared according to the same method as that of compound 3-B in the process of embodiment 3.

MS m/z: 511.2 [M+H]$^+$.

Step 2: Synthesis of Compound 35

Except for using the corresponding raw materials, compound 35 was prepared according to the same method as that of compound 3 in the process of embodiment 3.

MS m/z: 455.0 [M+H]$^+$.

$^1$H NMR (CHLOROFORM-d, 400 MHz) δ ppm 8.91 (brs, 1H), 7.59 (s, 1H), 7.35-7.31 (m, 2H), 7.20-7.16 (m, 6H), 7.02 (t, J=8.8 Hz, 2H), 4.14 (s, 2H), 3.90 (brd, J=13.2 Hz, 2H), 3.58 (brd, J=19.6 Hz, 2H), 3.17 (brt, J=12.0 Hz, 2H), 1.92-1.83 (m, 2H), 1.75-1.58 (m, 2H).

Embodiment 36: Compound 36

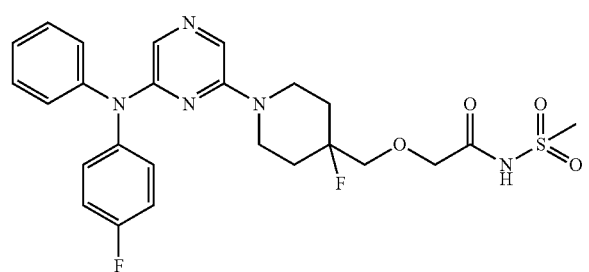 [SMILES: CS(=O)(=O)NC(=O)COCC1(F)CCN(c2cncc(N(c3ccccc3)c3ccc(F)cc3)n2)CC1]

Synthetic Route:

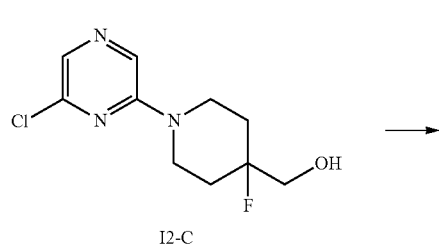

Step 1: Synthesis of Compound 36-B

Except for using the corresponding raw materials, compound 36-B was prepared according to the same method as that of compound 3-B in the process of embodiment 3.

MS m/z: 397.2 [M+H]$^+$.

Step 2: Synthesis of Compound 36

Except for using the corresponding raw materials, compound 36 was prepared according to the same method as that of compound 18 in the process of embodiment 18.

MS m/z: 532.3 [M+H]$^+$.

$^1$H NMR (400 MHz, ACETONITRILE-d$_3$) δ ppm 7.68 (s, 1H), 7.36-7.44 (m, 2H), 7.09-7.30 (m, 8H), 4.14 (s, 2H), 3.91 (brd, J=13.56 Hz, 2H), 3.62 (d, J=21.60 Hz, 2H), 3.26 (s, 3H), 3.11-3.21 (m, 2H), 1.80-1.91 (m, 2H), 1.58-1.78 (m, 2H).

Embodiment 37: Compound 37

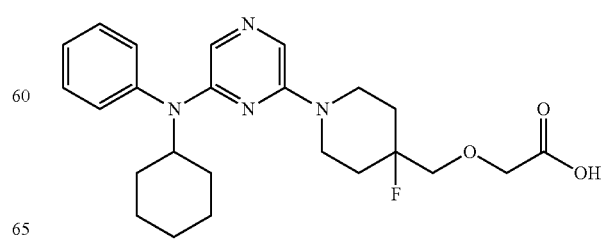

Synthetic Route:

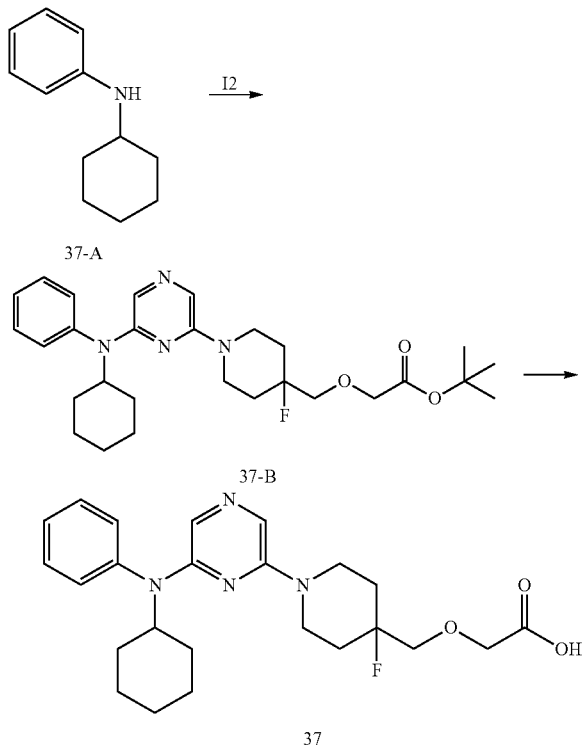

Step 1: Synthesis of Compound 37-B

Except for using the corresponding raw materials, compound 37-B was prepared according to the same method as that of compound 3-B in the process of embodiment 3.

MS m/z: 499.3 [M+H]$^+$.

Step 2: Synthesis of Compound 37

Except for using the corresponding raw materials, compound 37 was prepared according to the same method as that of compound 3 in the process of embodiment 3.

MS m/z: 443.0 [M+H]$^+$.

$^1$H NMR (CHLOROFORM-d, 400 MHz) δ ppm 7.45-7.34 (m, 4H), 7.14-7.12 (m, 2H), 6.60 (s, 1H), 4.55 (t, J=11.6 Hz, 2H), 4.09 (brs, 4H), 4.11-4.09 (m, 2H), 3.65-3.62 (m, 2H), 3.37-3.31 (m, 2H), 2.00-1.76 (m, 8H), 1.42-1.30 (m, 2H), 1.15-0.97 (m, 2H).

Embodiment 38: Compound 38

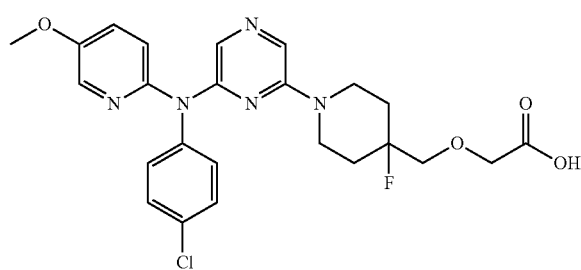 [SMILES: COc1ccc(N(c2ccc(Cl)cc2)c2cncc(N3CCC(F)(COCC(=O)O)CC3)n2)nc1]

Synthetic Route:

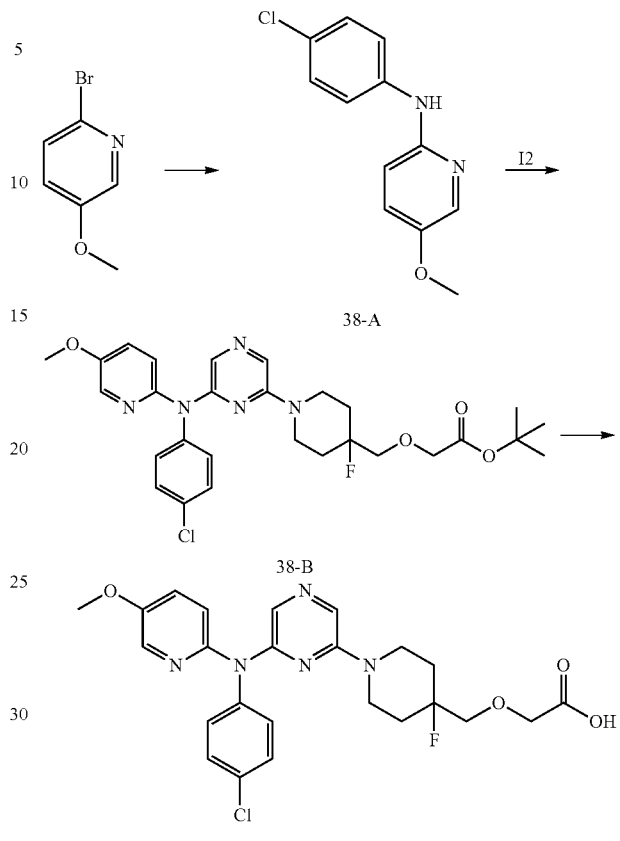

Step 1: Synthesis of Compound 38-A

To dioxane (20 mL) were added 2-bromo-5-methoxypyridine (1.0 g, 5.32 mmol), p-chloroaniline (1.04 g, 8.19 mmol), tris(dibenzylideneacetone) dipalladium (487.03 mg, 531.85 μmol), xantphos (615.48 mg, 1.06 mmol) and cesium carbonate (3.47 g, 10.64 mmol), and the mixture was swept with nitrogen for three times. The mixed system was stirred at 100° C. under an atmosphere of nitrogen for 14 hours and concentrated to obtain a crude product. The crude product was separated by column chromatography (eluent: petroleum ether/ethyl acetate=8/1) to obtain compound 38-A.

MS m/z: 234.9 [M+H]$^+$.

Step 2: Synthesis of Compound 38-B

Except for using the corresponding raw materials, compound 38-B was prepared according to the same method as that of compound 3-B in the process of embodiment 3.

MS m/z: 558.1 [M+H]$^+$.

Step 3: Synthesis of Compound 38

Except for using the corresponding raw materials, compound 38 was prepared according to the same method as that of compound 3 in the process of embodiment 3.

MS m/z: 501.9 [M+H]$^+$.

$^1$H NMR (CHLOROFORM-d, 400 MHz) δ ppm 8.08 (d, J=3.2 Hz, 1H), 7.65 (s, 1H), 7.35 (s, 1H), 7.29-7.27 (m, 2H), 7.21 (dd, J=3.2, 8.8 Hz, 1H), 7.11-7.06 (m, 3H), 4.18 (s, 2H), 3.88-3.81 (m, 5H), 3.53 (d, J=20.0 Hz, 2H), 3.17-3.11 (m, 2H), 1.69-1.87 (m, 2H), 1.69-1.55 (m, 2H).

Embodiment 39: Compound 39

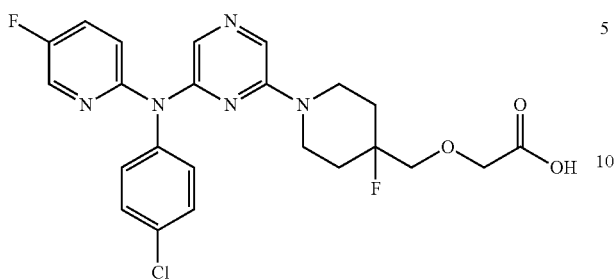

Synthetic Route:

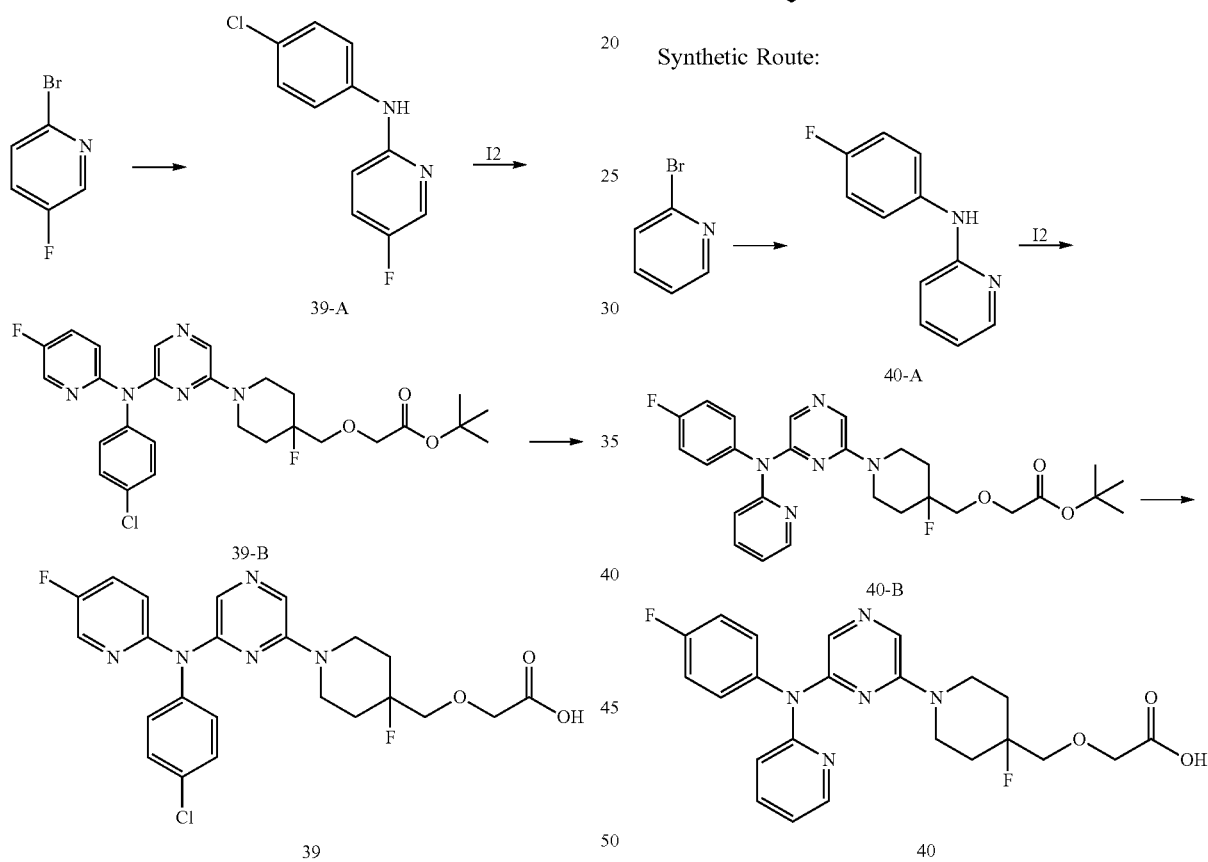

Step 1: Synthesis of Compound 39-A

Except for using the corresponding raw materials, compound 39-A was prepared according to the same method as that of compound 38-A in the process of embodiment 38.
MS m/z: 222.9 [M+H]$^+$.

Step 2: Synthesis of Compound 39-B

Except for using the corresponding raw materials, compound 39-B was prepared according to the same method as that of compound 3-B in the process of embodiment 3.
MS m/z: 546.2 [M+H]$^+$.

Step 3: Synthesis of Compound 39

Except for using the corresponding raw materials, compound 39 was prepared according to the same method as that of compound 3 in the process of embodiment 3.
MS m/z: 489.9 [M+H]$^+$.

$^1$H NMR (CHLOROFORM-d, 400 MHz) δ ppm 8.22 (d, J=3.2 Hz, 1H), 7.73 (s, 1H), 7.43-7.37 (m, 4H), 7.14-7.10 (m, 3H), 4.32-4.14 (m, 1H), 4.17 (s, 3H), 3.92 (brd, J=13.2 Hz, 2H), 3.60 (d, J=19.2 Hz, 2H), 3.20 (brt, J=12.0 Hz, 2H), 1.94-1.88 (m, 2H), 1.77-1.60 (m, 2H).

Embodiment 40: Compound 40

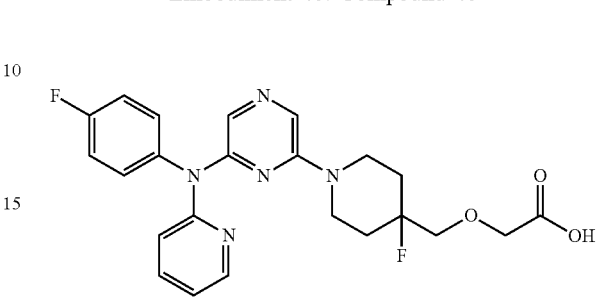

Synthetic Route:

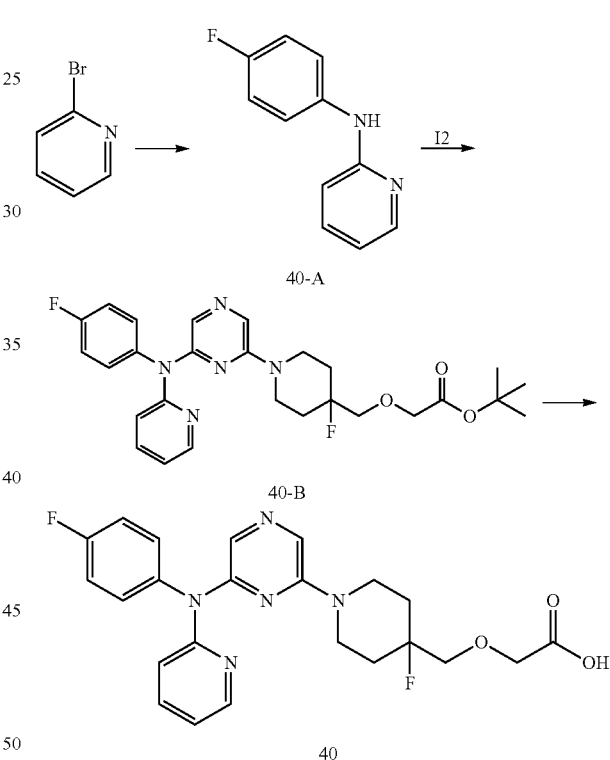

Step 1: Synthesis of Compound 40-A

Except for using the corresponding raw materials, compound 40-A was prepared according to the same method as that of compound 27-A in the process of embodiment 27.
MS m/z: 188.9 [M+H]$^+$.

Step 2: Synthesis of Compound 40-B

Except for using the corresponding raw materials, compound 40-B was prepared according to the same method as that of compound 3-B in the process of embodiment 3.
MS m/z: 512.1 [M+H]$^+$.

Step 3: Synthesis of Compound 40

Except for using the corresponding raw materials, compound 40 was prepared according to the same method as that of compound 3 in the process of embodiment 3.
MS m/z: 456.1 [M+H]$^+$.

¹H NMR (400 MHz, CHLOROFORM-d) δ ppm 8.35 (dd, J=1.3, 5.0 Hz, 1H), 7.72 (s, 1H), 7.65-7.56 (m, 1H), 7.52 (s, 1H), 7.22-7.15 (m, 2H), 7.12-7.05 (m, 2H), 7.05-6.95 (m, 2H), 4.21-4.02 (m, 2H), 3.90 (brd, J=13.6 Hz, 2H), 3.57 (d, J=19.3 Hz, 2H), 3.18 (brt, J=11.5 Hz, 2H), 1.93-1.81 (m, 2H), 1.77-1.58 (m, 2H).

Embodiment 41: Compound 41

Synthetic Route:

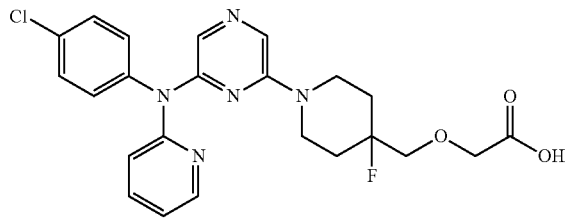 [SMILES: O=C(O)COCC1(F)CCN(c2cncc(N(c3ccc(Cl)cc3)c3ccccn3)n2)CC1]
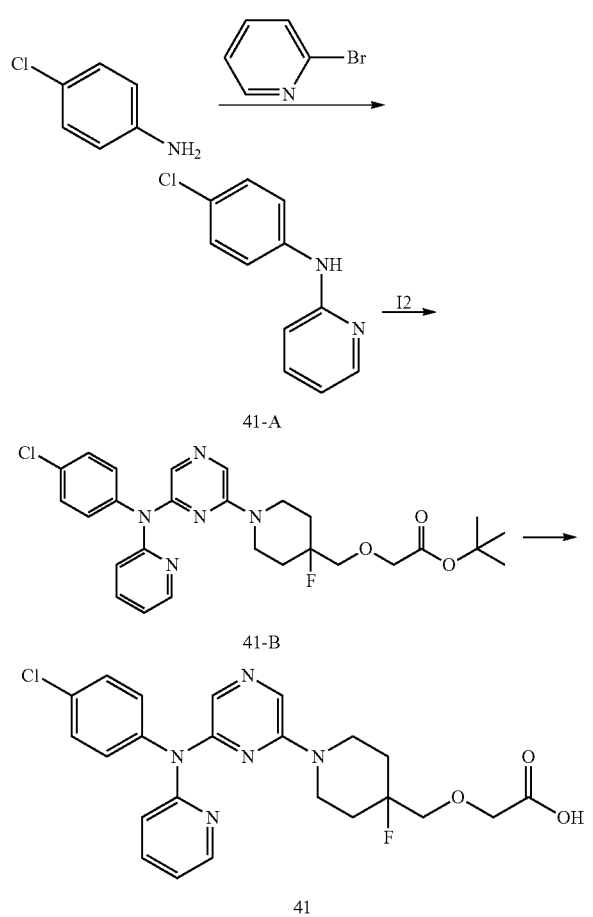

Step 1: Synthesis of Compound 41-A

Except for using the corresponding raw materials, compound 41-A was prepared according to the same method as that of compound 27-A in the process of embodiment 27.

MS m/z: 204.9 [M+H]⁺.

Step 2: Synthesis of Compound 41-B

Except for using the corresponding raw materials, compound 41-B was prepared according to the same method as that of compound 3-B in the process of embodiment 3.

MS m/z: 528.1 [M+H]⁺.

Step 3: Synthesis of Compound 41

Except for using the corresponding raw materials, compound 41 was prepared according to the same method as that of compound 3 in the process of embodiment 3.

MS m/z: 472.0 [M+H]⁺.

¹H NMR (400 MHz, CHLOROFORM-d) δ ppm 8.39-8.31 (m, 1H), 7.73 (s, 1H), 7.65-7.57 (m, 1H), 7.53-7.45 (m, 1H), 7.33 (d, J=8.8 Hz, 2H), 7.26 (s, 1H), 7.13 (d, J=8.8 Hz, 2H), 7.07-6.97 (m, 2H), 4.09 (s, 2H), 3.90 (brd, J=13.3 Hz, 2H), 3.56 (d, J=19.3 Hz, 2H), 3.17 (brt, J=11.7 Hz, 2H), 1.94-1.79 (m, 2H), 1.77-1.54 (m, 2H).

Embodiment 42: Compound 42

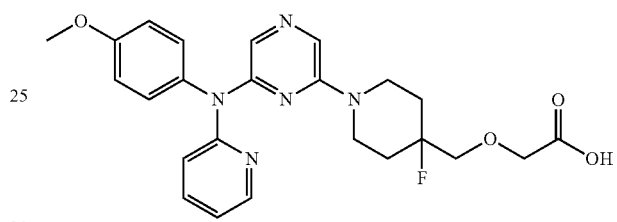

Synthetic Route:

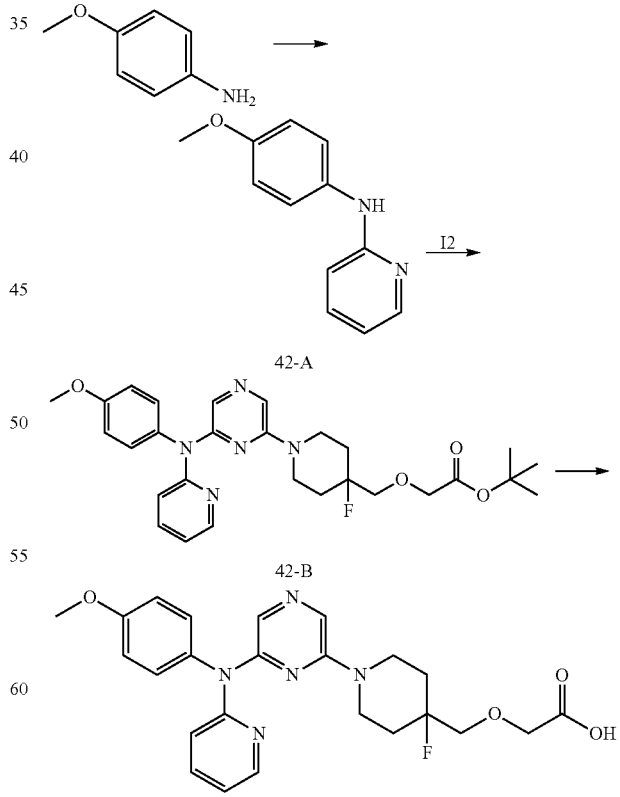

Step 1: Synthesis of Compound 42-A

Except for using the corresponding raw materials, compound 42-A was prepared according to the same method as that of compound 27-A in the process of embodiment 27.

MS m/z: 201.0 [M+H]⁺.

Step 2: Synthesis of Compound 42-B

Except for using the corresponding raw materials, compound 42-B was prepared according to the same method as that of compound 3-B in the process of embodiment 3.

MS m/z: 524.2 [M+H]⁺.

Step 3: Synthesis of Compound 42

Except for using the corresponding raw materials, compound 42 was prepared according to the same method as that of compound 3 in the process of embodiment 3.

MS m/z: 468.2 [M+H]⁺.

¹H NMR (400 MHz, CHLOROFORM-d) δ ppm 8.26 (brs, 1H), 7.65 (brs, 1H), 7.51 (brt, J=7.2 Hz, 2H), 7.10 (brd, J=8.5 Hz, 2H), 6.99 (brd, J=8.3 Hz, 1H), 6.88 (brd, J=8.3 Hz, 3H), 3.85 (brd, J=12.0 Hz, 2H), 3.77 (s, 2H), 3.48 (brd, J=19.8 Hz, 2H), 3.09 (brt, J=11.5 Hz, 2H), 1.85-1.52 (m, 4H).

Embodiment 43: Compound 43

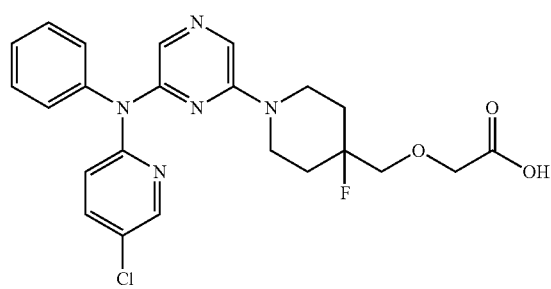 [SMILES: O=C(O)COCC1(F)CCN(c2cncc(N(c3ccccc3)c3ccc(Cl)cn3)n2)CC1]

Synthetic Route:

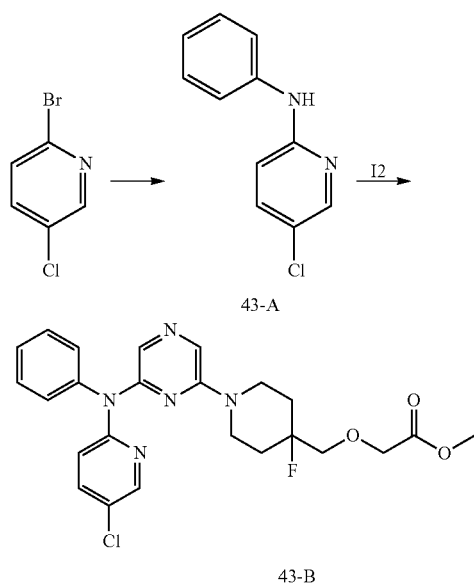

43-A

43-B

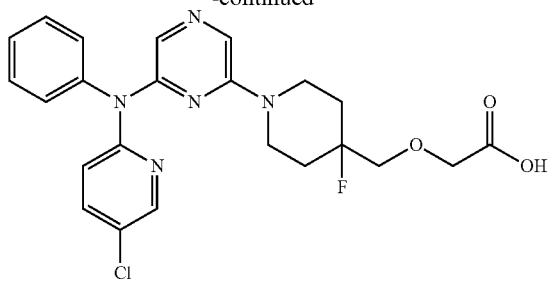

43

Step 1: Synthesis of Compound 43-A

Except for using the corresponding raw materials, compound 43-A was prepared according to the same method as that of compound 27-A in the process of embodiment 27.

MS m/z: 204.9 [M+H]⁺.

Step 2: Synthesis of Compound 43-B

Except for using the corresponding raw materials, compound 43-B was prepared according to the same method as that of compound 3-B in the process of embodiment 3.

MS m/z: 528.1 [M+H]⁺.

Step 3: Synthesis of Compound 43

Except for using the corresponding raw materials, compound 43 was prepared according to the same method as that of compound 3 in the process of embodiment 3.

MS m/z: 472.1 [M+H]⁺.

¹H NMR (400 MHz, CHLOROFORM-d) δ ppm 8.22 (d, J=2.5 Hz, 1H), 7.70 (s, 1H), 7.52-7.44 (m, 2H), 7.39-7.34 (m, 2H), 7.23 (d, J=5.5 Hz, 1H), 7.15 (d, J=7.5 Hz, 2H), 6.99 (d, J=8.8 Hz, 1H), 4.10 (s, 2H), 3.88 (brd, J=13.6 Hz, 2H), 3.54 (brd, J=19.3 Hz, 2H), 3.15 (brt, J=11.7 Hz, 2H), 1.90-1.82 (m, 2H), 1.74-1.54 (m, 2H).

Embodiment 44: Compound 44

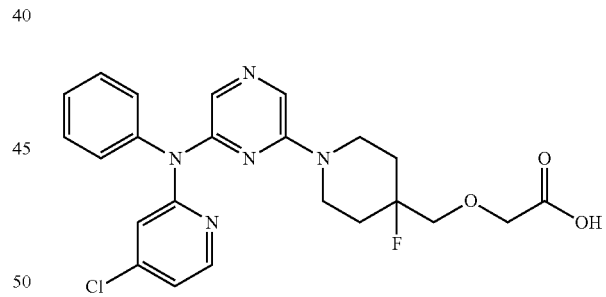

Synthetic Route:

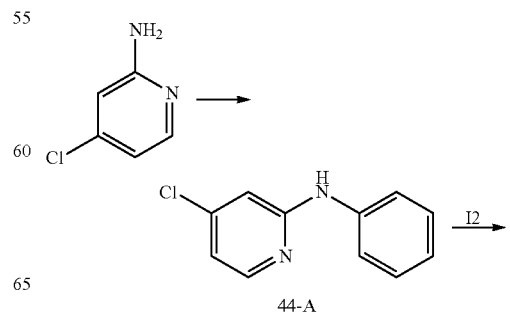

44-A

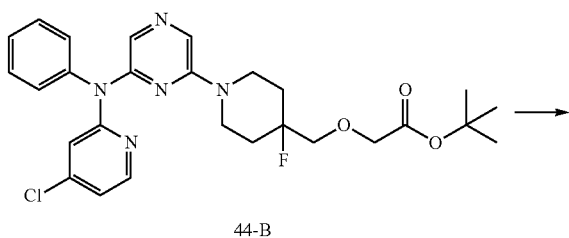

44-B

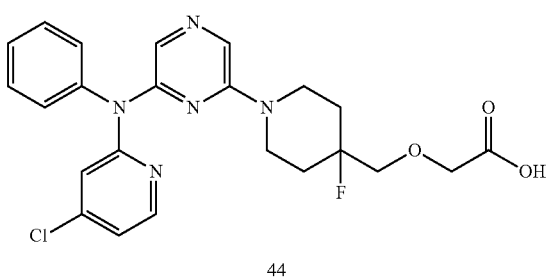

44

Step 1: Synthesis of Compound 44-A

Except for using the corresponding raw materials, compound 44-A was prepared according to the same method as that of compound 32-A in the process of embodiment 32.

MS m/z: 204.9 [M+H]⁺.

Step 2: Synthesis of Compound 44-B

Except for using the corresponding raw materials, compound 44-B was prepared according to the same method as that of compound 3-B in the process of embodiment 3.

MS m/z: 528.1 [M+H]⁺.

Step 3: Synthesis of Compound 44

Except for using the corresponding raw materials, compound 44 was prepared according to the same method as that of compound 3 in the process of embodiment 3.

MS m/z: 472.0 [M+H]⁺.

$^1$H NMR (400 MHz, CHLOROFORM-d) δ ppm 8.20 (d, J=5.5 Hz, 1H), 7.76 (s, 1H), 7.49 (s, 1H), 7.45-7.39 (m, 2H), 7.34-7.28 (m, 1H), 7.26 (s, 1H), 7.20 (d, J=7.3 Hz, 2H), 7.08 (d, J=1.5 Hz, 1H), 6.95 (dd, J=1.6, 5.4 Hz, 1H), 4.12 (s, 2H), 3.94 (brd, J=13.3 Hz, 2H), 3.57 (d, J=19.3 Hz, 2H), 3.21 (brt, J=11.7 Hz, 2H), 1.96-1.83 (m, 2H), 1.78-1.58 (m, 2H).

Embodiment 45: Compound 45

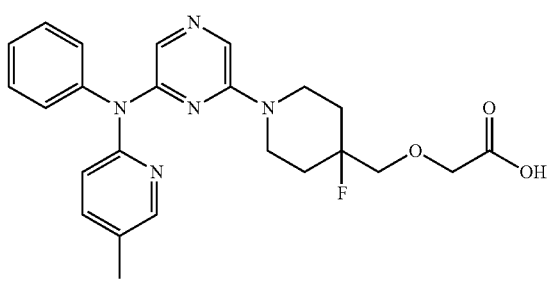

Synthetic Route:

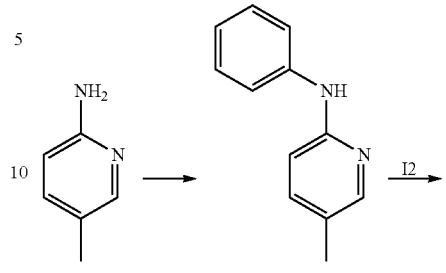

45-A

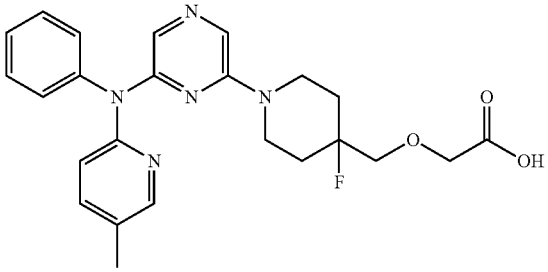 [SMILES: Cc1ccc(N(c2ccccc2)c2cncc(N3CCC(F)(COCC(=O)O)CC3)n2)nc1]

45-B

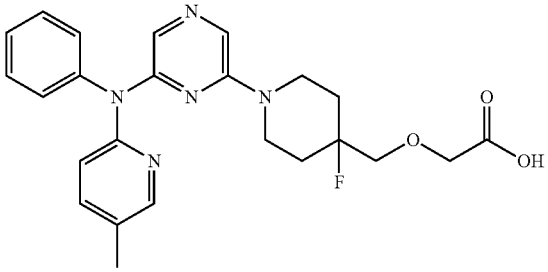 [SMILES: Cc1ccc(N(c2ccccc2)c2cncc(N3CCC(F)(COCC(=O)O)CC3)n2)nc1]

45

Step 1: Synthesis of Compound 45-A

Except for using the corresponding raw materials, compound 45-A was prepared according to the same method as that of compound 32-A in the process of embodiment 32.

MS m/z: 185.0 [M+H]⁺.

Step 2: Synthesis of Compound 45-B

Except for using the corresponding raw materials, compound 45-B was prepared according to the same method as that of compound 3-B in the process of embodiment 3.

MS m/z: 508.2 [M+H]⁺.

Step 3: Synthesis of Compound 45

Except for using the corresponding raw materials, compound 45 was prepared according to the same method as that of compound 3 in the process of embodiment 3.

MS m/z: 452.5 [M+H]⁺.

$^1$H NMR (400 MHz, CHLOROFORM-d) δ ppm 8.20 (s, 1H), 7.67 (brs, 1H), 7.47-7.39 (m, 2H), 7.38-7.31 (m, 2H), 7.26 (s, 1H), 7.24-7.15 (m, 3H), 6.97 (d, J=8.3 Hz, 1H), 4.07 (s, 2H), 3.88 (brd, J=13.1 Hz, 2H), 3.55 (brd, J=19.6 Hz, 2H), 3.16 (brt, J=11.9 Hz, 2H), 2.29 (s, 3H), 1.91-1.79 (m, 2H), 1.76-1.56 (m, 2H).

Embodiment 46: Compound 46

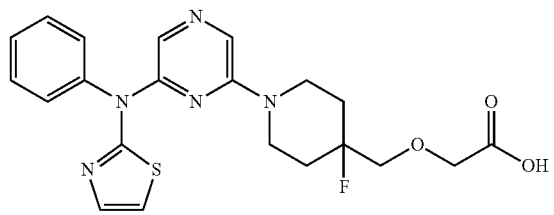 [SMILES: O=C(O)COCC1(F)CCN(c2cncc(N(c3ccccc3)c3nccs3)n2)CC1]

Synthetic Route:

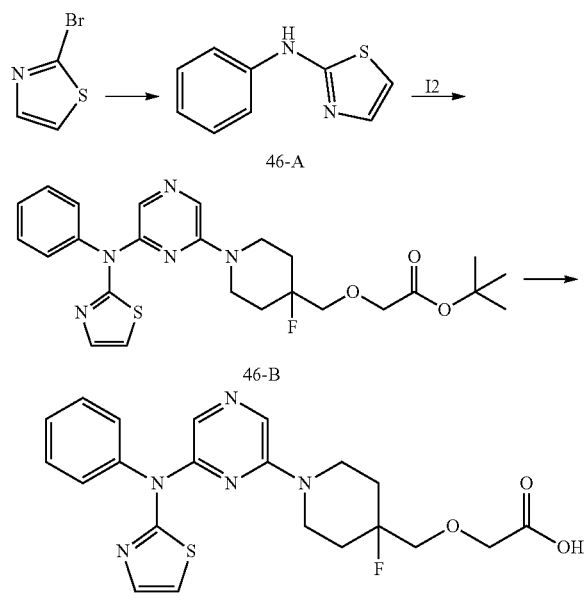

Step 1: Synthesis of Compound 46-A

Compound 2-bromothiazole (2 g, 12.19 mmol, 1.10 mL), aniline (1.70 g, 18.29 mmol, 1.67 mL), TsOH H$_2$O (1.16 g, 6.10 mmol) were dissolved in isopropanol (20 mL), and after the mixture was stirred at 80° C. for 72 hours under an atmosphere of nitrogen, the mixture was concentrated to obtain a crude product. The crude product was separated and purified by column chromatography (petroleum ether/ethyl acetate=10/1) to obtain compound 46-A.

MS m/z: 176.9 [M+H]$^+$.

Step 2: Synthesis of Compound 46-B

Except for using the corresponding raw materials, compound 46-B was prepared according to the same method as that of compound 3-B in the process of embodiment 3.

Step 3: Synthesis of Compound 46

Except for using the corresponding raw materials, compound 46 was prepared according to the same method as that of compound 3 in the process of embodiment 3.

MS m/z: 444.1 [M+H]$^+$.

$^1$H NMR (400 MHz, DMSO-d$_6$) δ ppm 7.96 (brs, 1H), 7.62-7.57 (m, 2H), 7.54-7.49 (m, 1H), 7.39 (brd, J=7.5 Hz, 2H), 7.31 (d, J=3.5 Hz, 1H), 7.20 (d, J=3.5 Hz, 1H), 6.89 (brs, 1H), 4.26 (brd, J=13.6 Hz, 2H), 4.08 (s, 2H), 3.65 (brs, 2H), 3.59 (brs, 2H), 1.93-1.73 (m, 4H).

Embodiment 47: Compound 47

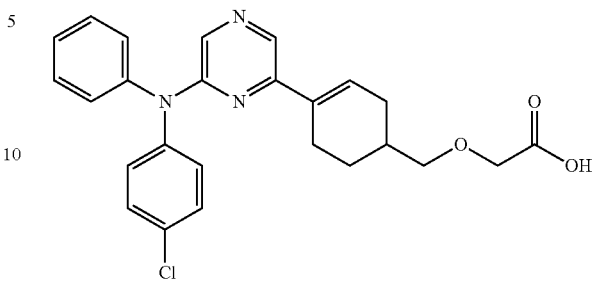

Synthetic Route:

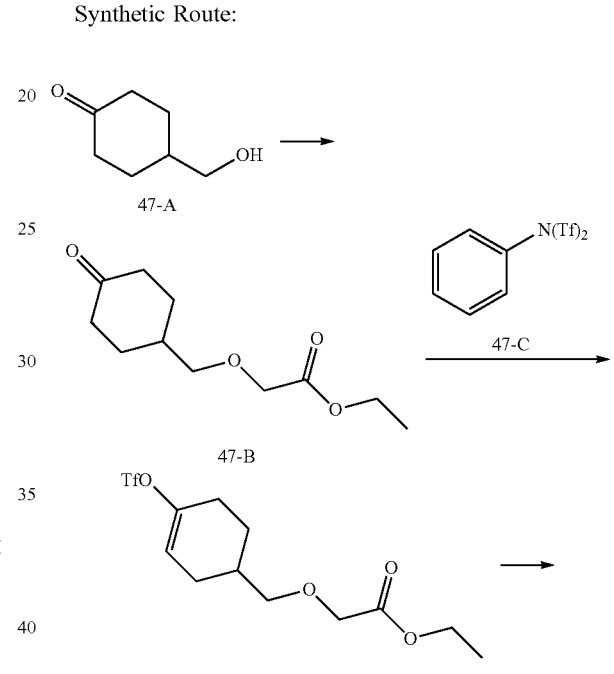

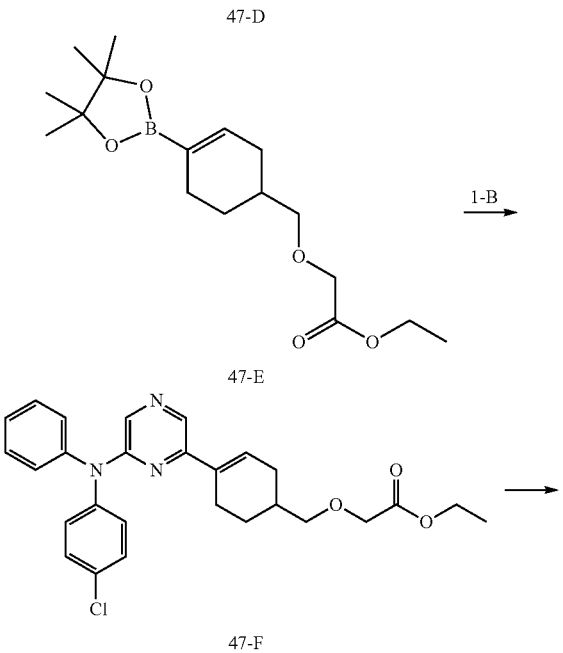

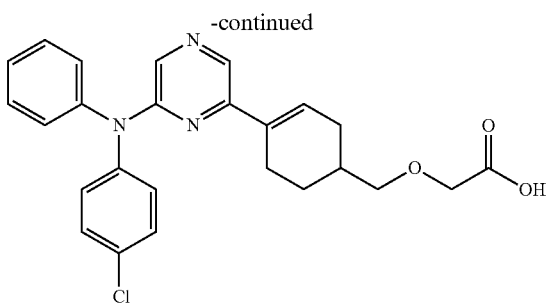

47

Step 1: Synthesis of Compound 47-B

To dichloromethane (30.00 mL) were added compound 47-A (2 g, 15.60 mmol) and rhodium acetate (344.84 mg, 1.56 mmol), and then a solution of ethyl diazoacetate (2.14 g, 18.73 mmol) in dichloromethane (30.00 mL) was added at 0° C. And after the completion of the addition, the reaction mixture was stirred at 0° C. for 0.5 hour. The reaction mixture was diluted with water (20 mL) and extracted with dichloromethane (40 mL), and the extract was washed with saturated brine (20 mL) and dried over anhydrous sodium sulfate. After the anhydrous sodium sulfate was filtered off, the solvent was removed under reduced pressure to obtain a crude product. The crude product was purified through a column chromatography machine (eluent: petroleum ether/ethyl acetate=10/1 to 4/1) to obtain 47-B.

Step 2: Synthesis of Compound 47-D

Compound 47-B (1.7 g, 7.93 mmol) was dissolved in tetrahydrofuran (30.00 mL), and LiHMDS (1 M, 9.52 mL) was added dropwise at −78° C. under nitrogen protection. And the reaction solution was stirred at −78° C. for 1 hour, and then a solution of compound 47-C (3.40 g, 9.52 mmol) in tetrahydrofuran (5 mL) was added dropwise. After half an hour, the dry ice acetone bath was removed, the temperature was raised to 20° C. and the reaction continued for 2 hours. The reaction mixture was diluted with water (20 mL) and extracted with ethyl acetate (40 mL). The extract was washed with saturated brine (20 mL) and dried over anhydrous sodium sulfate. After the anhydrous sodium sulfate was filtered off, the solvent was removed under reduced pressure to obtain a crude product. The crude product was purified by column chromatography (eluent: petroleum ether/ethyl acetate=20/1 to 10/1) to obtain 47-D.

Step 3: Synthesis of Compound 47-E

Compound 47-D (1 g, 2.89 mmol), bis(pinacolato)diboron (1.10 g, 4.33 mmol) and potassium acetate (708.47 mg, 7.22 mmol) were added to dioxane (20 mL), and to the mixture was added Pd(dppf)Cl$_2$·CH$_2$Cl$_2$ (235.80 mg, 288.75 µmol) under nitrogen protection, and the reaction solution was stirred at 80° C. for 12 hours under an atmosphere of nitrogen. The reaction solution was concentrated to obtain a crude product. The crude product was purified by column chromatography (eluent: petroleum ether/ethyl acetate=100/1 to 20/1) to obtain 47-E.

$^1$H NMR (400 MHz, CHLOROFORM-d) δ ppm 6.47 (br d, J=2.26 Hz, 1H), 4.15 (q, J=7.28 Hz, 2H), 3.99 (s, 2H), 3.34 (d, J=6.52 Hz, 2H), 2.11-2.23 (m, 2H), 1.98-2.08 (m, 1H), 1.70-1.92 (m, 3H), 1.20-1.24 (m, 4H), 1.19 (s, 12H).

Step 4: Synthesis of Compound 47-F

Compound 47-E (0.1 g, 308.43 µmol), 1-B (195.04 mg, 616.86 µmol) and sodium carbonate (65.38 mg, 616.86 µmol) were dissolved in dioxane (10 mL) and water (1 mL), and Pd(dppf)Cl$_2$·CH$_2$Cl$_2$ (25.19 mg, 30.84 µmol) was added under nitrogen protection, and the reaction solution was stirred at 110° C. for 12 hours under an atmosphere of nitrogen. The reaction solution was diluted with water (20 mL) and extracted with ethyl acetate (40 mL). The extract was washed with saturated brine (20 mL) and dried over anhydrous sodium sulfate. After the anhydrous sodium sulfate was filtered off, the solvent was removed under reduced pressure to obtain a crude product. The crude product was purified by a column chromatography machine (eluent: petroleum ether/tetrahydrofuran=3/1) to obtain 47-F.

MS m/z: 478.2 [M+H]$^+$.

$^1$H NMR (400 MHz, METHANOL-d$_4$) δ ppm 8.12 (s, 1H), 7.74 (s, 1H), 7.42-7.48 (m, 2H), 7.37 (d, J=8.78 Hz, 2H), 7.20-7.32 (m, 5H), 6.66 (brs, 1H), 4.22 (q, J=7.02 Hz, 2H), 4.12 (s, 2H), 3.47 (d, J=5.76 Hz, 2H), 2.19-2.57 (m, 4H), 1.90-2.01 (m, 3H), 1.28 (t, J=7.20 Hz, 3H).

Step 5: Synthesis of Compound 47

To a mixed solution of tetrahydrofuran (5 mL), methanol (5 mL) and water (3 mL) were added compound 47-F (0.03 g, 62.76 µmol) and lithium hydroxide monohydrate (7.90 mg, 188.29 µmol), and the reaction solution was stirred at 25° C. for 20 minutes under an atmosphere of nitrogen. The reaction solution was concentrated, and a crude product was dissolved in 5 mL water and the solution was adjusted the pH to 3 to 4 with 1N hydrochloric acid, and filtered to obtain compound 47.

MS m/z: 450.1 [M+H]$^+$.

$^1$H NMR (400 MHz, METHANOL-d$_4$) δ ppm 8.09 (s, 1H), 7.74 (s, 1H), 7.40-7.46 (m, 2H), 7.35 (d, J=8.76 Hz, 2H), 7.17-7.31 (m, 6H), 6.64 (brs, 1H), 4.08 (s, 2H), 3.47 (brd, J=5.76 Hz, 2H), 2.51 (brd, J=15.80 Hz, 1H), 2.22-2.45 (m, 2H), 1.98 (brd, J=12.80 Hz, 3H), 1.42 (brs, 1H).

Embodiment 48: Compound 48a, Compound 48b

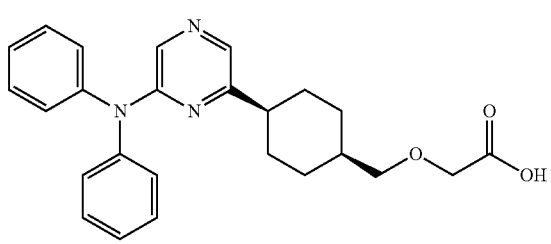

48a

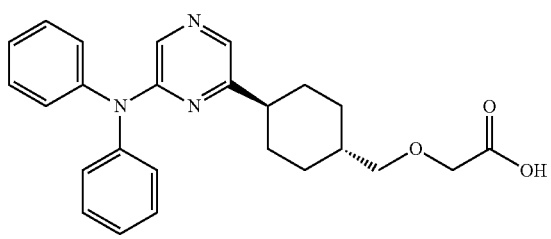

48b

Synthetic Route:

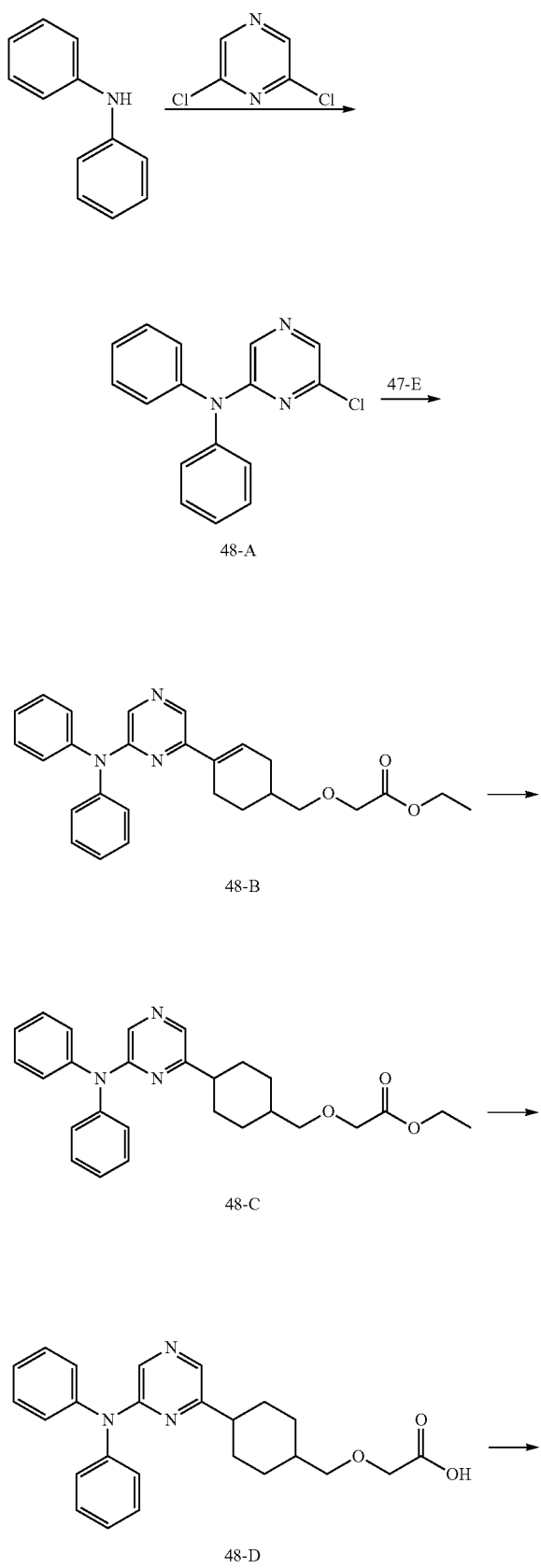

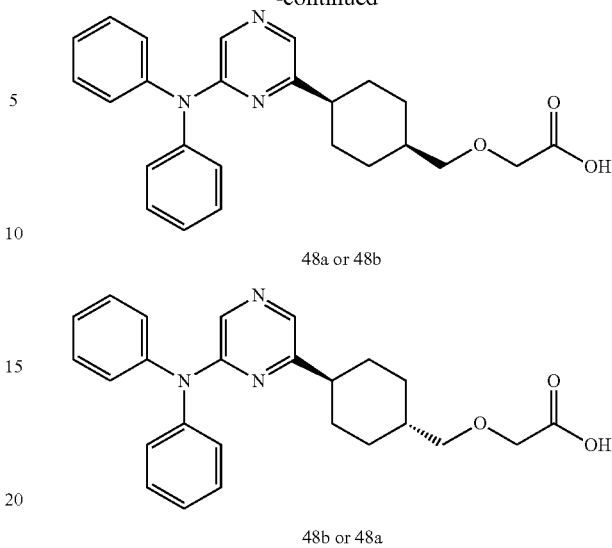

Step 1: Synthesis of Compound 48-A

Diphenylamine (5 g, 29.55 mmol, 4.31 mL) was dissolved in DMF (50 mL), the mixture was cooled to 0° C., and then was added with sodium hydrogen (2.36 g, 59.09 mmol, 60% purity). The reaction solution was stirred at 20° C. for 0.5 hour. And then 2,6-dichloropyrazine (5.28 g, 35.46 mmol) was added and the reaction solution was stirred at 20° C. for 2 hours. The reaction solution was diluted with water (50 mL) and extracted with ethyl acetate (100 mL). The extract was washed with saturated brine (50 mL) and dried over anhydrous sodium sulfate. After the anhydrous sodium sulfate was filtered off, the solvent was removed under reduced pressure to obtain a crude product. The crude product was purified by a column chromatography machine (eluent: petroleum ether/ethyl acetate=20/1 to 10:1) to obtain 48-A.

MS m/z: 281.9 [M+H]$^+$.

Step 2: Synthesis of Compound 48-B

Except for using the corresponding raw materials, compound 48-B was prepared according to the same method as that of compound 47-F in the process of embodiment 47.

MS m/z: 444.2 [M+H]$^+$.

Step 3: Synthesis of Compound 48-C

To a mixed solution of methanol (5 mL) and ethyl acetate (5 mL) were added compound 48-B (0.02 g, 45.09 μmol) and Pd/C (0.01 g, 45.09 μmol, 10% purity). The reaction solution was stirred at 20° C. for 2 hours under an atmosphere of $H_2$ (15 Psi).

The reaction solution was filtered and concentrated to obtain 48-C.

MS m/z: 446.0 [M+H]$^+$.

Step 4: Synthesis of Compound 48-D

Except for using the corresponding raw materials, compound 48-D was prepared according to the same method as that of compound 47 in the process of embodiment 47.

MS m/z: 418.1 [M+H]$^+$.

Step 5: Synthesis of Compound 48a, 48b

Compound 48 was separated by SFC (SFC method: separation column: AD (250 mm*30 mm, 10 μm); mobile phase: [0.1% $NH_3H_2O$ EtOH]; B %: 25%-25%, the minimum flow rate: 60 mL/min) to obtain compound 48a (retention time: 3.48 min) and 48b (retention time: 3.25 min).

For compound 48a:

MS m/z: 418.1 [M+H]+.

1H NMR (400 MHz, METHANOL-d4) δ ppm 7.73 (s, 1H), 7.62 (s, 1H), 7.24-7.30 (m, 4H), 7.08-7.14 (m, 6H), 3.94 (s, 2H), 3.26 (d, J=6.28 Hz, 2H), 2.45 (tt, J=12.12, 3.17 Hz, 1H), 1.73-1.86 (m, 4H), 1.45-1.58 (m, 1H), 1.39 (qd, J=12.92, 3.64 Hz, 2H), 0.94-1.07 (m, 2H).

For compound 48b:

MS m/z: 418.0 [M+H]+.

1H NMR (400 MHz, METHANOL-d4) δ ppm 7.73-7.76 (m, 1H), 7.62 (s, 1H), 7.24-7.30 (m, 4H), 7.08-7.14 (m, 6H), 3.90 (s, 2H), 3.24 (d, J=7.28 Hz, 2H), 2.64 (tt, J=8.16, 4.12 Hz, 1H), 1.58-1.75 (m, 3H), 1.35-1.56 (m, 6H).

Embodiment 49: Compound 49

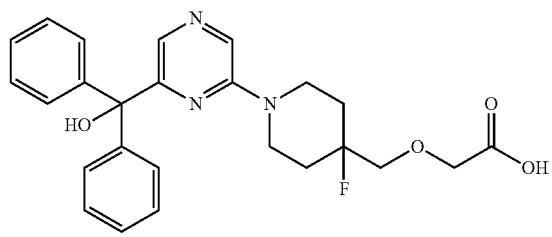 [SMILES: O=C(O)COCC1(F)CCN(c2cncc(C(O)(c3ccccc3)c3ccccc3)n2)CC1]

Synthetic Route:

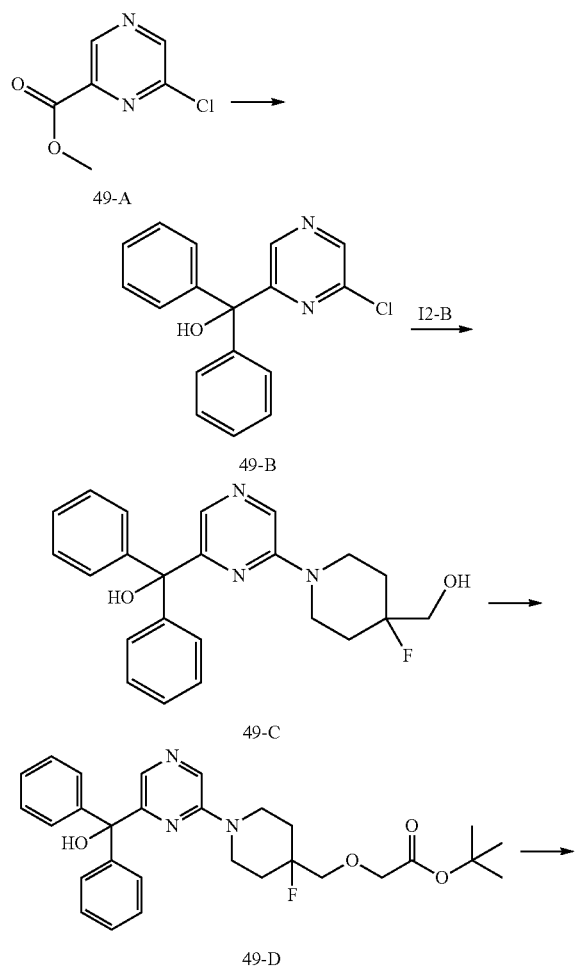

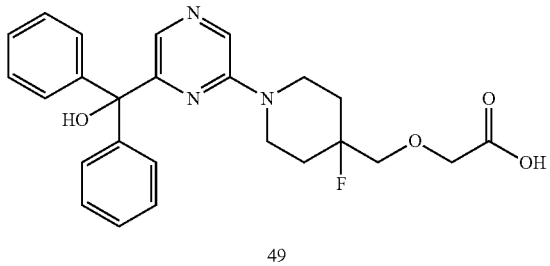

49

Step 1: Synthesis of Compound 49-B

To a solution of compound 49-A (0.2 g, 1.16 mmol) in tetrahydrofuran (20 mL) was added phenyl Grignard reagent (3 M, 772.64 L) at −10 to 0° C., and the reaction solution was stirred at 20° C. to 25° C. for 12 hours. The reaction system was diluted with water (20 mL) and extracted with ethyl acetate (30 mL*3). The combined extract was washed with saturated brine (20 mL), dried over anhydrous sodium sulfate, filtered, and the filtrate was concentrated under vacuum to obtain a crude product. The crude product was separated by preparative thin layer chromatography (petroleum ether/tetrahydrofuran=10/1 to 3/1) to obtain compound 49-B.

MS m/z: 296.9 [M+H]+.

Step 2: Synthesis of Compound 49-C

Compound 49-B (0.1 g, 336.98 μmol) and I2-B (85.74 mg, 505.48 μmol) were uniformly mixed with DMF (10 mL), and to the reaction system was added cesium carbonate (329.39 mg, 1.01 mmol), and the reaction solution was stirred at 130° C. for 2 hours. The solvent was removed under reduced pressure, and the residue was separated by column chromatography (petroleum ether/tetrahydrofuran=10/1 to 3/1) to obtain compound 49-C.

MS m/z: 394.1 [M+H]+.

Step 3: Synthesis of Compound 49-D

Except for using the corresponding raw materials, compound 49-D was prepared according to the same method as that of compound I1 in the process of intermediate I1.

MS m/z: 508.2 [M+H]+.

Step 4: Synthesis of Compound 49

Except for using the corresponding raw materials, compound 49 was prepared according to the same method as that of compound 3 in the process of embodiment 3.

MS m/z: 452.0 [M+H]+.

1H NMR (400 MHz, CHLOROFORM-d) δ ppm 8.04 (s, 1H), 7.52 (s, 1H), 7.23 (brd, J=3.0 Hz, 10H), 4.12 (s, 4H), 3.56 (brd, J=19.6 Hz, 2H), 3.31-3.21 (m, 2H), 1.95 (brs, 2H), 1.78-1.51 (m, 2H).

Embodiment 50: Compound 50

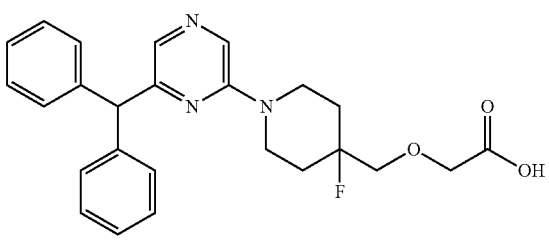 [SMILES: O=C(O)COCC1(F)CCN(c2cncc(C(c3ccccc3)c3ccccc3)n2)CC1]

Synthetic Route:

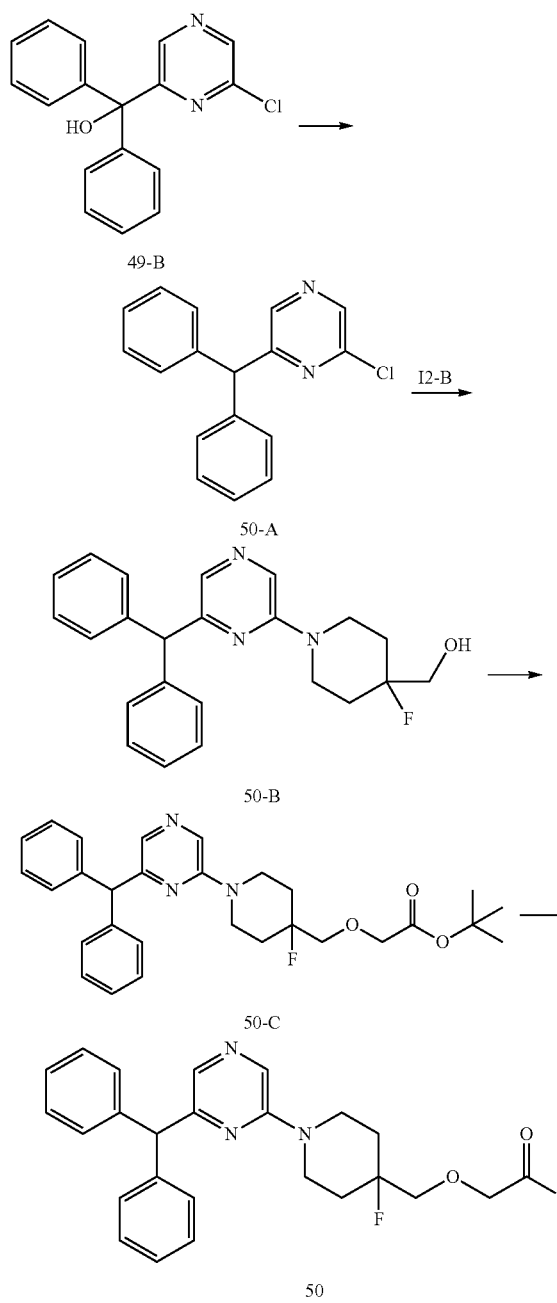

Step 1: Synthesis of Compound 50-A

49-B (0.6 g, 2.02 mmol) was dissolved in TFA (8 mL), and triethylsilane (2.91 g, 25.04 mmol, 4 mL) was added, and the reaction mixture was stirred at 20° C. for 0.5 hour. The reaction mixture was concentrated to obtain a crude product. The crude product was separated and purified by column chromatography (petroleum ether/ethyl acetate=20/1) to obtain compound 50-A.

MS m/z: 280.9 [M+H]$^+$.

Step 2: Synthesis of Compound 50-B

Except for using the corresponding raw materials, compound 50-B was prepared according to the same method as that of compound 49-C in the process of embodiment 49.

MS m/z: 378.1 [M+H]$^+$.

Step 3: Synthesis of Compound 50-C

Except for using the corresponding raw materials, compound 50-C was prepared according to the same method as that of compound I1 in the process of intermediate I1.

MS m/z: 492.2 [M+H]$^+$.

Step 4: Synthesis of Compound 50

Except for using the corresponding raw materials, compound 50 was prepared according to the same method as that of compound 3 in the process of embodiment 3.

MS m/z: 436.2 [M+H]$^+$.

$^1$H NMR (400 MHz, CHLOROFORM-d) δ ppm 7.94 (brs, 1H), 7.61 (s, 1H), 7.24-7.17 (m, 5H), 7.15-7.12 (m, 1H), 5.35 (s, 1H), 4.14-3.99 (m, 4H), 3.52 (brd, J=18.8 Hz, 2H), 3.20 (brt, J=12.0 Hz, 2H), 1.87 (brd, J=10.3 Hz, 2H), 1.70-1.51 (m, 2H).

Embodiment 51: Compound 51

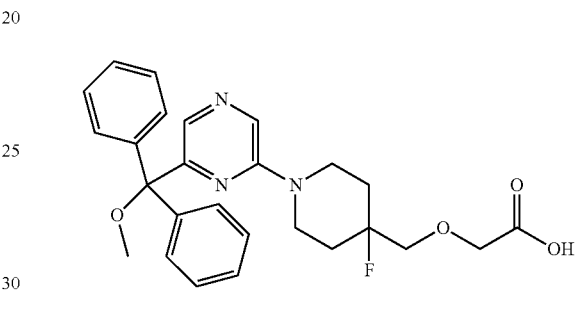

Synthetic Route:

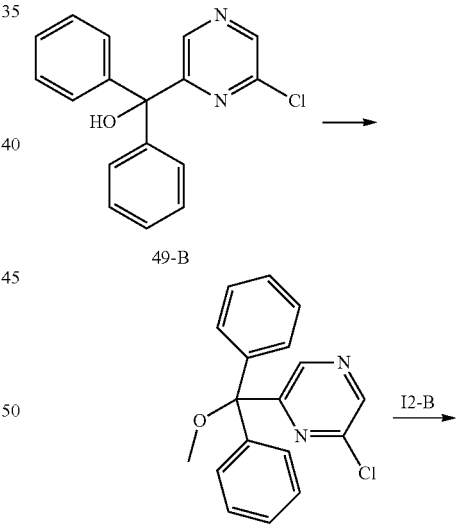

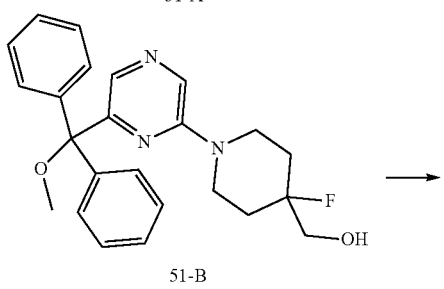

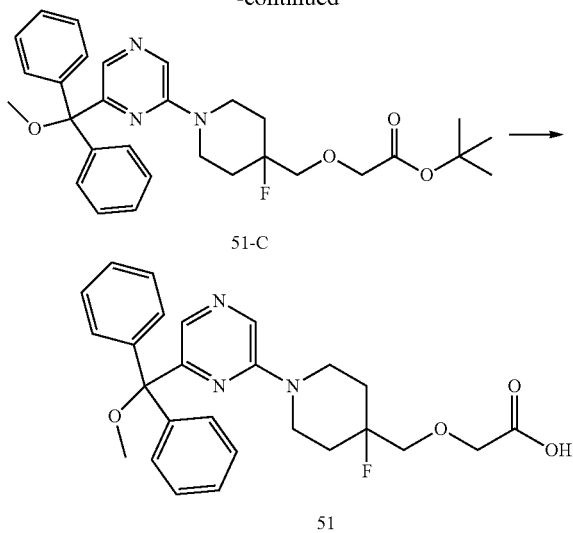

Step 1: Synthesis of Compound 51-A

49-B (0.6 g, 2.02 mmol) was dissolved in anhydrous tetrahydrofuran (5 mL), and sodium hydride was added (121.30 mg, 3.03 mmol, 60% purity) in portions at 0° C. After the completion of the addition, the mixture was further stirred for 0.5 hours, and iodomethane was added dropwise at 0° C. After the reaction mixture was further stirred at 20° C. for 1 hour, the reaction mixture was concentrated to obtain a crude product. The crude product was separated and purified by column chromatography (petroleum ether/ethyl acetate=20/1) to obtain compound 51-A.

MS m/z: 310.9 [M+H]$^+$.

Step 2: Synthesis of Compound 51-B

Except for using the corresponding raw materials, compound 51-B was prepared according to the same method as that of compound 49-C in the process of embodiment 49.

MS m/z: 408.1 [M+H]$^+$.

Step 3: Synthesis of Compound 51-C

Except for using the corresponding raw materials, compound 51-C was prepared according to the same method as that of compound I1 in the process of intermediate I1.

MS m/z: 522.2 [M+H]$^+$.

Step 4: Synthesis of Compound 51

Except for using the corresponding raw materials, compound 51 was prepared according to the same method as that of compound 3 in the process of embodiment 3.

MS m/z: 466.2 [M+H]$^+$.

$^1$H NMR (400 MHz, CHLOROFORM-d) δ ppm 8.25 (s, 1H), 8.03 (s, 1H), 7.45-7.38 (m, 4H), 7.32-7.24 (m, 6H), 4.23-4.13 (m, 2H), 4.04 (brd, J=13.6 Hz, 2H), 3.58 (d, J=19.6 Hz, 2H), 3.25 (brt, J=11.7 Hz, 2H), 3.11 (s, 3H), 2.00-1.84 (m, 2H), 1.76-1.51 (m, 2H).

Experimental Embodiment 1: Evaluation In Vitro

PGI$_2$ cAMP Cell Assay In Vitro:

1. Preparation of PGI$_2$ Cell Suspension:

A series of cells were placed in a 37° C. water bath for rapid thawing, and the cell suspension was transferred to a 15 mL centrifuge tube containing 10 mL HBSS, and mixed uniformly. The cells were centrifuged at 1000 rpm for 5 minutes at room temperature. The supernatant was removed after centrifugation.

The centrifuge tube was tapped gently to suspend the cells after centrifugation, then the cells were re-suspended with 10 mL HBSS (Hanks buffered saline solution) and mixed uniformly by pipetting up and down. The cells were counted by Vi-cell. The cells were centrifuged for the second time at 1000 rpm for 5 minutes. The cells were re-suspended by experimental buffer to reach a cell concentration of 1.5× 105/mL.

2. Preparation of the Sample:

The samples were diluted with the Bravo automated liquid handling platform to make the initial concentration of the sample reach 2 mM and 5-fold serial dilution at 10 points. The control sample was diluted with Bravo to make the initial concentration of the sample reach 2 mM and 5-fold serial dilution at 10 points.

3. HTRF cAMP Experimental Steps:

50 nL DMSO or sample to be tested was transferred to PE384-well OptiPlate by Echo. The cell suspension was transferred to the testing plate by electric pipette, 10 μL cells/well. The testing plate was centrifuged at 1000 rpm for seconds. The testing plate was incubated at room temperature for 60 minutes. Two kinds of test reagents were added to the testing plate, 5 L/well. The testing plate was centrifuged at 1000 rpm for 1 minute. The experimental plate was sealed with Top Seal-A film and incubated at room temperature for 60 minutes. TopSeal-A was removed and the value was read on EnVision.

TABLE 1

Results of activity of the compound of the present invention on cell in vitro assay (EC$_{50}$)

| No. | PGI$_2$ (EC$_{50}$ nM) |
|---|---|
| 1 | 2.02 |
| 2 | 2988.00 |
| 3 | 2.09 |
| 4 | 2.99 |
| 5 | 3.74 |
| 6 | 3.55 |
| 7 | 2.12 |
| 8 | 37.99 |
| 9 | 12.78 |
| 10 | 10.15 |
| 11 | 123.20 |
| 12 | 4.84 |
| 13 | 4.17 |
| 14 | 9.65 |
| 15 | >2000 |
| 16 | 23.52 |
| 17 | 0.29 |
| 18 | 79.92 |
| 19 | 6.11 |
| 20 | 1.65 |
| 21 | 3.00 |
| 22 | 0.22 |
| 23 | 1.10 |
| 24 | 0.41 |
| 25 | 0.80 |
| 26 | 3.73 |
| 27 | 6.74 |
| 28 | 2.17 |
| 29 | 4.19 |
| 30 | 3.26 |
| 31 | 1.61 |
| 32 | 1.41 |
| 33 | 118.20 |
| 34 | 1.90 |

TABLE 1-continued

Results of activity of the compound of the present
invention on cell in vitro assay ($EC_{50}$)

| No. | $PGI_2$ ($EC_{50}$ nM) |
|---|---|
| 35 | 0.43 |
| 36 | 4.97 |
| 37 | 34.22 |
| 38 | 458.9 |
| 39 | >300 |
| 40 | 3.2 |
| 41 | 2.94 |
| 42 | 2.63 |
| 43 | 1.07 |
| 44 | 1.98 |
| 45 | 1.55 |
| 46 | 20.08 |
| 47 | 40.07 |
| 48a | 17.97 |
| 48b | 3.72 |
| 49 | 80.96 |
| 50 | 5.36 |
| 51 | 322.00 |

Experimental conclusion: the compounds of the present invention have good activity on $PGI_2$ cAMP on cells in vitro.

Experimental Embodiment 2: Evaluation of Drug Efficacy

1. Purpose of the Experiment

The rats having monocrotaline (MCT, model)-induced pulmonary arterial hypertension was intervened by using the compound to be tested, the effect of the compound to be tested on the pulmonary artery pressure and right ventricular function in rats was observed, and the possible mechanism thereof was explored.

2. Design of the Experimental 2.1 Establishment of Model of Pulmonary Arterial Hypertension of Rat At a dose volume of 2 ml/kg, MCT (60 mg/kg) was injected subcutaneously to induce a pulmonary arterial hypertension model. And the intragastric administration was started on the day of MCT subcutaneous injection, and various indexes were measured after three weeks of intragastric administration.

2.2 Group of Animals

After one-week acclimatization, animals were randomly divided into groups based on body weight and animal status: Sham (negative control group), Vehicle (modeling group), compound 32-5 mpk, compound 32-10 mpk, compound 32-30 mpk, compound 35-2 mpk, compound 35-5 mpk.

2.3 Group and Administration Information 2.4 Monitoring Indicators

1). The general state and weight of the animals were monitored every day;

2). The right ventricular systolic pressure (RVSP) was observed;

3). The right ventricular hypertrophy index (RVHI) was measured: right ventricular weight/(left ventricular weight+ interventricular septum weight);

2.5 Experimental Methods 2.5.1 Right Heart Catheterization Method to Measure Rat RVSP The rats were anesthetized with 2.5% pentobarbital sodium (2 ml/kg, ip), and the animals were fixed in the supine position on the surgical board. The neck fur was removed, the neck skin was cut, the subcutaneous tissue and muscle layer were bluntly separated bluntly, and the left carotid and right jugular vein were peeled off. The right external jugular vein was inserted with a rat dedicated right heart catheter (PE tube, outer diameter is about 1.5 mm, the front end is a small arc) which is filled with 0.3% sodium heparin solution and connected to the pressure transducer. During operation, the arc of the pulmonary artery catheter was kept downward, and the pulmonary artery catheter was extended to the direction of the right atrium. According to the pressure waveform, it was judged whether it reached the heart site, and the catheter was rotated toward left and advanced into the right ventricle.

2.5.2 Measurement of RVHI

The heart was taken out, the atrium and large blood vessels were removed, filter paper soaked up water, the right ventricle was peeled off, and weighed. RVHI=RV/(LV+SEP) was calculated.

RVHI: right ventricular hypertrophy index

RV: weight of right ventricular

LV+SEP: weight of left ventricle and interventricular septum

3. Experimental Results and Conclusions

Figure 2:
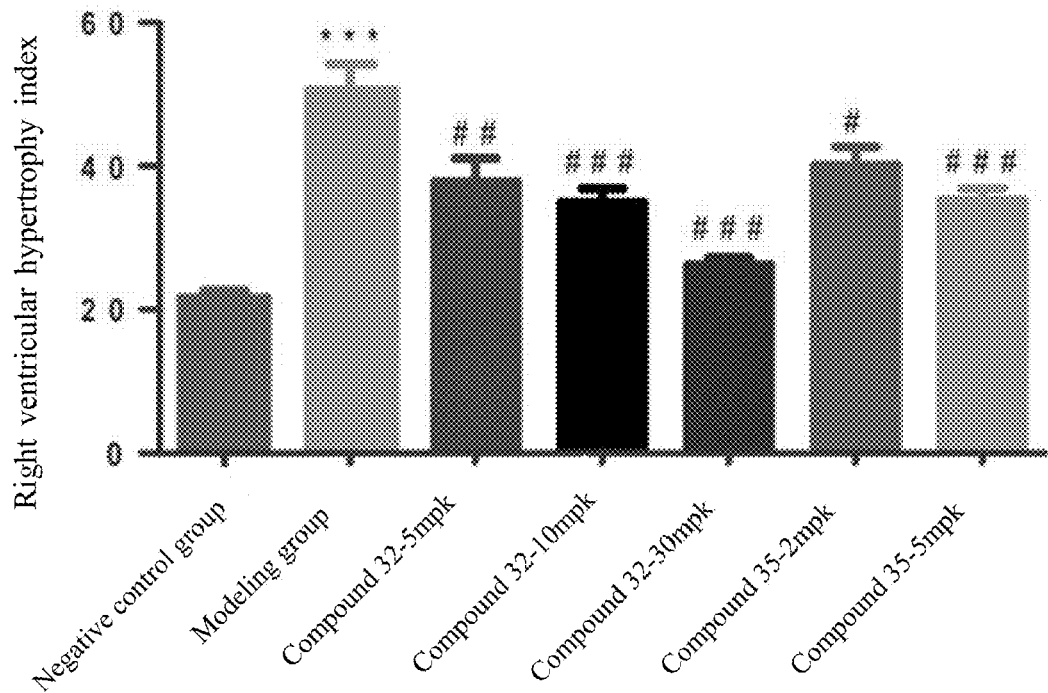
FIG. 2 shows the effect of the compound of the present disclosure on the right ventricle hypertrophy (RVHI) in the rat model of MCT (monocrotaline)-induced pulmonary arterial hypertension.

The results were shown in FIG. 1 and FIG. 2.

Experimental conclusions: the compound of the present invention significantly relieved the mean right ventricular systolic pressure (mRVSP), and relieved the right ventricular hypertrophy index (RVHI) significantly as well, and had a good dose correlation. Therefore, it could be explained that the compound of the present invention had obvious effects on the disease of pulmonary arterial hypertension in rats body.

| Group | Number of animals | Drug | Administration dose (mg/kg) | Administration concentration (mg/ml) | Administration time (day) |
|---|---|---|---|---|---|
| Sham (negative control group) | 8 | Solvent | — | — | D1-D24 |
| Vehicle (modeling group) | 8 | Solvent | — | — | D1-D24 |
| Compound 32-5mpk | 8 | Compound 32 | 5 | 1 | D1-D24 |
| Compound 32-10mpk | 8 | Compound 32 | 10 | 2 | D1-D24 |
| Compound 32-30mpk | 8 | Compound 32 | 30 | 6 | D1-D24 |
| Compound 35-2mpk | 8 | Compound 35 | 2 | 0.4 | D1-D24 |
| Compound 35-5mpk | 8 | Compound 35 | 5 | 1 | D1-D24 |

What is claimed is:

1. A compound represented by formula (I), an isomer or a pharmaceutically acceptable salt thereof,

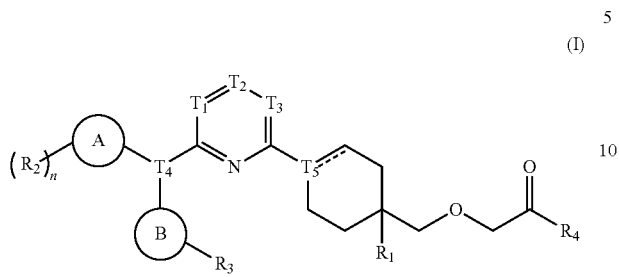

wherein, n is 1 or 2;

$R_1$ is H or F;

each of $R_2$ is independently selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_b$;

each of $R_b$ is independently selected from the group consisting of F, Cl, Br, I, OH and $NH_2$;

$R_3$ is selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_c$;

each of $R_c$ is independently selected from the group consisting of F, Cl, Br, I, OH and $NH_2$;

$R_4$ is selected from the group consisting of OH, $C_{1-6}$ alkoxy and $C_{1-6}$ alkyl-S(=O)$_2$—NH—, wherein $C_{1-6}$ alkoxy and $C_{1-6}$ alkyl-S(=O)$_2$—NH— are optionally substituted by one, two or three of $R_d$;

each of $R_d$ is independently selected from the group consisting of F, Cl, Br, I, OH and $NH_2$;

ring A is a phenyl or a 5- to 6-membered heteroaryl;

ring B is a phenyl, a 5- to 6-membered heteroaryl, a $C_{3-6}$ cycloalkyl or a 3- to 6-membered heterocycloalkyl;

$T_1$ is N or CH;

$T_2$ is N or CH;

$T_3$ is N or CH;

$T_4$ is N or C($R_5$);

$T_5$ is N, CH or C;

$R_5$ is selected from the group consisting of H, OH, $NH_2$, halogen, $C_{1-6}$ alkyl and $C_{1-6}$ heteroalkyl, wherein $C_{1-6}$ alkyl and $C_{1-6}$ heteroalkyl are optionally substituted by one, two or three of $R_e$;

each of $R_e$ is independently selected from the group consisting of F, Cl, Br, I, OH and $NH_2$;

each of $C_{1-6}$ heteroalkyl, 3- to 6-membered heterocycloalkyl and 5- to 6-membered heteroaryl respectively contains one, two or three of heteroatoms or heteroatomic groups independently selected from the group consisting of —O—, —NH—, —S— and N.

2. The compound represented by formula (I), the isomer or the pharmaceutically acceptable salt thereof as defined in claim 1, wherein each of $R_2$ is independently selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_b$;

preferably, each of $R_2$ is independently selected from the group consisting of H, F, Cl, Br, I, OH, $NH_2$, Me and

wherein Me and

are optionally substituted by one, two or three of $R_b$;

preferably, each of $R_2$ is independently selected from the group consisting of H, F, Cl, Br, I, OH, $NH_2$, Me, $CF_3$,

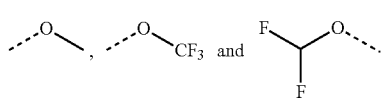

3. The compound represented by formula (I), the isomer or the pharmaceutically acceptable salt thereof as defined in claim 1, wherein $R_3$ is selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_c$;

preferably, $R_3$ is selected from the group consisting of H, F, Cl, Br, I, OH, $NH_2$, Me and

wherein Me and

are optionally substituted by one, two or three of $R_c$;

preferably, $R_3$ is selected from the group consisting of H, F, Cl, Br, I, OH, $NH_2$, Me, $CF_3$,

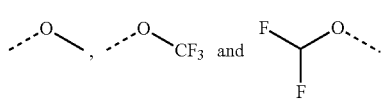

4. The compound represented by formula (I), the isomer or the pharmaceutically acceptable salt thereof as defined in claim 1, wherein $R_4$ is selected from the group consisting of OH, $C_{1-3}$ alkoxy and $C_{1-3}$ alkyl-S(=O)$_2$—NH—, wherein $C_{1-3}$ alkoxy and $C_{1-3}$ alkyl-S(=O)$_2$—NH— are optionally substituted by one, two or three of $R_d$;

preferably, $R_4$ is selected from the group consisting of OH,

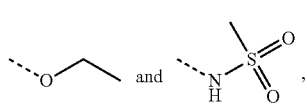

wherein

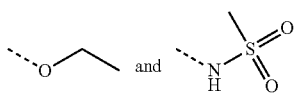

are optionally substituted by one, two or three of $R_d$; preferably, $R_4$ is selected from the group consisting of OH,

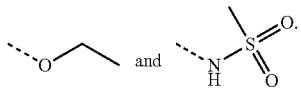

5. The compound represented by formula (I), the isomer or the pharmaceutically acceptable salt thereof as defined in claim 1, wherein $R_5$ is selected from the group consisting of H, OH, $NH_2$, halogen, $C_{1-3}$ alkyl and $C_{1-3}$ alkoxy, wherein $C_{1-3}$ alkyl and $C_{1-3}$ alkoxy are optionally substituted by one, two or three of $R_e$;
preferably, $R_5$ is selected from the group consisting of H, OH, $NH_2$, F, Cl, Br, I, Me and

, wherein Me and

are optionally substituted by one, two or three of $R_e$; preferably, $R_5$ is selected from the group consisting of H, OH, $NH_2$, F, Cl, Br, I, Me and

.

6. The compound represented by formula (I), the isomer or the pharmaceutically acceptable salt thereof as defined in claim 1, wherein $T_1$ is CH, $T_2$ is CH and $T_3$ is CH; alternatively, $T_1$ is N, $T_2$ is CH and $T_3$ is CH.

7. The compound represented by formula (I), the isomer or the pharmaceutically acceptable salt thereof as defined in claim 1, wherein $T_1$ is CH, $T_2$ is N, $T_3$ is CH.

8. The compound represented by formula (I), the isomer or the pharmaceutically acceptable salt thereof as defined in claim 1, wherein $T_1$ is CH, $T_2$ is CH, $T_3$ is N.

9. The compound represented by formula (I), the isomer or the pharmaceutically acceptable salt thereof as defined in claim 1, wherein the ring A is a phenyl or a pyridyl.

10. The compound represented by formula (I), the isomer or the pharmaceutically acceptable salt thereof as defined in claim 9, wherein the structure moiety

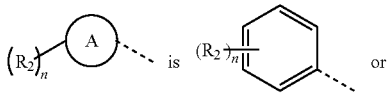

11. The compound represented by formula (I), the isomer or the pharmaceutically acceptable salt thereof as defined in claim 10, wherein the structure moiety

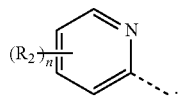

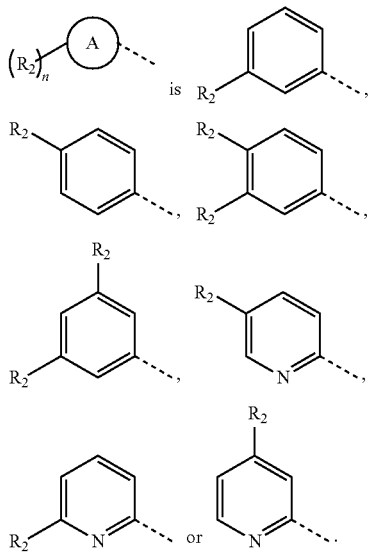

12. The compound represented by formula (I), the isomer or the pharmaceutically acceptable salt thereof as defined in claim 11, wherein the structure moiety

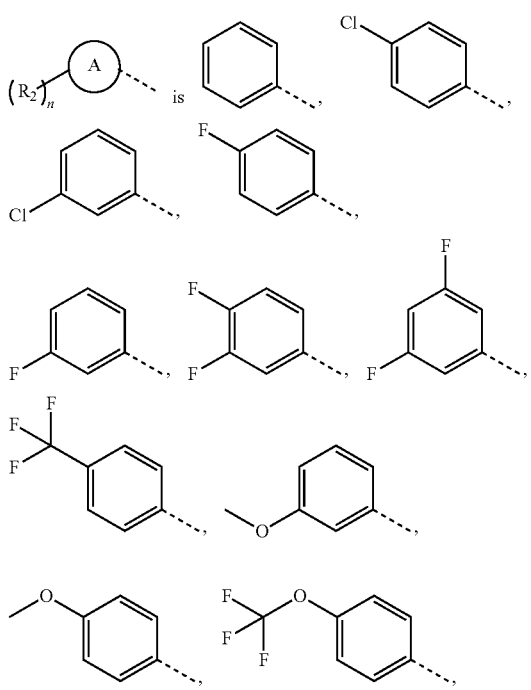

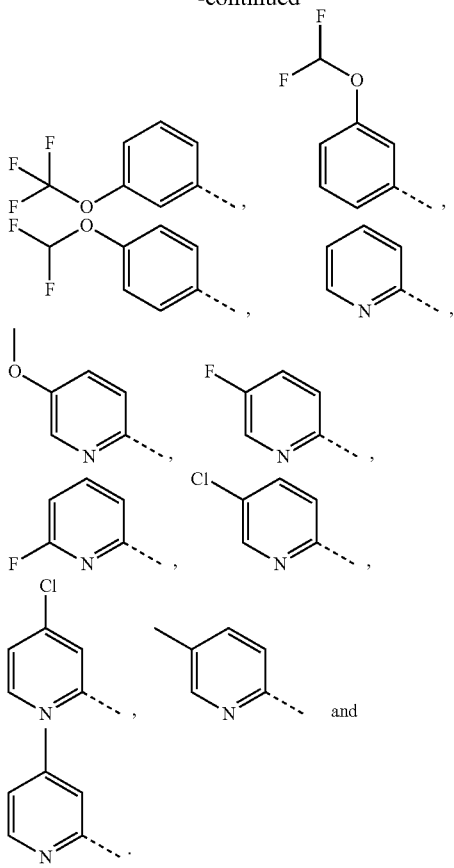

13. The compound represented by formula (I), the isomer or the pharmaceutically acceptable salt thereof as defined in claim 1, wherein ring B is a phenyl, a pyridyl, a thiazolyl or a cyclohexyl.

14. The compound represented by formula (I), the isomer or the pharmaceutically acceptable salt thereof as defined in claim 13, wherein the structure moiety

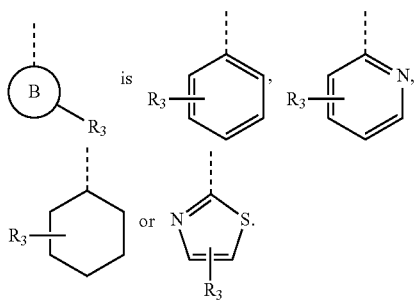

15. The compound represented by formula (I), the isomer or the pharmaceutically acceptable salt thereof as defined in claim 14, wherein the structure moiety

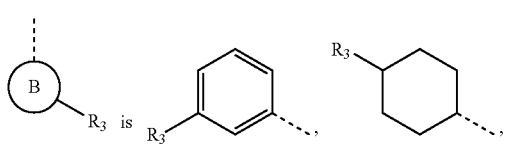

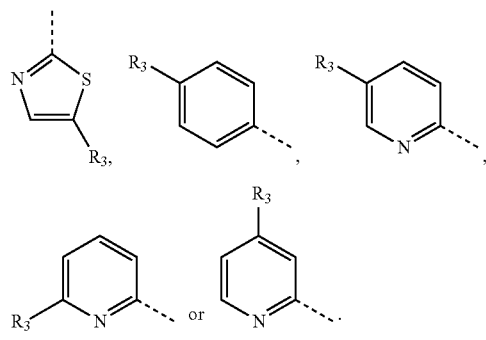

16. The compound represented by formula (I), the isomer or the pharmaceutically acceptable salt thereof as defined in claim 15, wherein the structure moiety

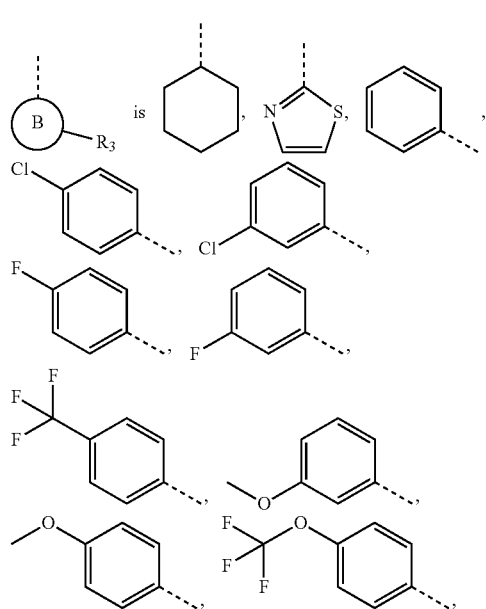

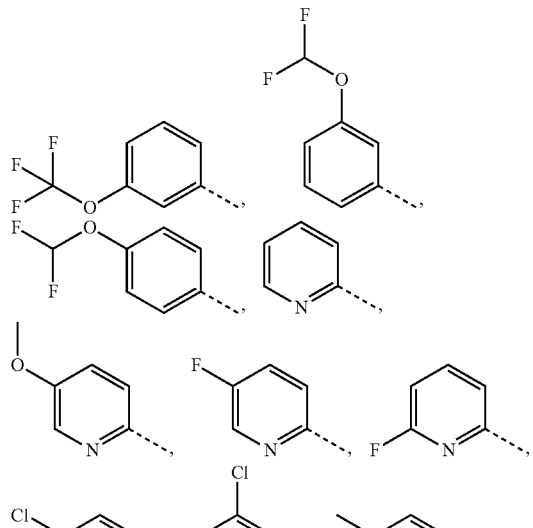

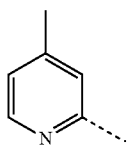
17. The compound represented by formula (I), the isomer or the pharmaceutically acceptable salt thereof as defined in claim 1, which is selected from the group consisting of
(I-1)
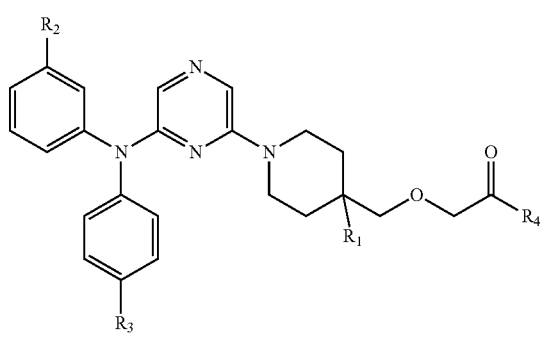
(I-2)
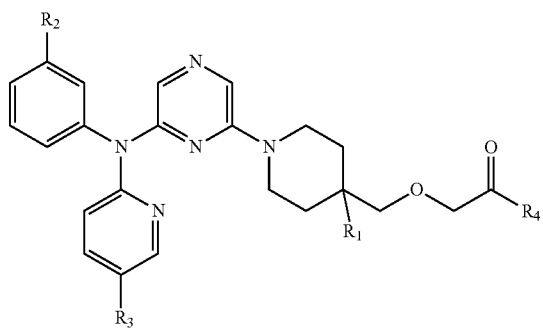
(I-3)
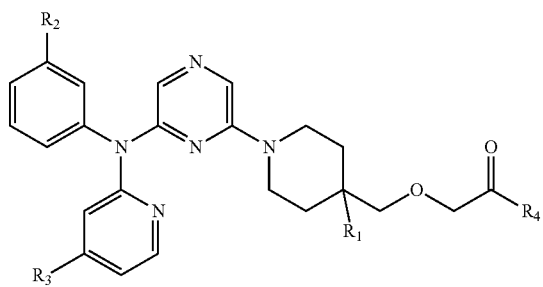
(I-4)
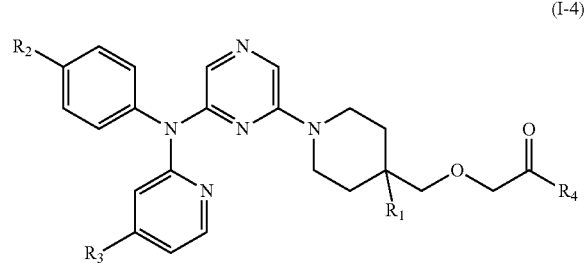
(I-5)
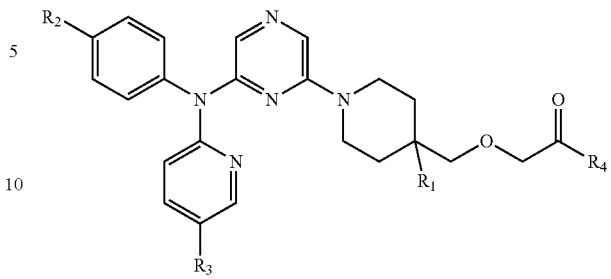
(I-6)
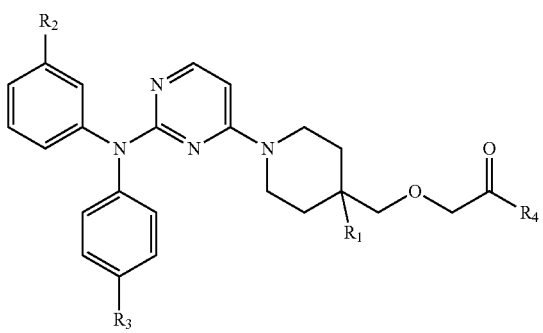
(I-7)
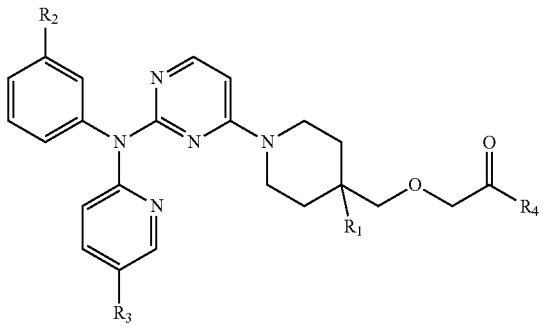
(I-8)
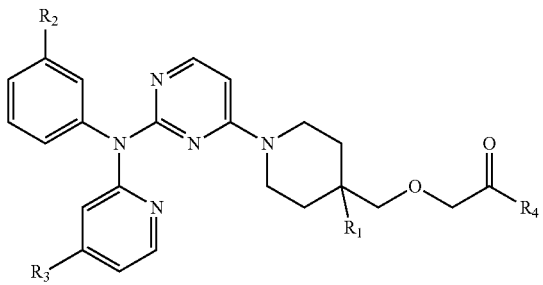
(I-9)
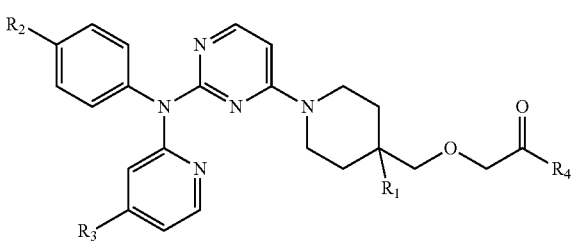

-continued
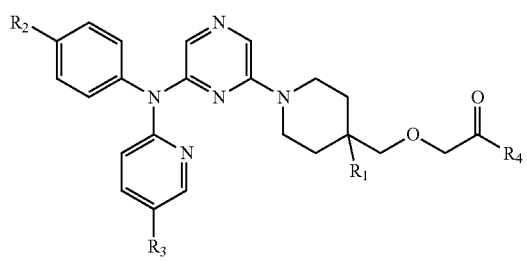
(I-10)
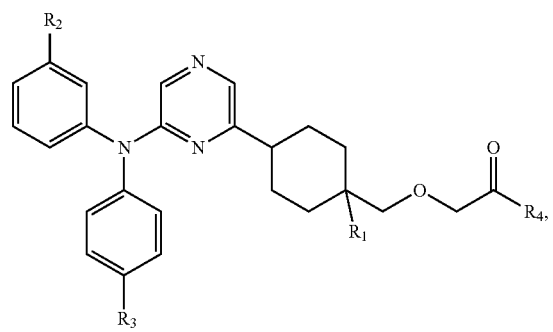
and
(I-11)
wherein,
R₁, R₂, R₃ and R₄ are defined in claim 1.
18. A compound, an isomer or a pharmaceutically acceptable salt thereof, which is selected from the group consisting of
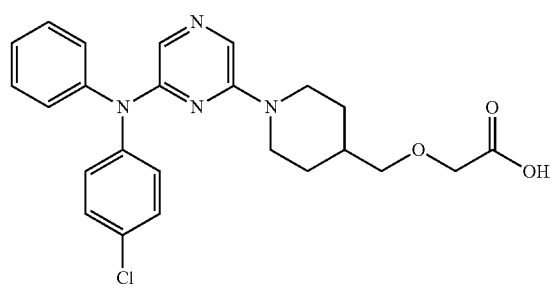
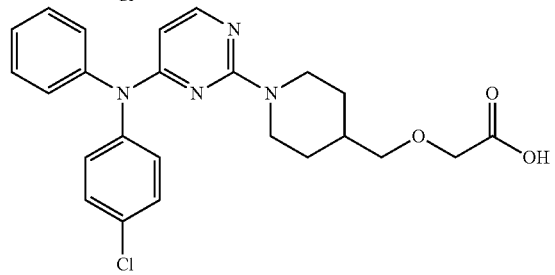
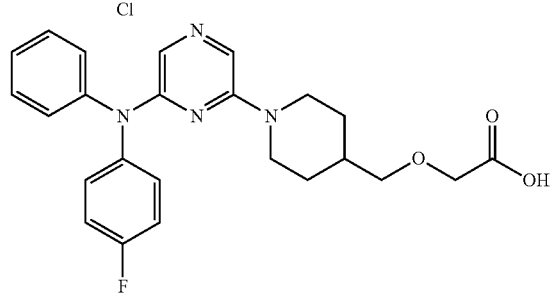
-continued
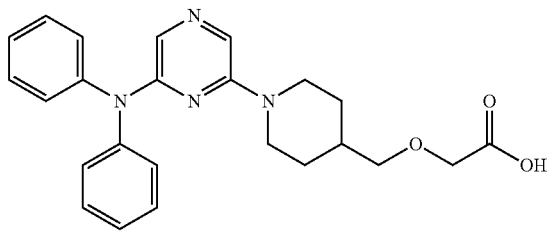
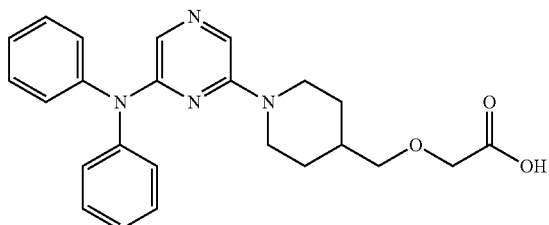
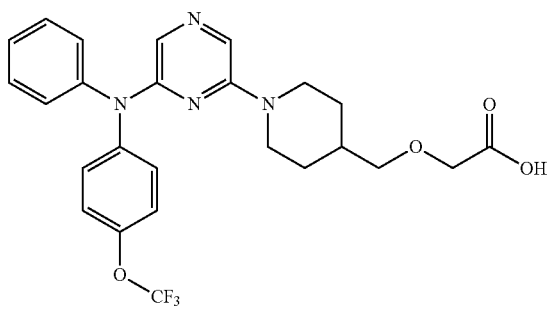
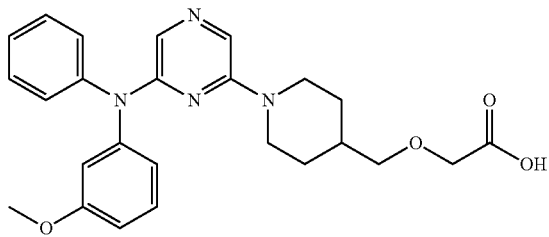
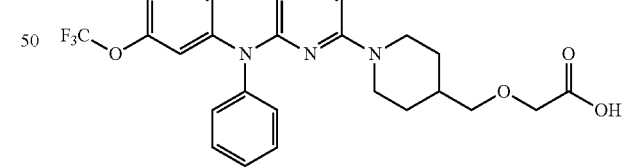
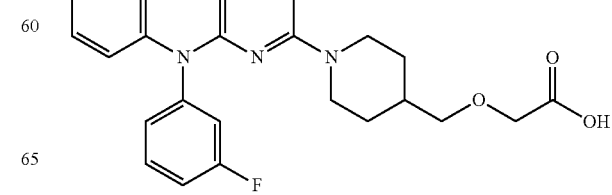

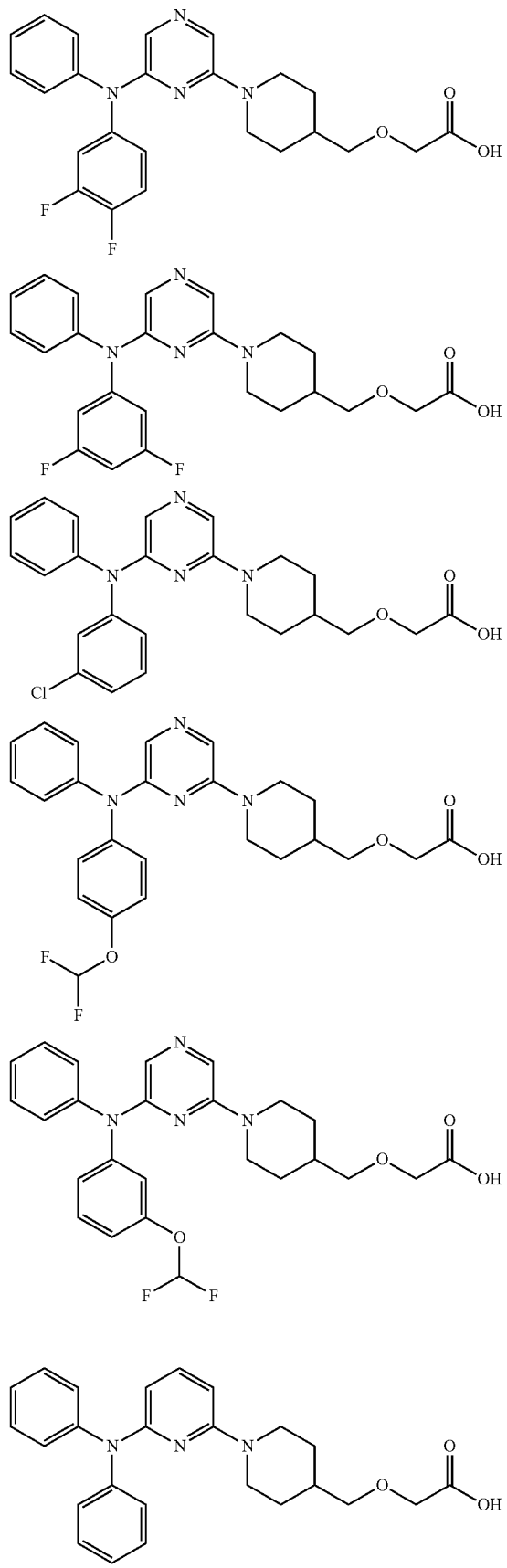
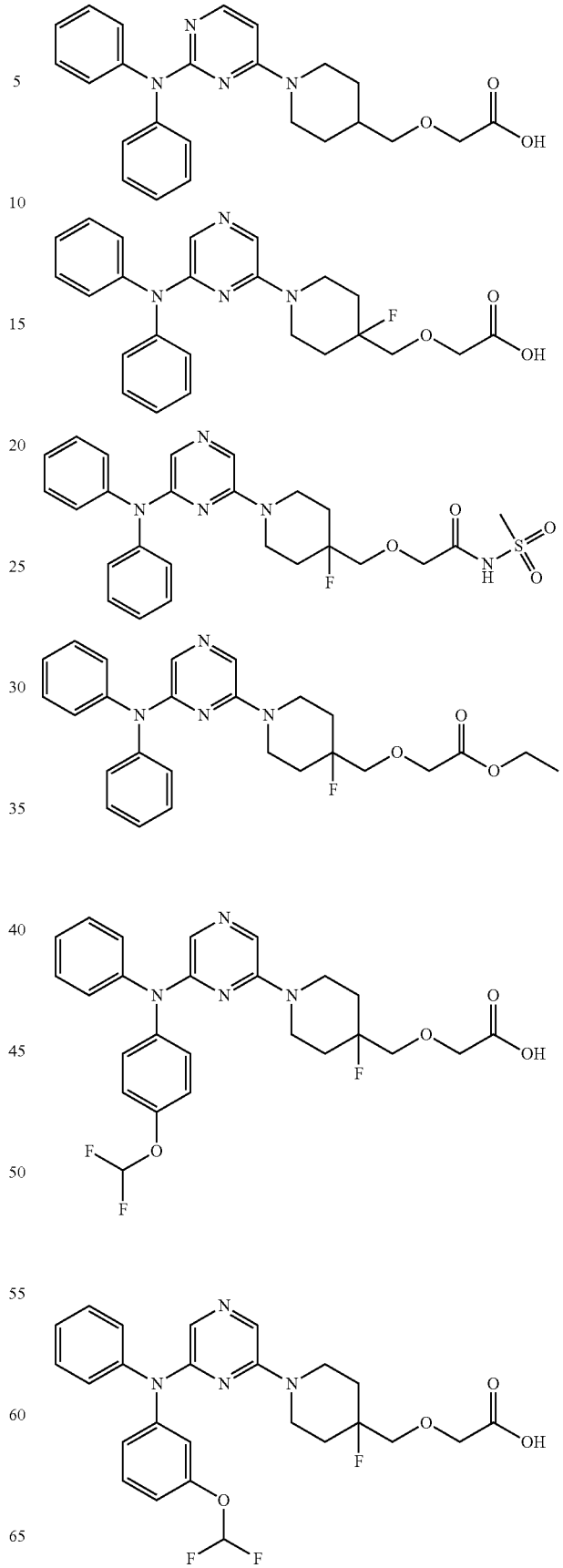

111
-continued
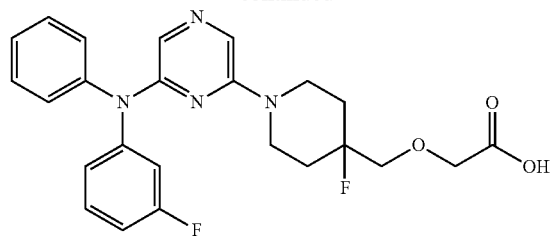
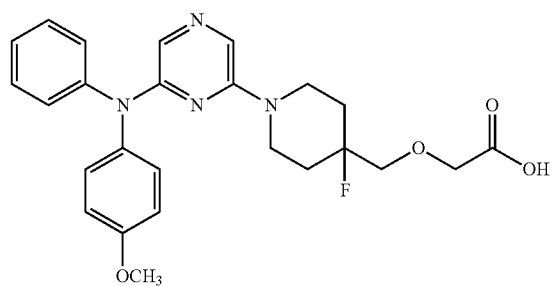
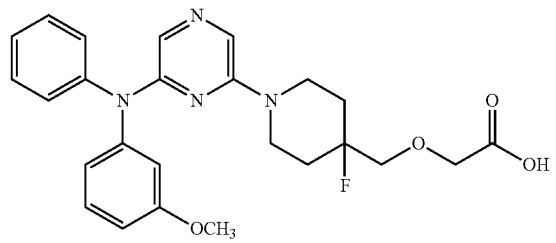
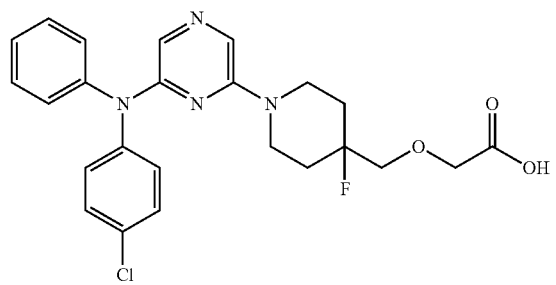
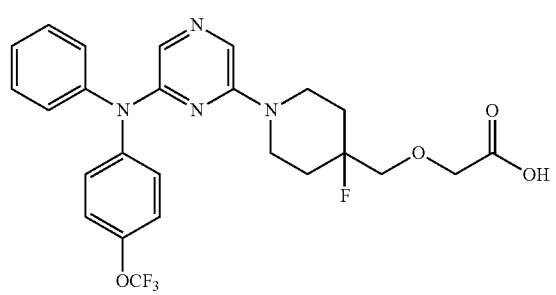
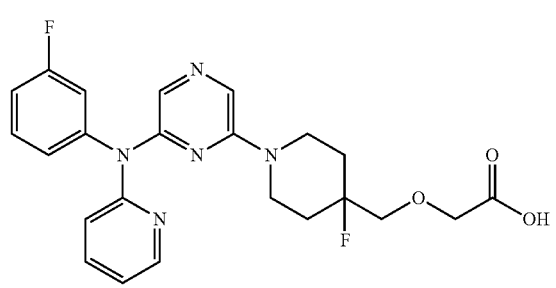
112
-continued
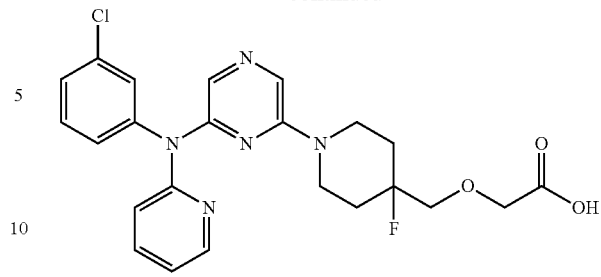
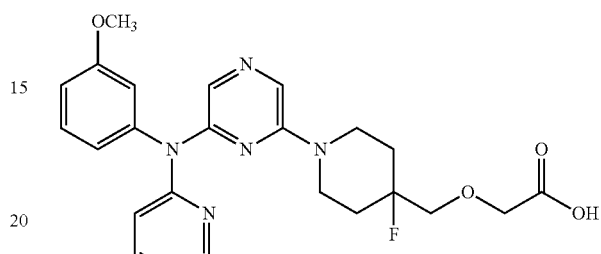
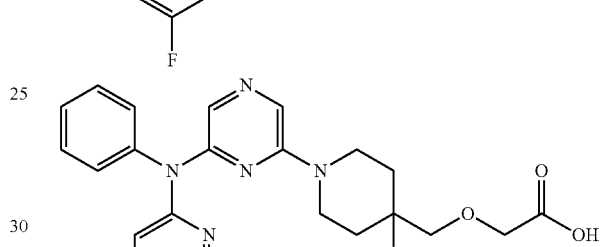
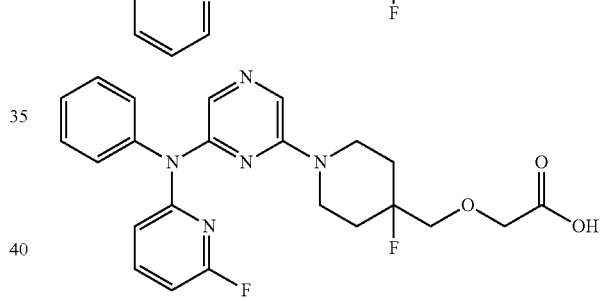
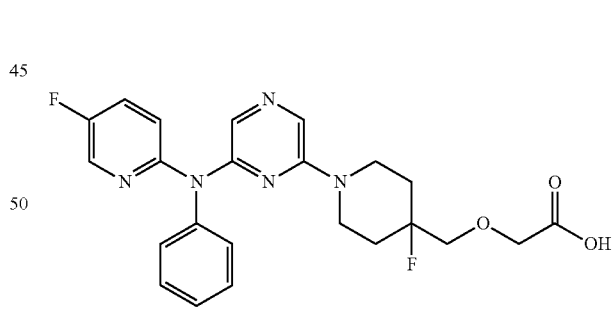
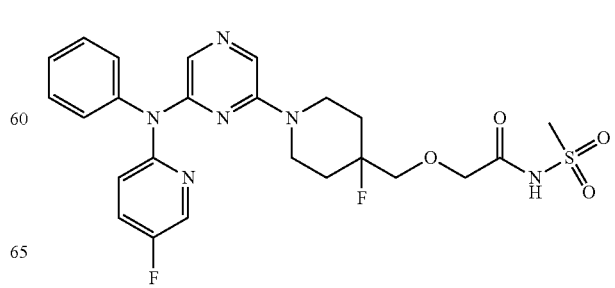

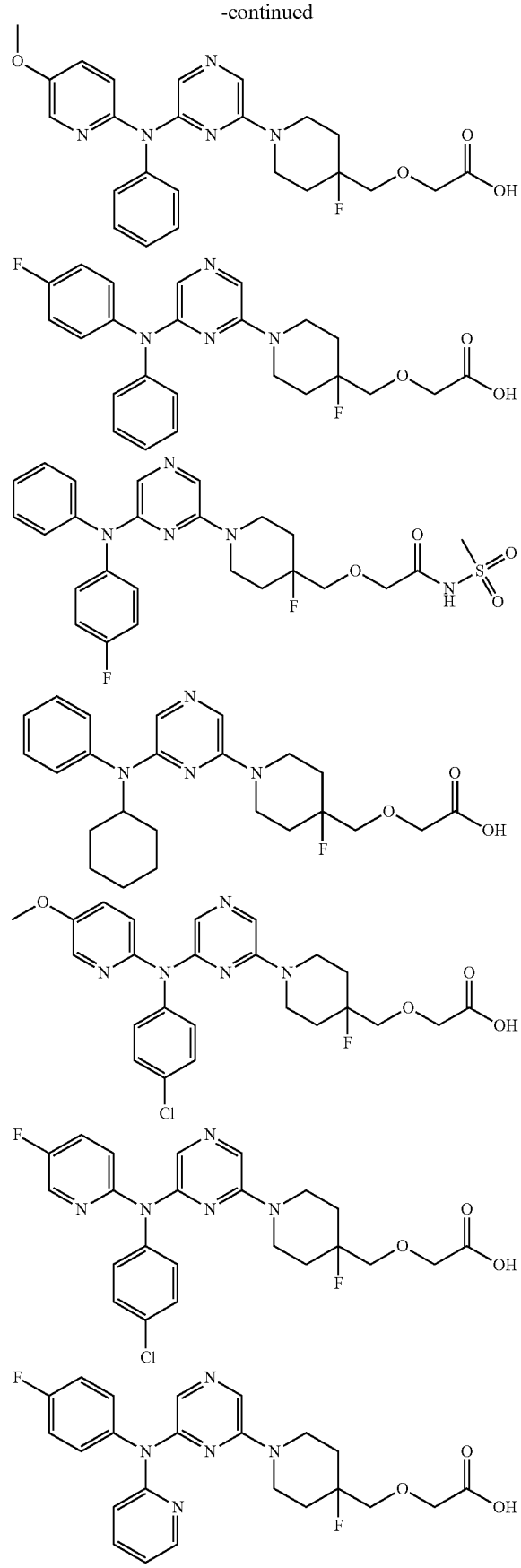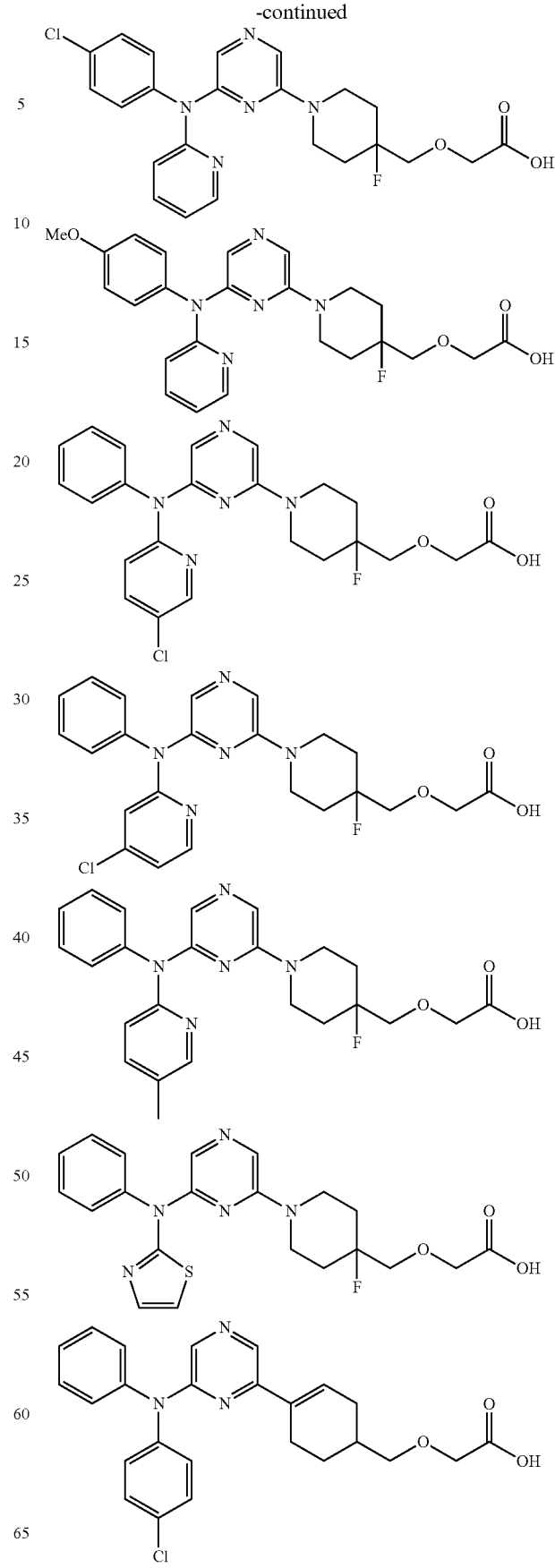

-continued

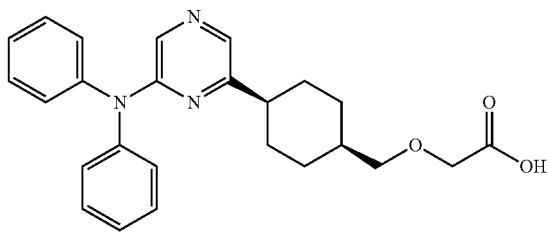

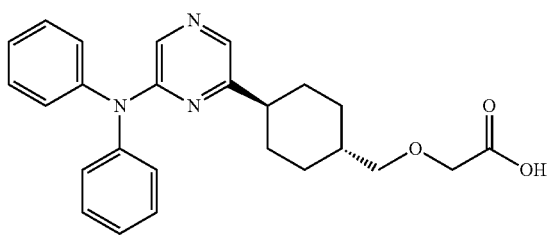

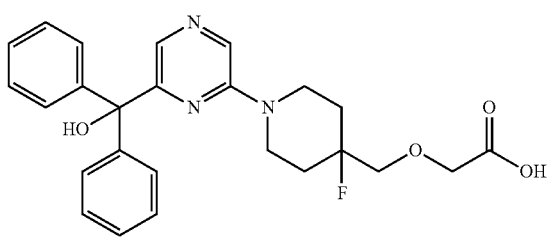

-continued

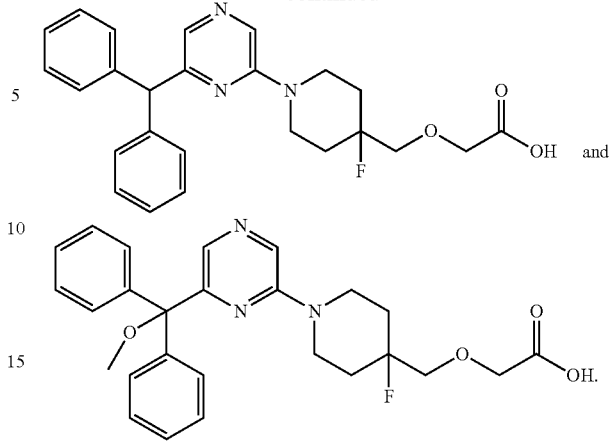

19. A method of modulating PGI$_2$ receptors in a subject in need thereof, comprising administering the compound, the isomer or the pharmaceutically acceptable salt thereof as defined in claim 1 to the subject.

20. A method for treating PGI2 receptor related disease in a subject in need thereof, comprising administering the compound, the isomer or the pharmaceutically acceptable salt thereof as defined in claim 1 to the subject, wherein the PGI$_2$ receptor related disease is pulmonary arterial hypertension, systemic sclerosis, acute pulmonary embolism, renal failure, heart failure, rhinitis, thrombosis, arteriosclerosis, chronic thromboembolic pulmonary arterial hypertension, Raynaud's disease, headache, migraine or cardiac arrest.

* * * * *